(12) United States Patent
Yang et al.

(10) Patent No.: US 12,186,304 B2
(45) Date of Patent: Jan. 7, 2025

(54) METHOD FOR TREATING CANCER BY COMBINATION OF IAP INHIBITOR AND MODULATOR OF IMMUNE CHECKPOINT MOLECULE

(71) Applicant: ASCENTAGE PHARMA (SUZHOU) CO., LTD., Suzhou (CN)

(72) Inventors: Dajun Yang, Suzhou (CN); Yifan Zhai, Suzhou (CN); Douglas Dong Fang, Suzhou (CN); Guangfeng Wang, Suzhou (CN); Qiuqiong Tang, Suzhou (CN); Wentao Pan, Suzhou (CN); Jiao Ji, Suzhou (CN)

(73) Assignee: Ascentage Pharma (Suzhou) Co., LTD., Jiangsu (CN)

( * ) Notice: Subject to any disclaimer, the term of this patent is extended or adjusted under 35 U.S.C. 154(b) by 423 days.

(21) Appl. No.: 16/618,792

(22) PCT Filed: Jul. 30, 2019

(86) PCT No.: PCT/CN2019/098331
§ 371 (c)(1),
(2) Date: Dec. 2, 2019

(87) PCT Pub. No.: WO2020/024932
PCT Pub. Date: Feb. 6, 2020

(65) Prior Publication Data
US 2021/0330642 A1 Oct. 28, 2021

(30) Foreign Application Priority Data

| Jul. 31, 2018 | (CN) | ......................... 201810859866.6 |
| Feb. 11, 2019 | (WO) | ................ PCT/CN2019/074791 |
| May 27, 2019 | (WO) | ................ PCT/CN2019/088527 |
| Jun. 28, 2019 | (CN) | ......................... 201910575352.2 |

(51) Int. Cl.
| A61K 31/407 | (2006.01) |
| A61K 9/00 | (2006.01) |
| A61K 31/337 | (2006.01) |
| A61K 31/5517 | (2006.01) |
| A61K 31/555 | (2006.01) |
| A61K 39/00 | (2006.01) |
| A61P 35/00 | (2006.01) |
| C07K 16/28 | (2006.01) |

(52) U.S. Cl.
CPC .......... *A61K 31/407* (2013.01); *A61K 9/0019* (2013.01); *A61K 31/337* (2013.01); *A61K 31/5517* (2013.01); *A61K 31/555* (2013.01); *A61P 35/00* (2018.01); *C07K 16/2818* (2013.01); *A61K 2039/505* (2013.01); *A61K 2039/545* (2013.01)

(58) Field of Classification Search
CPC .............................. A61K 31/407; A61P 35/00
See application file for complete search history.

(56) References Cited

FOREIGN PATENT DOCUMENTS

| CN | 107987083 A | 5/2018 | |
| WO | 2014031487 A1 | 2/2014 | |
| WO | 2015109391 A1 | 7/2015 | |
| WO | 2016054555 A2 | 4/2016 | |
| WO | 2017020858 A1 | 2/2017 | |
| WO | 2017143449 A1 | 8/2017 | |
| WO | WO-2019122941 A1 * | 6/2019 | ........... A61K 39/395 |

OTHER PUBLICATIONS

"CDC—Skin Cancer Prevention", http://www.cdc.gov/cancer/skin/basic_info/prevention.htm, accessed Aug. 29, 2013 (Year: 2013).*
Chen. Frontiers in Pharmacology, 2018, 9, article 1298, 1-13, published Nov. 6, 2018 (Year: 2018).*
Mehrotra. Cancer Cell, 2010, 17, 53-64 (Year: 2010).*
Tian et al., "Synergistic effects of IAP inhibitor LCL161 and paclitaxel on hepatocellular carcinoma cells". Cancer Letters(2014), vol. 351, pp. 232-241.
Rathore et al., "Overcoming chemotherapy drug resistance by targeting inhibitors of apoptosis proteins (IAPs)", Apoptosis(2017), vol. 22, pp. 898-919.
Wentao Pan et al., "Abstract 1754: Smac mimetics APG-1387 synergizes with immune checkpoint inhibitors in preclinical models", Cancer Research, DOI: 10.1158/1538-7445.AM2018-1754.
Ruihua Xu, et al., "A phase I study of a novel IAP inhibitor APG-1387 in patients with advanced solid tumors", Journal of Clinical Oncology, vol. 36, No. 15_suppl. 2593-2593. DOI: 10.1200/JCO.2018.36.15_suppl.2593.
Anonymous, "APG-1387 in Patients With Advanced Solid Tumors or Hematologic Malignancies", NCT03386526, Dec. 21, 2017 (Dec. 21, 2017).
Yang C.et al., "LCL 161 increases paclitaxel-induced apoptosis by degrading cIAP1 and cIAP2 in NSCLC", Journal of Experimental & Clinical Cancer Research, vol. 35, Dec. 31, 2016 (Dec. 31, 2016), 158-175.
Anonymous, "Dose-escalation Study of Birinapant and Pembrolizumab in Solid Tumors", NCT02587962, Oct. 27, 2015 (Oct. 27, 2015).
Gately, M. K. et al., "The Interleukin-12/Interleukin-12-Receptor System: Role in Normal and Pathologic Immune Responses", Annu. Rev. Immunol. (1998), vol. 16, pp. 495-521.
Clarke, R. et al., "Issues in experimental design and endpoint analysis in the study of experimental cytotoxic agents in vivo in breast cancer and other models", Breast Cancer Research and Treatment (1997), vol. 46, pp. 255-278.

(Continued)

*Primary Examiner* — Noble E Jarrell
(74) *Attorney, Agent, or Firm* — Harness, Dickey & Pierce, P.L.C.

(57) ABSTRACT

The present disclosure pertains to the field of biomedicine, and specifically relates to a method for treating, suppressing, reducing the severity of, lowering the risk of, or inhibiting the metastasis of cancer in an individual, the method comprising administering to the individual a therapeutically effective amount of an IAP inhibitor, a therapeutically effective amount of a modulator of an immune checkpoint molecule, and optionally a therapeutically effective amount of a tubulin inhibitor. The present disclosure further relates to a pharmaceutical composition or kit comprising an IAP inhibitor, a modulator of an immune checkpoint molecule, and optionally a tubulin inhibitor.

22 Claims, 20 Drawing Sheets

(56) References Cited

OTHER PUBLICATIONS

Li, B.-X. et al., "Novel smac mimetic APG-1387 elicits ovarian cancer cell killing through TNF-alpha, Ripoptosome and autophagy mediated cell death pathway", Journal of Experimental & Clinical Cancer Research (2018), vol. 37, p. 53.
Vivier, E. et al., "Innate or Adaptive Immunity? The Example of Natural Killer Cells", Science (Jan. 2011), vol. 331 (6013), pp. 44-49.
Rasco, D. W. et al., "A phase I study of a novel IAP inhibitor APG-1387 as a monotherapy or in combination with pembrolizumab in treatments of patients with advanced solid tumors", Journal of Clinical Oncology (May 2019), vol. 37 (15_suppl), pp. 3125-3125.

\* cited by examiner

| Treatment | Survival Median (days) | Prolong Survival (day) |
|---|---|---|
| Negative control group | 28.0 | - |
| APG-1387 0.2 mg/kg | 33.0 | 5.0 |
| Anti-PD-1 100 μg/mouse | 34.5 | 6.5 |
| APG-1387 + anti-PD-1 | 47.5* | 19.5 |
| *P < 0.05, compared with isotype control group | | |

A

B

C

D

| Treatment | Survival Median (day) | Prolong Survival (day) |
|---|---|---|
| Isotype control | 38 | - |
| APG-1387 0.2 mg/kg | 46 | 8 |
| Anti-PD-1 100 μg/mouse | 46 | 8 |
| APG-1387 + anti-PD-1 | 60 | 22 |

A

B

A

B

A

B

A

B

METHOD FOR TREATING CANCER BY COMBINATION OF IAP INHIBITOR AND MODULATOR OF IMMUNE CHECKPOINT MOLECULE

TECHNICAL FIELD

The present disclosure pertains to the field of biomedicine, and specifically relates to a method for treating, suppressing, reducing the severity of, lowering the risk of, or inhibiting the metastasis of cancer in an individual, the method comprising administering to the individual a therapeutically effective amount of an IAP inhibitor, a therapeutically effective amount of a modulator of an immune checkpoint molecule, and optionally a therapeutically effective amount of a tubulin inhibitor. The present disclosure further relates to a pharmaceutical composition or kit comprising an IAP inhibitor, a modulator of an immune checkpoint molecule, and optionally a tubulin inhibitor.

BACKGROUND ART

Anti-apoptotic protein (IAP) is a protein capable of negatively regulating cysteine protease (caspase) and apoptosis. The expression of IAP protein increases in many cancers and is considered to be a common cause of resistance to many anticancer drugs. DNA amplification of cellular IAP-1 (cIAP-1) and IAP-2 (cIAP-2) genes (BIRC2 and BIRC3, respectively) has been found in a variety of human cancers, including lung cancer, pancreatic cancer and liver cancer. Dysregulation of IAP protein is also frequently observed at the protein level in various cancer cell lines and tumor samples. IAP promotes tumor cell survival and is closely related to drug resistance, disease progression and poor prognosis. In addition, IAP also plays an important role in immune regulation. For example, IAP regulates innate immune signals by activating nuclear transcription factor κB (NF-κB) via a ubiquitin (Ub) dependent pathway. Due to the remarkable biological functions of IAP protein in apoptosis and immune response, IAP has become a drug target for many malignant tumors.

At present, several IAP inhibitors (such as LCL161 and Birinapant) have been developed, among which APG-1387 is a novel IAP inhibitor capable of targeting XIAP, cIAP1 and cIAP2 simultaneously. In a variety of cancer cells and xenograft tumors, APG-1387 induces degradation of cIAP-1 and XIAP proteins, as well as casepase-3 activation and PARP shearing, leading to apoptosis.

SUMMARY OF THE INVENTION

In one aspect, the present disclosure provides a method for treating, suppressing, reducing the severity of, lowering the risk of, or inhibiting the metastasis of cancer in an individual, the method comprising administering to the individual a therapeutically effective amount of an IAP inhibitor and a therapeutically effective amount of a modulator of an immune checkpoint molecule.

In another aspect, the present disclosure provides use of an IAP inhibitor in the preparation of a medicament for use in combination with a modulator of an immune checkpoint molecule to treat, suppress, reduce the severity of, lower the risk of, or inhibit the metastasis of cancer in an individual.

In another aspect, the present disclosure provides an IAP inhibitor for use in combination with a modulator of an immune checkpoint molecule to treat, suppress, reduce the severity of, lower the risk of, or inhibit the metastasis of cancer in an individual.

In another aspect, the present disclosure provides a pharmaceutical composition comprising an IAP inhibitor, a modulator of an immune checkpoint molecule, and a pharmaceutically acceptable carrier.

In another aspect, the present disclosure provides a kit comprising:
(a) a first component in a first container, the first component comprising an IAP inhibitor and optionally a pharmaceutically acceptable carrier;
(b) a second component in a second container, the second component comprising a modulator of an immune checkpoint molecule and optionally a pharmaceutically acceptable carrier; and
(c) optionally an instruction.

In one aspect, the present disclosure provides a method for treating, suppressing, reducing the severity of, lowering the risk of, or inhibiting the metastasis of cancer in an individual, the method comprising administering to the individual a therapeutically effective amount of an IAP inhibitor, a therapeutically effective amount of a modulator of an immune checkpoint molecule, and a therapeutically effective amount of a tubulin inhibitor.

In another aspect, the present disclosure provides use of an IAP inhibitor in the preparation of a medicament for use in combination with a modulator of an immune checkpoint molecule and a tubulin inhibitor to treat, suppress, reduce the severity of, lower the risk of, or inhibit the metastasis of cancer in an individual.

In another aspect, the present disclosure provides an IAP inhibitor for use in combination with a modulator of an immune checkpoint molecule and a tubulin inhibitor to treat, suppress, reduce the severity of, lower the risk of, or inhibit the metastasis of cancer in an individual.

In another aspect, the present disclosure provides a pharmaceutical composition comprising an IAP inhibitor, a modulator of an immune checkpoint molecule, a tubulin inhibitor, and a pharmaceutically acceptable carrier.

In another aspect, the present disclosure provides a kit comprising:
(a) a first component in a first container, the first component comprising an IAP inhibitor and optionally a pharmaceutically acceptable carrier;
(b) a second component in a second container, the second component comprising a modulator of an immune checkpoint molecule and optionally a pharmaceutically acceptable carrier;
(c) a third component in a third container, the third component comprising a tubulin inhibitor and optionally a pharmaceutically acceptable carrier; and
(d) optionally an instruction.

In certain embodiments in the present disclosure, the IAP inhibitor is a compound of formula (I) or a pharmaceutically acceptable salt thereof:

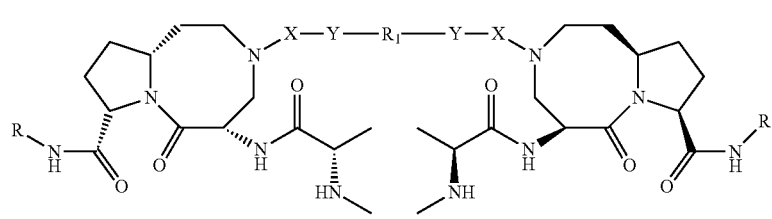
(I)
wherein
X is selected from
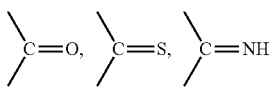
and —SO$_2$—;
Y is selected from —NH—, —O—, —S—, and absence;
R is selected from
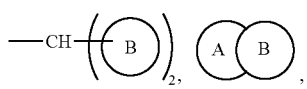
—C$_{3-6}$ cycloalkylene
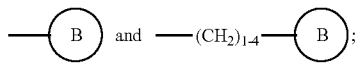
R$_1$ is selected from —(CH$_2$)$_{4-10}$—,
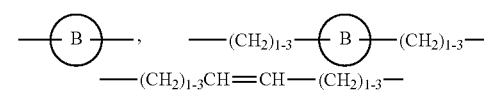
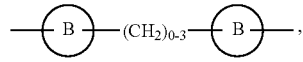
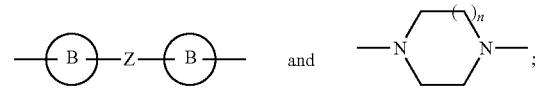
Z is O, S or NH;
n is 0, 1 or 2;
Ring A is a C$_{4-8}$ aliphatic ring; and
B ring is phenyl, naphthyl, pyridyl, pyridazinyl, pyrazinyl or pyrimidinyl, and B ring is optionally substituted.
In certain embodiments, R is:
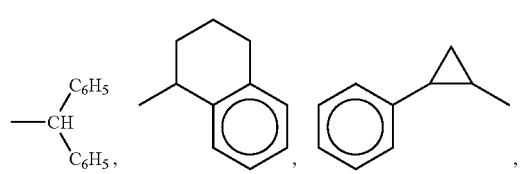
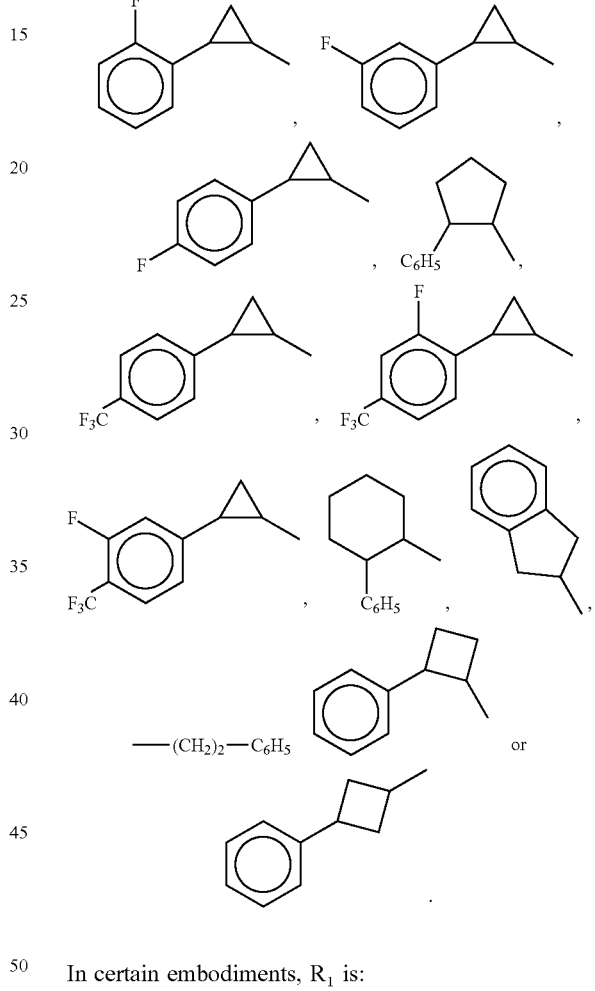
In certain embodiments, R$_1$ is:
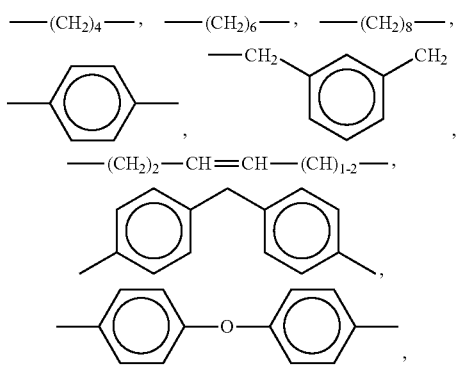

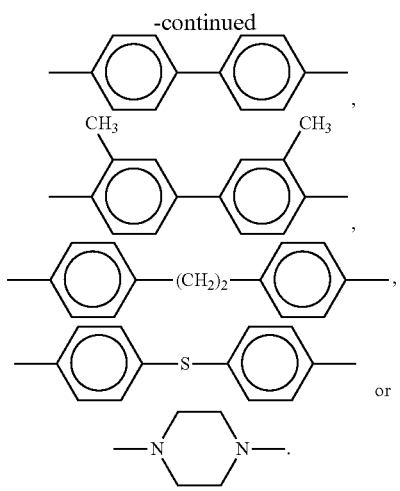

In certain embodiments, X is SO$_2$, and Y is absent.

In certain embodiments, the compound of formula (I) is:

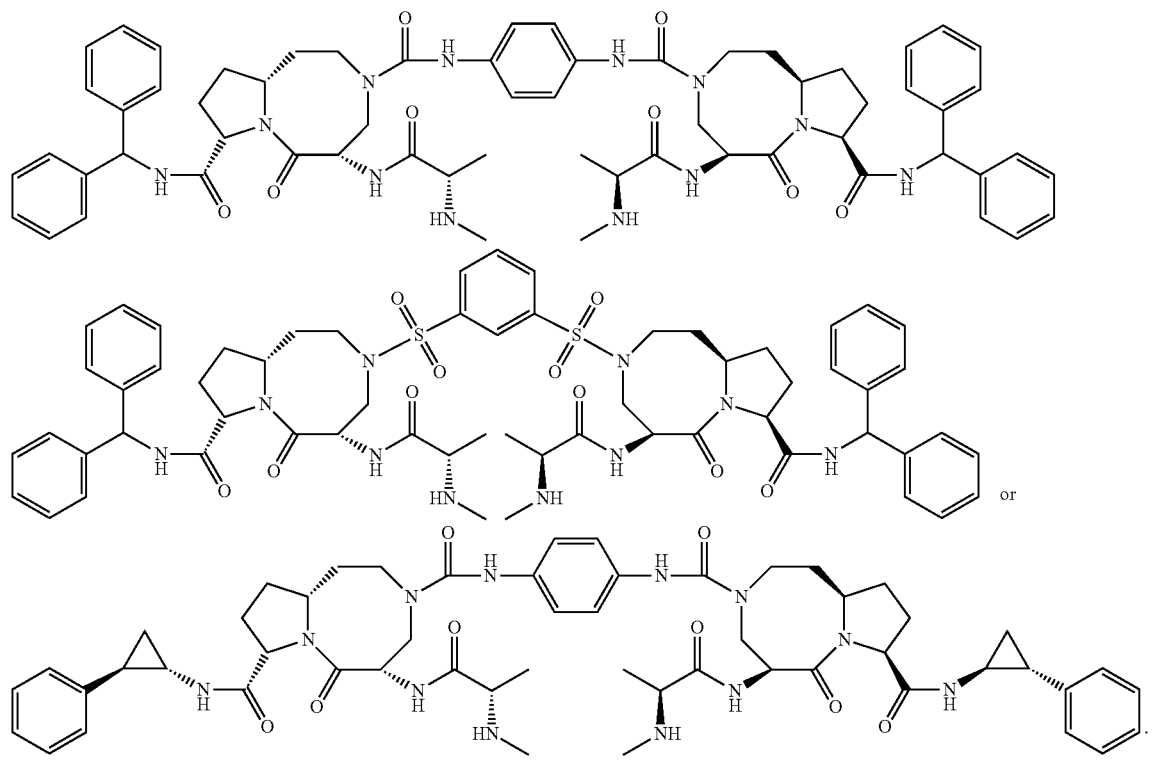

In certain embodiments in the present disclosure, the modulator of an immune checkpoint molecule is an antibody, an antibody Fab fragment, a bivalent antibody, an antibody-drug conjugate, an scFv, a fusion protein, or a tetravalent antibody, and preferably, the modulator of an immune checkpoint molecule is a monoclonal antibody or an antigen-binding fragment thereof.

In certain embodiments, the immune checkpoint molecule is PD-1, PD-L1, PD-L2, CTLA-4, TIM-3, LAG3, CD160, 2B4, TGFβ, VISTA, BTLA, TIGIT, LAIR1, OX40, CD2, CD27, CDS, ICAM-1, NKG2C, SLAMF7, NKp80, B7-H3, LFA-1, 1COS, 4-1BB, GITR, CD30, CD40, BAFFR, HVEM, CD7, LIGHT or CD83 ligand, and preferably, the immune checkpoint molecule is PD-1, PD-L1 or CTLA-4.

In certain embodiments, the modulator of an immune checkpoint molecule is used for restoring anti-tumor T cell activity and/or blocking T cell suppressor cell activity.

In certain embodiments, the modulator of an immune checkpoint molecule is a costimulatory checkpoint molecular activator that alters the costimulatory signal required for intact T cell activation.

In certain embodiments, the modulator of an immune checkpoint molecule is anti-PD-1 antibody, anti-CTLA-4 antibody, or anti-PD-L1 antibody.

In certain embodiments, the modulator of an immune checkpoint molecule is pembrolizumab, ipilimumab, nivolumab, atezolizumab, avelumab, durvalumab, AGEN-1884, BMS-986016, CS1001 (WO2017020858A1, all of which is incorporated herein to its entirety), CS-1002, LAG525, MBG453, MEDI-570, OREG-103/BY40, lirilumab, tremelimumab, JS001, SHR-1210, BGB-A317, IBI-308, REGN2810, JS003, SHR-1316, KN035 or BMS-936559, and preferably, the modulator of an immune checkpoint molecule is pembrolizumab.

In certain embodiments, the tubulin inhibitor is selected from paclitaxel (Taxol), epothilone, docetaxel, discodermolide, colchicine, combretastatin, 2-methoxyestradiol, methoxybenzenesulfonamide (E7010), vinblastine, vincristine, vinorelbine, vinfluine, dolastatin, halichondrin, hemiasterlin and cryptophysin 52.

In certain embodiments, the tubulin inhibitor is docetaxel or paclitaxel.

In some embodiments above, the IAP inhibitor is APG-1387, the modulator of an immune checkpoint molecule is anti-PD-1 antibody, and the tubulin inhibitor is docetaxel or paclitaxel.

In certain embodiments, the IAP inhibitor, the modulator of an immune checkpoint molecule, and the tubulin inhibitor are administered together, concurrently, sequentially or alternatively.

In certain embodiments, the IAP inhibitor, the modulator of an immune checkpoint molecule, or the tubulin inhibitor is administered by a same or different route of administration, including oral administration, intravenous injection or subcutaneous injection.

In certain embodiments, the IAP inhibitor enhances the efficacy of the modulator of an immune checkpoint molecule and/or the tubulin inhibitor in treating cancer and/or reduces the side effects of the modulator of an immune checkpoint molecule and/or the tubulin inhibitor in treating cancer.

In certain embodiments, the IAP inhibitor has the effect of activating or improving an antigen-specific immune response.

In some embodiments, the present disclosure provides the method for treating cancer comprising administering to a patient in need thereof a therapeutically effective amount of an IAP inhibitor, wherein the method comprises at least one 21-day treatment cycle, wherein an IAP inhibitor is administrated on days 1, 8 and 15 of the consecutive 3-weeks of the treatment cycle.

In certain embodiments, the IAP inhibitor is APG-1387.

In certain embodiments, APG-1387 is administrated via intravenous infusion.

In certain embodiments, the therapeutically effective amount of an IAP inhibitor is from about 15 mg to about 100 mg, or from 20 mg to 45 mg, or from 20 mg to 60 mg. In some embodiments, the therapeutically effective amount is 20 mg, 30 mg, 45 mg, 60 mg, and 80 mg.

In certain embodiments, the IAP inhibitor is administered in combination with one or more systemic anti-cancer agents.

In certain embodiments, the systemic anti-cancer agents are selected from anti-PD-1 antibody (for example, pembrolizumab), tubulin inhibitor (for example, paclitaxel and docetaxel), or carboplatin. In some embodiments, pembrolizumab, paclitaxel, and docetaxel is independently administrated intravenously.

In certain embodiments, the cancer is an early stage cancer, a metaphase cancer or an advanced cancer. Preferably, the cancer is selected from adrenocortical cancer, anal cancer, cholangiocarcinoma, bladder cancer, bone cancer, bone metastasis cancer, adult brain/central nervous system tumor, childhood brain/central nervous system tumor, breast cancer, male breast cancer, childhood cancer, primary cancer unknown cancer, Castleman disease, Merkel cell carcinoma, cervical cancer, colon cancer, colorectal cancer, endometrial cancer, esophageal cancer, Ewing's sarcoma family tumor, eye cancer, gallbladder cancer, digestive tract cancer (such as gastric cancer), gastrointestinal stromal tumor (GIST), trophoblastic cancer, head and neck cancer, Kaposi's sarcoma, renal cancer, renal cell cancer, laryngeal and hypopharyngeal cancer, leukemia (such as acute lymphocytic leukemia (ALL), acute myelocytic leukemia (acute myeloid leukemia, AML), chronic lymphocytic leukemia (CLL), chronic granulocytic leukemia (CML), chronic myelomonocytic leukemia (CMML) or childhood leukemia), liver cancer (such as hepatocellular carcinoma), lung cancer (such as non-small cell lung cancer or small cell lung cancer), lymphoma, cutaneous lymphoma, malignant mesothelioma, multiple myeloma, myelodysplastic syndrome, nasal and nasalsinus cancer, nasopharyngeal cancer, neuroblastoma, Hodgkin's lymphoma, non-Hodgkin's lymphoma, childhood non-Hodgkin's lymphoma, oral and oropharyngeal cancer, osteosarcoma, ovarian cancer, pancreatic cancer, penile cancer, malignant pituitary tumor, prostate cancer, retinoblastoma, rhabdomyosarcoma, salivary gland cancer, sarcoma (such as adult soft tissue cancer or uterine sarcoma), skin cancer (such as basal and squamous cell cancer or melanoma), small intestinal cancer, testicular cancer, thymic cancer, thyroid cancer, vaginal cancer, vulvar cancer, Waldenstrom macroglobulinemia, Wilms tumor, urothelial cancer, microsatellite instability solid tumor (high or mismatch repair defect) and choriocarcinoma, and preferably, the cancer is head and neck cancer, microsatellite instability solid tumor, Hodgkin's lymphoma, non-Hodgkin's lymphoma, non-small cell lung cancer, renal cell cancer, bladder cancer, melanoma, squamous cell carcinoma, Merkel cell tumor, urothelial cancer or colorectal cancer.

In every embodiment above, the cancer is an advanced solid tumor or hematologic malignancies, and preferably, the cancer is metastatic pancreatic cancer, colorectal cancer, ovarian cancer, lymphoma, or liver cancer (such as hepatocellular carcinoma).

In every embodiment above, the individual suffers from an advanced cancer. In some embodiments, the individual suffers from a refractory cancer, a recurrent cancer or a resistant cancer, especially a cancer that is resistant to a cancer therapy comprising the modulator of an immune checkpoint molecule and/or tubulin inhibitor.

In another aspect, the present disclosure provides a method for activating or improving antigen-specific immune response in individuals, the method comprising administering to the individual a therapeutically effective amount of an IAP inhibitor to activate or improve the individual's antigen-specific immune response.

In certain embodiments, the IAP inhibitor is APG-1387.

In certain embodiments, the antigen is tumor antigen.

In certain embodiments, the antigen-specific immune response includes increasing the proportion of effector memory cells.

In some embodiments, the effector memory cells comprise effector memory CD4+ T cells and/or effector memory CD8+ T cells.

In certain embodiments, the antigen-specific immune response comprises increasing the proportion of NK cells stimulated by antigen.

In certain embodiments, the antigen-specific immune response comprises increasing the expression of MHC-II in antigen-presenting cells.

In certain embodiments, the activation or improvement of the antigen-specific immune response is dependent upon IL-12.

BRIEF DESCRIPTION OF THE DRAWINGS

FIG. 10. Change in serum cytokine levels after APG-1387 treatment. Heat map of cytokine levels in serum collected from patients at baseline and on day 16 of the first treatment cycle (24 hr after APG-1387 treatment), shown as normalized to the baseline for each individual patient.

DETAILED DESCRIPTION

Figure 1:
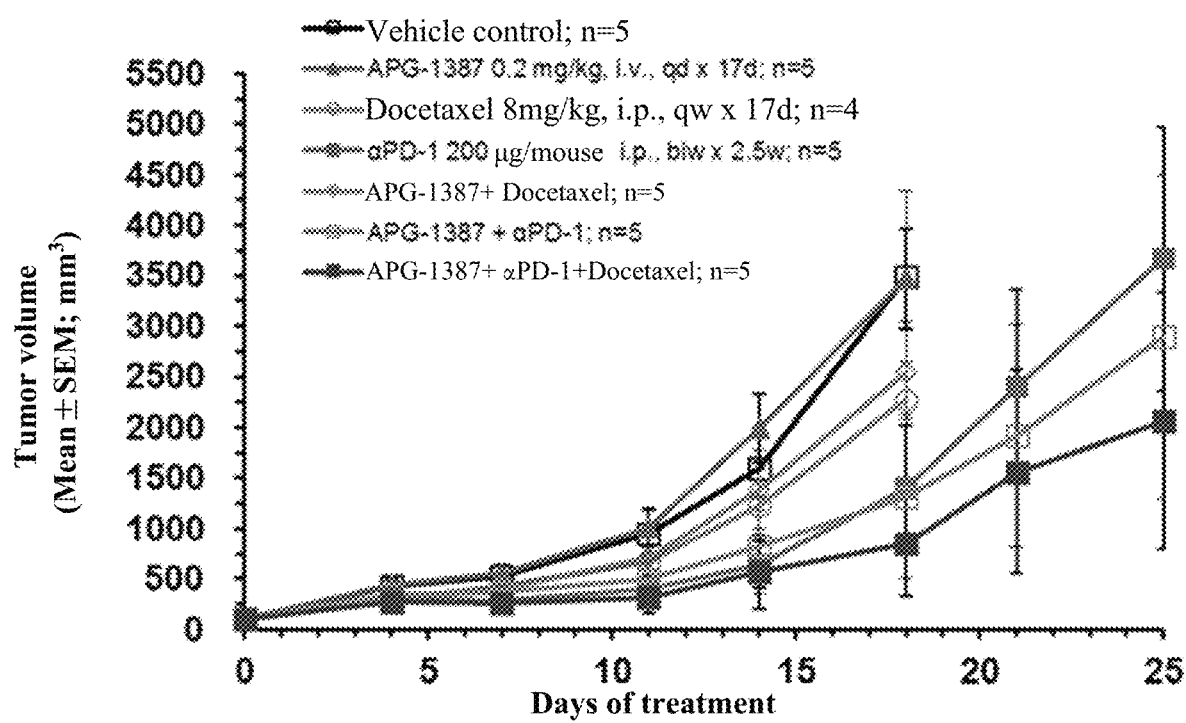
FIG. 1. Synergistic anti-tumor effect of combination therapy by APG-1387 with anti-PD-1 antibody and docetaxel in CT26 mouse colorectal cancer model.

Unless otherwise defined hereinafter, all technical and scientific terms used herein are intended to have the same meaning as commonly understood by those skilled in the art. Reference to techniques used herein is intended to refer to techniques commonly understood in the art, including those that are obvious to those skilled in the art as variations of techniques or substitutions of equivalent techniques. While the following terms are believed to be well understood by those skilled in the art, the following definitions are set forth to better explain the present disclosure.

As used herein, the terms "including", "comprising", "having", "containing", or "involving" and other variations thereof are inclusive or open-ended herein, and do not exclude other unlisted elements or method steps.

As used herein, the term "anti-apoptotic protein (IAP)" is a family of highly-conservative endogenous anti-apoptotic factors that inhibits apoptosis mainly by inhibiting Caspase activity and participating in mediating the action of nuclear factor NF-κB.

The term "$C_{4-8}$ aliphatic ring" as used herein refers to cyclobutyl, cyclopentyl, cyclohexyl, cycloheptyl, and cyclooctyl that are unsubstituted or substituted with 1 to 3 groups (e.g., $C_{1-4}$ alkyl, halogen, trifluoromethyl, trifluoromethoxy, hydroxyl, alkoxy, nitro, cyano, alkylamino, or amino).

The term "alkyl" as used herein refers to linear and branched saturated $C_{1-10}$ hydrocarbon groups, non-limiting examples of which include methyl, ethyl, and linear and branched propyl, butyl, pentyl, hexyl, heptyl, octyl, nonyl, and decyl.

The term "$C_{3-6}$ cycloalkylene" refers to a disubstituted cycloalkane having 3 to 6 carbon atoms, for example,

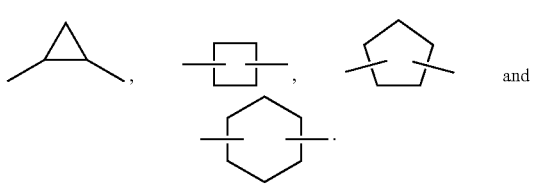

"$C_{3-6}$ cycloalkylene" may be unsubstituted or substituted with 1 to 3 groups such as $C_{1-4}$ alkyl, halogen, trifluoromethyl, trifluoromethoxy, hydroxyl, alkoxy, nitro, cyano, alkylamino or amino.

The term "halogen" as used herein is defined as fluorine, chlorine, bromine, and iodine.

The term "hydroxyl" as used herein is defined as —OH.

The term "alkoxy" as used herein is defined as —OR, wherein R is alkyl.

The term "amino" as used herein is defined as —NH$_2$, and the term "alkylamino" is defined as —NR$_2$, wherein at least one R is alkyl, and the second R is alkyl or hydrogen.

The term "nitro" as used herein is defined as —NO$_2$.

The term "cyano" as used herein is defined as —CN.

The term "trifluoromethyl" as used herein is defined as —CF$_3$.

The term "trifluoromethoxy" as used herein is defined as —OCF$_3$.

The term "optionally substituted" as used herein refers to being optionally substituted with one or more, and in particular one to four groups independently selected from, for example, halogen, alkyl, alkenyl, —OCF$_3$, —NO$_2$, —CN, —NC, —OH, alkoxy, amino, alkylamino, —CO$_2$H, —CO$_2$alkyl, alkynyl, cycloalkyl, nitro, sulfhydryl, imino, amido, phosphonate, phosphinate, silyl, alkylthio, sulfonyl, sulfonamide, aldehyde, heterocycloalkyl, trifluoromethyl, aryl and heteroaryl.

The term "aryl" as used herein refers to monocyclic or polycyclic aromatic group, preferably monocyclic or bicyclic aromatic group, such as phenyl or naphthyl.

The term "heteroaryl" as used herein refers to monocyclic or bicyclic ring system containing one or two aromatic rings and containing at least one and at most four nitrogen atoms in one aromatic ring.

As used herein, the term "pharmaceutically acceptable salt" includes both acid addition salts and base addition salts of a compound.

Suitable acid addition salts are formed from acids that form non-toxic salts. Examples include acetate, adipate, aspartate, benzoate, besylate, bicarbonate/carbonate, bisulfate/sulfate, borate, camphorsulfonate, citrate, cyclamate, ethanedisulfonate, ethanesulfonate, formate, fumarate, glucoheptonate, gluconate, glucuronate, hexafluorophosphate, hibenzate, hydrochloride/chloride, hydrobromide/bromide, hydroiodide/iodide, isethionate, lactate, malate, maleate, malonate, mesylate, methyl sulfate, naphthylate, 2-naphthalenesulfonate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate.

Suitable base addition salts are formed from bases that form non-toxic salts. Examples include aluminum salts, arginine salts, benzathine penicillin salts, calcium salts, choline salts, diethylamine salts, diethanolamine salts, glycine salts, lysine salts, magnesium salts, meglumine salts, ethanolamine salts, potassium salts, sodium salts, tromethamine salts and zinc salts.

For an overview of suitable salts, see Stahl and Wermuth, "Handbook of Pharmaceutical Salts: Properties, Selection, and Use" (Wiley-VCH, 2002). Methods for preparing pharmaceutically acceptable salts of the compounds of the present disclosure are known to those skilled in the art.

As used herein, the term "immune checkpoint" refers to some inhibitory signaling pathways present in the immune system that protect tissues from damage by regulating the persistence and intensity of immune responses in peripheral tissues and participate in maintaining tolerance to autoantigens.

In the present disclosure, the term "antibody-drug conjugate" refers to a substance obtained by linking a drug to an antibody. In some embodiments of the present disclosure, the drug is linked to the antibody through a linker. The linker can be cleaved in a specific environment (e.g., an intracellular low pH environment) or under a specific action (e.g., the action of a lysosomal protease), such that the drug and the antibody are separated. In some embodiments of the present disclosure, the linker comprises a cleavable or non-cleavable unit, such as a peptide or a disulfide bond. In some embodiments of the present disclosure, the drug is linked directly to the antibody by a covalent bond, the covalent bond can be cleaved in a specific environment or under a specific action, such that the drug and the antibody are separated.

In the present disclosure, the term "antibody" is interpreted in its broadest sense, and includes intact monoclonal antibody, polyclonal antibody, and multispecific antibody (e.g., bispecific antibody) formed from at least two intact antibodies, as long as they have the desired biological activity. "Antibody" and "immunoglobulin" are used interchangeably herein.

In the present disclosure, the term "monoclonal antibody" refers to an antibody derived from a group of substantially homogeneous antibodies, i.e., the antibodies constituting the group are identical except for a small number of natural mutations that may be present. A monoclonal antibody has high specificity for one determinant (epitope) of an antigen, whereas a polyclonal antibody contains different antibodies for different determinants (epitopes). In addition to specificity, a monoclonal antibody has the advantage of being free from contamination by other antibodies during synthesis. Here the modifier "monoclonal" means that the antibody is characterized by being derived from a group of substantially homogeneous antibodies and should not be understood as requiring special methods for preparation.

In some embodiments of the present disclosure, the monoclonal antibody further specifically includes a chimeric antibody, i.e., a portion of its heavy chain and/or light chain is identical or homologous to a certain type, a certain class or a certain subclass of antibodies, and the remainder is identical or homologous to another type, another class or another subclass of antibodies, as long as they have the desired biological activity (see, for example, U.S. Pat. No. 4,816,567; and Morrison et al., 1984, PNAS, 81: 6851-6855). Chimeric antibodies useful in the present disclosure include primatized antibodies comprising variable region antigen binding sequences from non-human primates (e.g., old world monkeys or orangutans, etc.) and human constant region sequences.

The term "antibody fragment" refers to a portion of an antibody, preferably an antigen binding region or a variable region. Examples of an antibody fragment include Fab, Fab', F(ab')$_2$, Fd, Fv, dAb, and complementary determining region fragments; bivalent antibodies (diabodies); linear antibodies; and single-chain antibody molecules.

The term "bispecific antibody" is used interchangeably with "bifunctional antibody conjugate" and refers to a conjugate formed by a first antibody (fragment) and a second antibody (fragment) through a conjugating arm. The conjugate retains the activities of the respective antibodies and is therefore bifunctional and bispecific.

The term "multispecific antibody" includes, for example, trispecific antibodies and tetraspecific antibodies, the former being antibodies having three different antigen binding specificities, and the latter being antibodies having four different antigen binding specificities.

The term "intact antibody" refers to an antibody comprising an antigen binding variable region, a light chain constant region (CL), and a heavy chain constant region (CH1, CH2 and CH3). The constant region may be a natural sequence (e.g., a human natural constant region sequence) or an amino acid sequence variant thereof. The intact antibody is preferably an intact antibody having one or more effector functions.

The term "Pro-antibody (Probody)" is a modified antibody which comprises an antibody or an antibody fragment and is capable of specifically binding to its target and capable of coupling to a masking group, wherein the masking group refers to that a cleavage constant for the binding ability of the antibody or antibody fragment to its target is at least 100 times, 1000 times, or 10000 times greater than the cleavage constant for the binding ability of the antibody or antibody fragment without the coupled masking group to its target.

In the present disclosure, a "humanized" form of a non-human (e.g., murine) antibody refers to a chimeric antibody comprising a minimal amount of non-human immunoglobulin sequences. Most humanized antibodies are those in which a hypervariable region residue of human recipient immunoglobulin is replaced with a non-human (e.g., mouse, rat, rabbit or non-human primate) hypervariable region residue (donor antibody) having the desired specificity, affinity and function. In some embodiments, a framework region (FR) residue of human immunoglobulin is also replaced with a non-human residue. Moreover, the humanized antibody may also comprise residues that are not found in a recipient antibody or a donor antibody. These modifications are intended to further optimize the performance of the antibody. The humanized antibody generally comprises at least one, usually two variable regions, wherein all or almost all hypervanable loops correspond to those of non-human immunoglobulin, while FR is entirely or almost entirely a sequence of human immunoglobulin. The humanized antibody may also comprise at least a portion of an immunoglobulin constant region (Fc, typically a human immunoglobulin Fc). For details, see, for example, Jones et al., 1986, Nature, 321: 522-525; Riechmann et al., 1988, Nature, 332: 323-329; and Presta, 1992, Curr Op Struct Bwl 2: 593-596.

Intact antibodies can be divided into different "classes" based on an amino acid sequence of the heavy chain constant region. The main five classes are IgA, IgD, IgE, IgG and IgM, and several of them can further be divided into different "subclasses" (isotypes), such as IgG1, IgG2, IgG3, IgG4, IgA1 and IgA2. The heavy chain constant regions of different classes of antibodies are called α, δ, ε, γ and μ, respectively. Subunit structures and three-dimensional configurations of different classes of immunoglobulins are well known in the art.

In the present disclosure, although the amino acid substitution in an antibody is substitution with L-amino acid in most cases, it is not limited thereto. In some embodiments, one or more D-amino acids may be included in the antibody peptide chain. Peptides comprising D-amino acids are more stable and less degradable in oral cavity, intestinal tract or plasma than peptides comprising only L-amino acids.

The monoclonal antibodies used in the present disclosure can be produced by a number of methods. For example, the monoclonal antibodies for use in the present disclosure can be obtained by hybridoma methods using many species (including cells of mouse, hamster, rat and human) (see, for example, Kohler et al., 1975, Nature, 256: 495), or prepared by recombinant DNA techniques (see, for example, U.S. Pat. No. 4,816,567), or isolated from phage antibody libraries (see, for example, Clackson et al., 1991, Nature, 352: 624-628; and Marks et al., 1991, Journal of Molecular Biology, 222: 581-597).

In the present disclosure, "pharmaceutically acceptable carrier" refers to a diluent, adjuvant, excipient or vehicle which is administered together with a therapeutic agent, and which is suitable for contacting tissues of humans and/or other animals without excessive toxicity, irritation, hypersensitivity reaction, or other problems or complications corresponding to a reasonable benefit/risk ratio within the scope of sound medical judgment.

Pharmaceutically acceptable carriers useful in the pharmaceutical composition or kit of the present disclosure include, but are not limited to, sterile liquids, such as water and oils, including those oils of petroleum, animal, plant or synthetic origin, such as peanut oil, soybean oil, mineral oil, sesame oil, and the like. When the pharmaceutical composition is administered intravenously, water is an exemplary carrier. Physiological saline as well as an aqueous solution of glucose and glycerol can also be used as the liquid carrier, especially for injection. Suitable pharmaceutical excipients include starch, glucose, lactose, sucrose, gelatin, maltose, chalk, silica gel, sodium stearate, glyceryl monostearate, talc, sodium chloride, skimmed milk powder, glycerol, propylene glycol, water, ethanol, and the like. The pharmaceutical composition may further contain a small amount of a wetting agent, emulsifier or pH buffer as needed. Oral formulations may contain a standard carrier, such as pharmaceutical grades of mannitol, lactose, starch, magnesium stearate, sodium saccharin, cellulose, magnesium carbonate, and the like. Examples of suitable pharmaceutically acceptable carriers are as described in Remington's Pharmaceutical Sciences (1990).

The components in the pharmaceutical composition and kit of the present disclosure may act systemically and/or locally. For this purpose, administration can be carried out by a suitable route, for example, by injection (e.g., intravenous, intra-arterial, subcutaneous, intraperitoneal, intramuscular injection, including instillation) or transdermal administration; or orally, buccally, nasally, transmucosally, topically, in the form of ophthalmic preparations or by inhalation.

For these routes of administration, the components in the pharmaceutical composition and kit of the present disclosure may be administered in a suitable dosage form.

The dosage form includes, but is not limited to, tablet, capsule, lozenge, hard candy, powder, spray, cream, ointment, suppository, gel, paste, lotion, ointment, aqueous suspension, injectable solution, elixir and syrup.

The term "container" as used herein is a container for holding pharmaceutical components. This container can be used for preparation, storage, transportation, and/or stand-alone/bulk sale, and is intended to cover bottles, cans, vials, flasks, syringes, tubes (e.g., for cream products), or any other container for preparing, holding, storing or dispensing pharmaceutical products.

The term "instruction" as used herein is an insert, label, directive or the like, which lists information related to the pharmaceutical components within the container. The information to be listed is typically determined by a regulatory agency that governs the area where the product is to be sold (e.g., U.S. Food and Drug Administration). It is preferred that the package instruction specifically lists the indications for which the pharmaceutical components are approved for use.

The package instruction may be made of any materials from which information contained therein or thereon can be read. It is preferred that the package instruction is a printable material (e.g., paper, plastic, cardboard, foil, adhesive paper or plastic, etc.) on which the desired information can be formed (e.g., printed or applied).

The term "effective amount" as used herein refers to the amount of an active ingredient that, after being administered, alleviates one or more symptoms of the disorder being treated to some extent.

"Individual" as used herein includes humans or non-human animals. Exemplary human individuals include human individuals (referred to as patients) suffering from diseases (e.g., diseases described herein) or normal individuals. "Non-human animals" in the present disclosure include all vertebrates, such as non-mammals (e.g., birds, amphibians, reptiles) and mammals, such as non-human primates, domestic animals and/or domesticated animals (e.g., sheeps, dogs, cats, cows, pigs, etc.).

As used herein, "cancer metastasis" refers to a cancer that spreads (metastasizes) from its initial site to another area of the body. Almost all cancers have the potential to spread. Whether metastasis will occur or not depends on the complicated interactions between a plurality of tumor cell factors, including the type of cancer, the degree of maturation (differentiation) of tumor cells, the site and existence time of cancer, and other factors that are not fully understood. Metastatic spread occurs in three ways, that is, locally extending from tumor to surrounding tissues, reaching distant sites through the bloodstream, or reaching adjacent or distant lymph nodes through the lymphatic system. Each cancer may have a representative route of spread. Tumor is named according to the primary site (for example, breast cancer that has spread to brain is called metastatic breast cancer that metastasizes to brain).

As used herein, "resistant" refers to cancer cells that have acquired resistance to chemotherapy. Cancer cells may acquire resistance to chemotherapy through a series of mechanisms, including mutation or overexpression of drug targets, inactivation of drugs, or elimination of drugs from cells.

Combination of IAP Inhibitor and Modulator of an Immune Checkpoint Molecule and/or Tubulin Inhibitor

Treatment Methods and Uses

In one embodiment, the present disclosure provides a method for treating, suppressing, reducing the severity of, lowering the risk of, or inhibiting the metastasis of cancer in an individual, the method comprising administering to the individual a therapeutically effective amount of an IAP inhibitor and a therapeutically effective amount of a modulator of an immune checkpoint molecule.

In another embodiment, the present disclosure provides use of an IAP inhibitor in the manufacture of a medicament for use in combination with a modulator of an immune checkpoint molecule to treat, suppress, reduce the severity of, lower the risk of, or inhibit the metastasis of cancer in an individual.

In another embodiment, the present disclosure provides use of a modulator of an immune checkpoint molecule in the manufacture of a medicament for use in combination with an IAP inhibitor to treat, suppress, reduce the severity of, lower the risk of, or inhibit the metastasis of cancer in an individual.

In another embodiment, the present disclosure provides use of an IAP inhibitor in the manufacture of a medicament for treating, suppressing, reducing the severity of, lowering the risk of, or inhibiting the metastasis of cancer in an individual being treated with a cancer therapy comprising a modulator of an immune checkpoint molecule.

In another embodiment, the present disclosure provides use of a modulator of an immune checkpoint molecule in the manufacture of a medicament for treating, suppressing, reducing the severity of, lowering the risk of, or inhibiting the metastasis of cancer in an individual being treated with a cancer therapy comprising an IAP inhibitor.

In another embodiment, the present disclosure provides an IAP inhibitor for use in combination with a modulator of an immune checkpoint molecule to treat, suppress, reduce the severity of, lower the risk of, or inhibit the metastasis of cancer in an individual.

In another embodiment, the present disclosure provides a modulator of an immune checkpoint molecule for use in combination with an IAP inhibitor to treat, suppress, reduce the severity of, lower the risk of, or inhibit the metastasis of cancer in an individual.

In another embodiment, the present disclosure provides an IAP inhibitor for treating, suppressing, reducing the severity of, lowering the risk of, or inhibiting the metastasis of cancer in an individual being treated with a cancer therapy comprising a modulator of an immune checkpoint molecule.

In another embodiment, the present disclosure provides a modulator of an immune checkpoint molecule for treating, suppressing the severity of, lowering the risk of, or inhibiting the metastasis of cancer in an individual being treated with a cancer therapy comprising an IAP inhibitor.

In one embodiment, the present disclosure provides a method for treating, suppressing, reducing the severity of, lowering the risk of, or inhibiting the metastasis of cancer in an individual, the method comprising administering to the individual a therapeutically effective amount of an IAP inhibitor, a therapeutically effective amount of a modulator of an immune checkpoint molecule and a therapeutically effective amount of a tubulin inhibitor.

In another embodiment, the present disclosure provides use of an IAP inhibitor in the manufacture of a medicament for use in combination with a modulator of an immune checkpoint molecule and a tubulin inhibitor to treat, suppress, reduce the severity of, lower the risk of, or inhibit the metastasis of cancer in an individual.

In another embodiment, the present disclosure provides use of a modulator of an immune checkpoint molecule in the manufacture of a medicament for use in combination with an IAP inhibitor and a tubulin inhibitor to treat, suppress, reduce the severity of, lower the risk of, or inhibit the metastasis of cancer in an individual.

In another embodiment, the present disclosure provides use of a tubulin inhibitor in the manufacture of a medicament for use in combination with an IAP inhibitor and a modulator of an immune checkpoint molecule to treat, suppress, reduce the severity of, lower the risk of, or inhibit the metastasis of cancer in an individual.

In another embodiment, the present disclosure provides use of an IAP inhibitor in the manufacture of a medicament for treating, suppressing, reducing the severity of, lowering the risk of, or inhibiting the metastasis of cancer in an individual being treated with a cancer therapy comprising a modulator of an immune checkpoint molecule and/or a tubulin inhibitor.

In another embodiment, the present disclosure provides use of a modulator of an immune checkpoint molecule in the manufacture of a medicament for treating, suppressing, reducing the severity of, lowering the risk of, or inhibiting the metastasis of cancer in an individual being treated with a cancer therapy comprising an IAP inhibitor and/or a tubulin inhibitor.

In another embodiment, the present disclosure provides use of a tubulin inhibitor in the manufacture of a medicament for treating, suppressing, reducing the severity of, lowering the risk of, or inhibiting the metastasis of cancer in an individual being treated with a cancer therapy comprising an IAP inhibitor and/or a modulator of an immune checkpoint molecule.

In another embodiment, the present disclosure provides an IAP inhibitor for use in combination with a modulator of an immune checkpoint molecule and a tubulin inhibitor to treat, suppress, reduce the severity of, lower the risk of, or inhibit the metastasis of cancer in an individual.

In another embodiment, the present disclosure provides a modulator of an immune checkpoint molecule for use in combination with an IAP inhibitor and a tubulin inhibitor to treat, suppress, reduce the severity of, lower the risk of, or inhibit the metastasis of cancer in an individual.

In another embodiment, the present disclosure provides a tubulin inhibitor for use in combination with an IAP inhibitor and a modulator of an immune checkpoint molecule to treat, suppress, reduce the severity of, lower the risk of, or inhibit the metastasis of cancer in an individual.

In another embodiment, the present disclosure provides an IAP inhibitor for treating, suppressing, reducing the severity of, lowering the risk of, or inhibiting the metastasis of cancer in an individual being treated with a cancer therapy comprising a modulator of an immune checkpoint molecule and/or a tubulin inhibitor.

In another embodiment, the present disclosure provides a modulator of an immune checkpoint molecule for treating, suppressing, reducing the severity of, lowering the risk of, or inhibiting the metastasis of cancer in an individual being treated with a cancer therapy comprising an IAP inhibitor and/or a tubulin inhibitor.

In another embodiment, the present disclosure provides a tubulin inhibitor for treating, suppressing, reducing the severity of, lowering the risk of, or inhibiting the metastasis of cancer in an individual being treated with a cancer therapy comprising an IAP inhibitor and/or a modulator of an immune checkpoint molecule.

In certain embodiments, the IAP inhibitor is an IAP inhibitor as described in WO2014/031487 which is incorporated herein by reference, and can be prepared by the method described therein.

In certain embodiments, the IAP inhibitor is a compound of formula (I) or a pharmaceutically acceptable salt thereof:

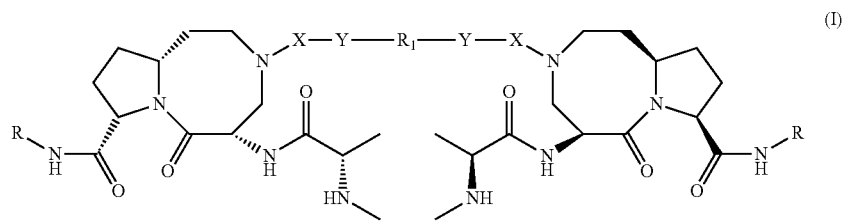

(I)

wherein
X is selected from

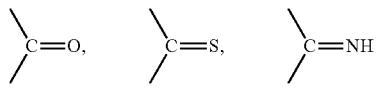

and —SO$_2$—;
Y is selected from —NH—, —O—, —S— and absence;
R is selected from

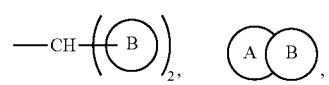

—C$_{3-6}$ cycloalkylene

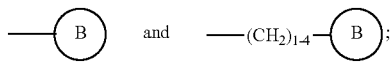

R$_1$ is selected from —(CH$_2$)$_{4-10}$—,

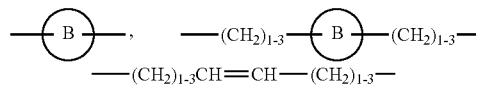

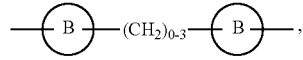

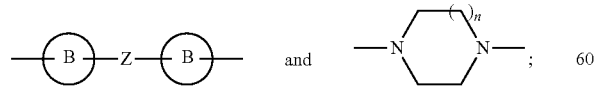

Z is O, S or NH;
n is 0, 1 or 2;
Ring A is a C4-8 aliphatic ring; and
B ring is phenyl, naphthyl, pyridyl, pyridazinyl, pyrazinyl or pyrimidinyl, and B ring is optionally substituted.

In certain embodiments, R is:

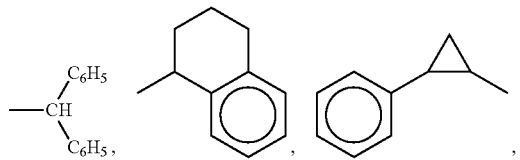

-continued

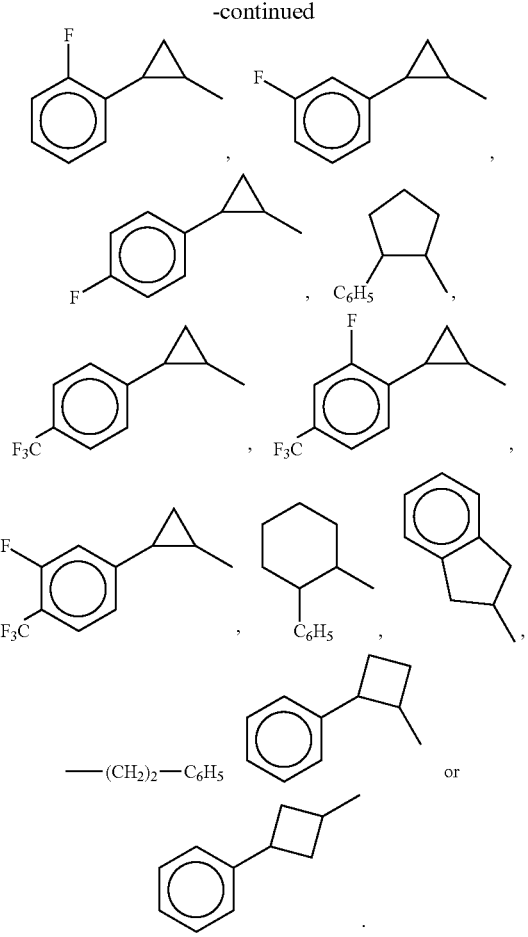

In certain embodiments, R$_1$ is:

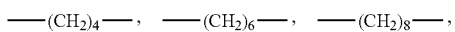

19
-continued
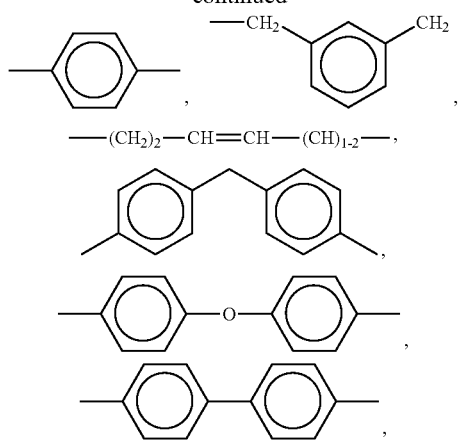
20
-continued
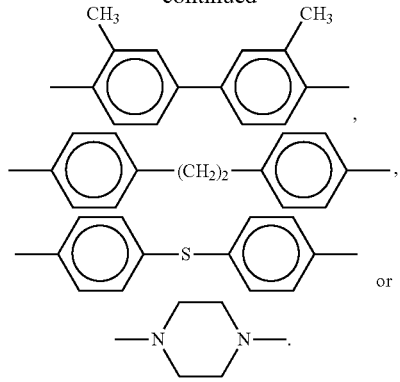
In certain embodiments, X is SO₂, and Y is absent.
In certain embodiments, the compound of formula (I) is:
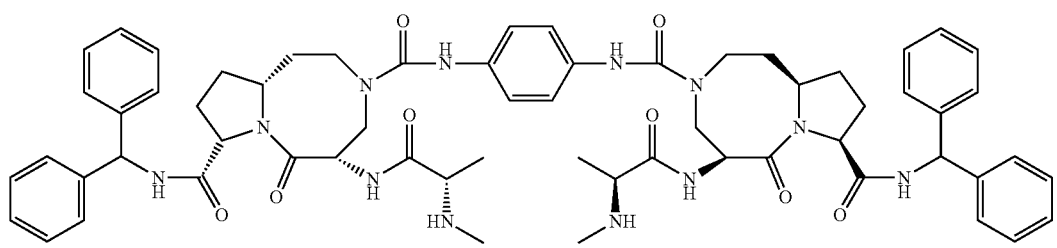
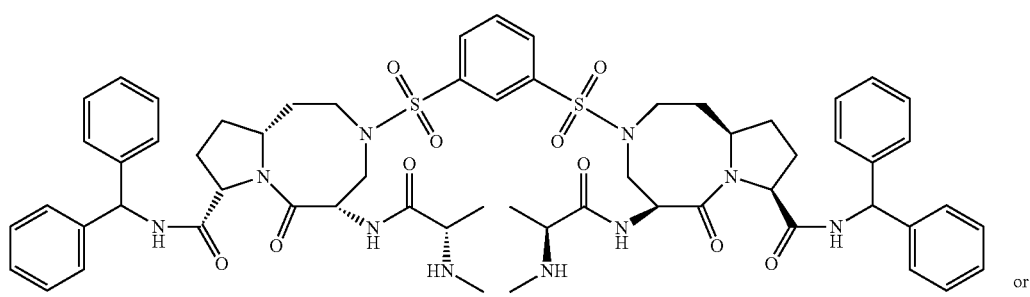
or
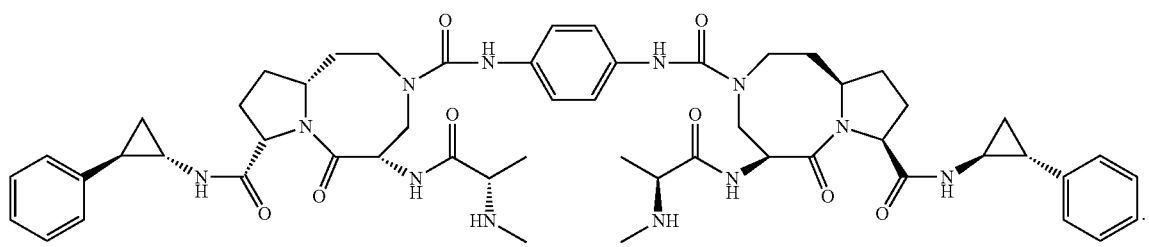
.

In certain embodiments, the compound is APG-1387, i.e., 1,3-phenylenebis[7-(3S,5S,9aR)-5-((S)-2-methylamino-propionamido)-3-diphenylcarbamyl-4-oxo-3a,7-diaza-decahydrocyclopentacyclooctene)]-sulfonamide, having the following structure:

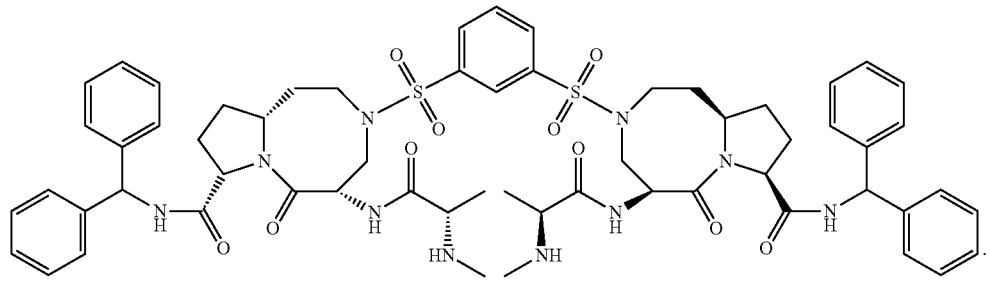

In certain embodiments, the modulator of an immune checkpoint molecule is an antibody, an antibody Fab fragment, a bivalent antibody, an antibody-drug conjugate, an scFv, a fusion protein, or a tetravalent antibody, and preferably, the modulator of an immune checkpoint molecule is a monoclonal antibody or an antigen-binding fragment thereof.

In certain embodiments, the immune checkpoint molecule is PD-1, PD-L1, PD-L2, CTLA-4, TIM-3, LAG3, CD160, 2B4, TGFβ, VISTA, BTLA, TIGIT, LAIR1, OX40, CD2, CD27, CDS, ICAM-1, NKG2C, SLAMF7, NKp80, B7-H3, LFA-1, 1COS, 4-1BB, GITR, CD30, CD40, BAFFR, HVEM, CD7, LIGHT or CD83 ligand, and preferably, the immune checkpoint molecule is PD-1, PD-L1 or CTLA-4.

In certain embodiments, the modulator of an immune checkpoint molecule is used for restoring anti-tumor T cell activity and/or blocking T cell suppressor cell activity.

In certain embodiments, the modulator of an immune checkpoint molecule is a costimulatory checkpoint molecular activator that alters the costimulatory signal required for intact T cell activation.

In certain embodiments, the modulator of an immune checkpoint molecule is anti-PD-1 antibody, anti-CLTA-4 antibody, or anti-PD-L1 antibody.

In certain embodiments, the modulator of an immune checkpoint molecule is pembrolizumab, ipilimumab, nivolumab, atezolizumab, avelumab, durvalumab, AGEN-1884, BMS-986016, CS1001 (WO2017020858A1, all of which is incorporated herein to its entirety), CS-1002, LAG525, MBG453, MEDI-570, OREG-103/BY40, lirilumab, tremelimumab, JS001, SHR-1210, BGB-A317, IBI-308, REGN2810, JS003, SHR-1316, KN035 or BMS-936559, and preferably, the modulator of an immune checkpoint molecule is pembrolizumab.

In certain embodiments, the tubulin inhibitor is selected from paclitaxel (Taxol), epothilone, docetaxel, discodermolide, colchicine, combretastatin, 2-methoxyestradiol, methoxybenzenesulfonamide (E7010), vinblastine, vincristine, vinorelbine, vinfluine, dolastatin, halichondrin, hemiasterlin and cryptophysin 52.

In certain embodiments, the tubulin inhibitor is docetaxel or paclitaxel.

In certain embodiments above, the IAP inhibitor is APG-1387, the modulator of an immune checkpoint molecule is anti-PD-1 antibody, and the tubulin inhibitor is docetaxel or paclitaxel.

In certain embodiments, the IAP inhibitor is administered in an amount of about 0.005 mg/day to about 5000 mg/day, such as about 0.005, 0.05, 0.5, 5, 9, 10, 20, 30, 40, 50, 60, 100, 150, 200, 250, 300, 350, 400, 450, 500, 550, 600, 650, 700, 750, 800, 850, 900, 950, 1000, 1500, 2000, 2500, 3000, 3500, 4000, 4500 or 5000 mg/day. In certain embodiments, the IAP inhibitor is administrated in an amount of about 10 mg/week to about 200 mg/week, or about 20 mg/week to about 100 mg/week, or about 20 mg/week to about 80 mg/week, such as 10, 15, 20, 25, 30, 35, 40, 50, 55, 60, 65, 70, 75, 80, 85, 90, 95, 100, 110, 120, 130, 140, 150, 160, 170, 180, 190, or 200 mg/week.

In certain embodiments, the IAP inhibitor is administered in an amount of about 1 ng/kg to about 200 mg/kg, about 1 μg/kg to about 100 mg/kg, or about 1 mg/kg to about 50 mg/kg per unit dose, such as administered in an amount of about 1 μg/kg, about 10 μg/kg, about 25 μg/kg, about 50 μg/kg, about 75 μg/kg, about 100 μg/kg, about 125 μg/kg, about 150 μg/kg, about 175 μg/kg, about 200 μg/kg, about 225 μg/kg, about 250 μg/kg, about 275 μg/kg, about 300 μg/kg, about 325 μg kg, about 350 μg/kg, about 375 μg/kg, about 400 μg/kg, about 425 μg/kg, about 450 μg/kg, about 475 μg/kg, about 500 μg/kg, about 525 μg/kg, about 550 μg/kg, about 575 μg/kg, about 600 μg/kg, about 625 μg/kg, about 650 μg/kg, about 675 μg/kg, about 700 μg/kg, about 725 μg/kg, about 750 μg/kg, about 775 μg/kg, about 800 μg/kg, about 825 μg/kg, about 850 μg/kg, about 875 μg/kg, about 900 μg/kg, about 925 μg/kg, about 950 μg/kg, about 975 μg/kg, about 1 mg/kg, about 1.5 mg/kg, about 2.5 mg/kg, about 3 mg/kg, about 3.5 mg/kg, about 4 mg/kg, about 4.5 mg/kg, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 60 mg/kg, about 70 mg/kg, about 80 mg/kg, about 90 mg/kg, about 100 mg/kg, about 125 mg/kg, about 150 mg/kg, about 175 mg/kg, and about 200 mg/kg per unit dose, and one or more (e.g., 1, 2, 3, 4, 5, 6, 7, 8, 9 or 10) unit doses are administered every day, every 2 days, every 3 days, every 4 days, every 5 days, every 6 days, or every week.

In certain embodiments, the modulator of an immune checkpoint molecule and/or tubulin inhibitor is administered in an amount of about 0.005 mg to about 5000 mg every week, every 2 weeks, every 3 weeks, or every 4 weeks, such as about 0.005, 0.05, 0.5, 5, 10, 20, 30, 40, 50, 60, 70, 80, 90, 100, 150, 200, 250, 300, 350, 400, 450, 500, 550, 600, 650, 700, 750, 800, 850, 900, 950, 1000, 1500, 2000, 2500, 3000, 3500, 4000, 4500 or 5000 mg every week, every 2 weeks, every 3 weeks, or every 4 weeks.

In certain embodiments, the modulator of an immune checkpoint molecule and/or tubulin inhibitor is administered in an amount of about 1 ng/kg to about 200 mg/kg, about 1

μg/kg to about 100 mg/kg, or about 1 mg/kg to about 50 mg/kg per unit dose, such as administered in an amount of about 1 μg/kg, about 10 μg/kg, about 25 μg/kg, about 50 μg/kg, about 75 μg/kg, about 100 μg/kg, about 125 μg/kg, about 150 μg/kg, about 175 μg/kg, about 200 μg/kg, about 225 μg/kg, about 250 μg/kg, about 275 μg/kg, about 300 μg/kg, about 325 μg/kg, about 350 μg/kg, about 375 μg/kg, about 400 μg/kg, about 425 μg/kg, about 450 μg/kg, about 475 μg/kg, about 500 μg/kg, about 525 μg/kg, about 550 μg/kg, about 575 μg/kg, about 600 μg/kg, about 625 μg/kg, about 650 μg/kg, about 675 μg/kg, about 700 μg/kg, about 725 μg/kg, about 750 μg/kg, about 775 μg/kg, about 800 μg/kg, about 825 μg/kg, about 850 μg/kg, about 875 μg/kg, about 900 μg/kg, about 925 μg/kg, about 950 μg/kg, about 975 μg/kg, about 1 mg/kg, about 1.5 mg/kg, about 2.5 mg/kg, about 3 mg/kg, about 3.5 mg/kg, about 4 mg/kg, about 4.5 mg/kg, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 60 mg/kg, about 70 mg/kg, about 80 mg/kg, about 90 mg/kg, about 100 mg/kg, about 125 mg/kg, about 150 mg/kg, about 175 mg/kg, and about 200 mg/kg per unit dose, and one or more (e.g., 1, 2, 3, 4, 5, 6, 7, 8, 9, 10, 15 or 20) unit doses are administered every week, every 2 weeks, every 3 weeks, or every 4 weeks.

In certain embodiments, the modulator of an immune checkpoint molecule and/or tubulin is administered in an amount of about 1 mg/m$^2$ to about 200 mg/m$^2$, about 1 μg/m$^2$ to about 100 mg/m$^2$, or about 1 mg/m$^2$ to about 50 mg/kg per unit dose, such as administered in an amount of about m2 per unit dose, such as administered in an amount of about 1 μg/m$^2$, about 10 μg/m$^2$, about 25 μg/m$^2$, about 50 μg/m$^2$, about 75 μg/m$^2$, about 100 μg/m$^2$, about 125 μg/m$^2$, about 150 μg/m$^2$, about 175 μg/m$^2$, about 200 μg/m$^2$, about 225 μg/m$^2$, about 250 μg/m$^2$, about 275 μg/m$^2$, about 300 μg/m$^2$, about 325 μg/m$^2$, about 350 μg/m$^2$, about 375 μg/m$^2$, about 400 μg/m$^2$, about 425 μg/m$^2$, about 450 μg/m$^2$, about 475 μg/m$^2$, about 500 μg/m$^2$, about 525 μg/m$^2$, about 550 μg/m$^2$, about 575 μg/m$^2$, about 600 μg/m$^2$, about 625 μg/m$^2$, about 650 μg/m$^2$, about 675 μg/m$^2$, about 700 μg/m$^2$, about 725 μg/m$^2$, about 750 μg/m$^2$, about 775 μg/m$^2$, about 800 μg/m$^2$, about 825 μg/m$^2$, about 850 μg/m$^2$, about 875 μg/m$^2$, about 900 μg/m$^2$, about 925 μg/m$^2$, about 950 μg/m$^2$, about 975 μg/m$^2$, about 1 mg/m$^2$, about 1 mg/m$^2$, about 1.5 mg/m$^2$, about 2.5 mg/m$^2$, about 3 mg/m$^2$, about 3.5 mg/m$^2$, about 4 mg/m$^2$, about 4.5 mg/m$^2$, about 5 mg/m$^2$, about 10 mg/m$^2$, about 15 mg/m$^2$, about 20 mg/m$^2$, about 25 mg/m$^2$, about 30 mg/m$^2$, about 35 mg/m$^2$, about 40 mg/m$^2$, about 45 mg/m$^2$, about 50 mg/m$^2$, about 60 mg/m$^2$, about 70 mg/m$^2$, about 80 mg/m$^2$, about 90 mg/m$^2$, about 100 mg/m$^2$, about 125 mg/m$^2$, about 150 mg/m$^2$, about 175 mg/m$^2$, about 200 mg/m$^2$ per unit dose, and one or more (e.g., 1, 2, 3, 4, 5, 6, 7, 8, 9, 10, 15 or 20) unit doses are administered weekly.

In certain embodiments, the IAP inhibitor and modulator of an immune checkpoint molecule or tubulin inhibitor are administered together, concurrently, sequentially or alternately. In certain embodiments, the IAP inhibitor, modulator of an immune checkpoint molecule, and tubulin inhibitor are administered together, concurrently, sequentially or alternately.

In certain embodiments, the IAP inhibitor is administered 1, 2, 3, 4, 5, 6, or 7 times every week. In some embodiments, the IAP is administered continuously for at least 1 week, at least 2 weeks, at least 3 weeks, at least 4 weeks, at least 5 weeks, at least 6 weeks, at least 7 weeks, or at least 8 weeks.

In certain embodiments, the modulator of an immune checkpoint molecule and/or tubulin inhibitor is administered 1, 2, 3, 4, 5, 6, or 7 times every week; 1, 2, 3, 4, 5, 6, or 7 times every 2 weeks; or 1, 2, 3, 4, 5, 6, or 7 times every 3 weeks. In some embodiments, the modulator of an immune checkpoint molecule and/or tubulin inhibitor is administered continuously for at least 1 week, at least 2 weeks, at least 3 weeks, at least 4 weeks, at least 5 weeks, at least 6 weeks, at least 7 weeks, or at least 8 weeks.

In certain embodiments, the IAP inhibitor, or modulator of an immune checkpoint molecule, and/or tubulin inhibitor is administered continuously for at least 3 days, at least 4 days, at least 5 days, at least 6 days, at least 7 days, at least 8 days, at least 9 days, at least 10 days, at least 11 days, at least 12 days, at least 13 days, at least 14 days, at least 15 days, at least 16 days, at least 17 days, at least 18 days, at least 19 days, at least 20 days, at least 21 days, at least 22 days, at least 23 days, at least 24 days, at least 25 days, at least 30 days, at least 35 days, at least 40 days, at least 45 days, or at least 50 days, at least 2 weeks, at least 2 weeks, at least 3 weeks, at least 4 weeks, at least 5 weeks, at least 6 weeks, at least 7 weeks, at least 8 weeks, at least 9 weeks, at least 10 weeks, at least 11 weeks, or at least 12 weeks.

In certain embodiments, the IAP inhibitor, or modulator of an immune checkpoint molecule, and/or tubulin inhibitor is administered for one or more (e.g., 1, 2, 3, 4, 5, 6, 7, 8, 9 or 10) courses of treatment, wherein each course of treatment lasts for at least 3 days, at least 4 days, at least 5 days, at least 6 days, at least 7 days, at least 8 days, at least 9 days, at least 10 days, at least 11 days, at least 12 days, at least 13 days, at least 14 days, at least 15 days, at least 16 days, at least 17 days, at least 18 days, at least 19 days, at least 20 days, at least 21 days, at least 22 days, at least 23 days, at least 24 days, at least 25 days, at least 30 days, at least 35 days, at least 40 days, at least 45 days or at least 50 days, at least 2 weeks, at least 2 weeks, at least 3 weeks, at least 4 weeks, at least 5 weeks, at least 6 weeks, at least 7 weeks, at least 8 weeks, at least 9 weeks, at least 10 weeks, at least 11 weeks, or at least 12 weeks; wherein for each course of treatment, administration is performed 1, 2, 3, 4, 5, 6, 7, 8, 9 or 10 times; and the interval between every two courses of treatment is 0, 1, 2, 3, 4, 5, 6, 7, 8, 9, 10 days, 2 weeks, 3 weeks, 4 weeks, 1 month or 2 months.

In a preferred embodiment, the amount of the IAP inhibitor, the modulator of an immune checkpoint molecule and/or the tubulin inhibitor administered for each course of treatment is the same or different when administered over a plurality of courses of treatment. In some embodiments, the amount of the IAP inhibitor, the modulator of an immune checkpoint molecule and/or tubulin inhibitor administered in a previous course of treatment is 1-10 times, preferably 1-5 times, such as 1.5, 2, 2.5, 3, 3.5, 4, 4.5 or 5 times, of the amount administered in a subsequent course of treatment.

In certain embodiments, the IAP inhibitor, the modulator of an immune checkpoint molecule and/or the tubulin inhibitor is administered by a same or different route of administration, including oral administration, intravenous injection or subcutaneous injection.

In certain embodiments, the modulator of an immune checkpoint molecule is administered in a lower amount than that administered when the modulator of an immune checkpoint molecule is administered alone or when the IAP inhibitor is not administered.

In certain embodiments, the tubulin inhibitor is administered in a lower amount than that administered when the tubulin inhibitor is administered alone or when the IAP inhibitor and/or the modulator of an immune checkpoint molecule is not administered.

In certain embodiments, the IAP inhibitor enhances the efficacy of the modulator of an immune checkpoint molecule and/or tubulin inhibitor in treating cancer and/or reduces the side effects of the modulator of an immune checkpoint molecule and/or tubulin inhibitor in treating cancer.

In certain embodiments, the modulator of an immune checkpoint molecule enhances the efficacy of the IAP inhibitor and/or tubulin inhibitor in treating cancer and/or reduces the side effects of the IAP inhibitor and/or tubulin inhibitor in treating cancer.

In certain embodiments, the tubulin inhibitor enhances the efficacy of the IAP inhibitor and/or modulator of an immune checkpoint molecule in treating cancer and/or reduces the side effects of the IAP inhibitor and/or modulator of an immune checkpoint molecule in treating cancer.

In certain embodiments, the cancer is an early stage cancer, a metaphase cancer or an advanced cancer. Preferably, the cancer is selected from adrenocortical cancer, anal cancer, cholangiocarcinoma, bladder cancer, bone cancer, bone metastasis cancer, adult brain/central nervous system tumor, childhood brain/central nervous system tumor, breast cancer, male breast cancer, childhood cancer, primary cancer unknown cancer, Castleman disease, Merkel cell carcinoma, cervical cancer, colon cancer, colorectal cancer, endometrial cancer, esophageal cancer, Ewing's sarcoma family tumor, eye cancer, gallbladder cancer, digestive tract cancer (such as gastric cancer), gastrointestinal stromal tumor (GIST), trophoblastic cancer, head and neck cancer, Kaposi's sarcoma, renal cancer, renal cell cancer, laryngeal and hypopharyngeal cancer, leukemia (such as acute lymphocytic leukemia (ALL), acute myelocytic leukemia (acute myeloid leukemia, AML), chronic lymphocytic leukemia (CLL), chronic granulocytic leukemia (CML), chronic myelomonocytic leukemia (CMML) or childhood leukemia), liver cancer (such as hepatocellular carcinoma), lung cancer (such as non-small cell lung cancer or small cell lung cancer), lymphoma, cutaneous lymphoma, malignant mesothelioma, multiple myeloma, myelodysplastic syndrome, nasal and nasalsinus cancer, nasopharyngeal cancer, neuroblastoma, Hodgkin's lymphoma, non-Hodgkin's lymphoma, childhood non-Hodgkin's lymphoma, oral and oropharyngeal cancer, osteosarcoma, ovarian cancer, pancreatic cancer, penile cancer, malignant pituitary tumor, prostate cancer, retinoblastoma, rhabdomyosarcoma, salivary gland cancer, sarcoma (such as adult soft tissue cancer or uterine sarcoma), skin cancer (such as basal and squamous cell cancer or melanoma), small intestinal cancer, testicular cancer, thymic cancer, thyroid cancer, vaginal cancer, vulvar cancer, Waldenstrom macroglobulinemia, Wilms tumor, urothelial cancer, microsatellite instability solid tumor (high or mismatch repair defect) and choriocarcinoma, and preferably, the cancer is head and neck cancer, microsatellite instability solid tumor, Hodgkin's lymphoma, non-Hodgkin's lymphoma, non-small cell lung cancer, renal cell cancer, bladder cancer, melanoma, squamous cell carcinoma, Merkel cell tumor, urothelial cancer or colorectal cancer.

In certain embodiments, the cancer is an advanced solid tumors or hematologic malignancies, and preferably, the cancer is metastatic pancreatic cancer, colorectal cancer, ovarian cancer, lymphoma, or liver cancer (such as hepatocellular carcinoma).

In certain embodiments, the individual suffers from an advanced cancer.

In certain embodiments, the individual suffers from a refractory cancer, a recurrent cancer or a resistant cancer, especially a cancer that is resistant to a cancer therapy comprising the modulator of an immune checkpoint molecule.

In certain embodiments, the individual suffers from a refractory cancer, a recurrent cancer or a resistant cancer, especially a cancer that is resistant to a cancer therapy comprising the modulator of an immune checkpoint molecule and/or tubulin inhibitor.

In certain embodiments, the individual suffers from a refractory cancer, a recurrent cancer or a resistant cancer, especially a cancer that is resistant to a cancer therapy comprising the IAP inhibitor and/or modulator of an immune checkpoint molecule.

In certain embodiments, the individual suffers from a refractory cancer, a recurrent cancer or a resistant cancer, especially a cancer that is resistant to a cancer therapy comprising the IAP inhibitor and/or tubulin inhibitor.

In certain embodiments, the present disclosure provides use of an IAP inhibitor in the manufacture of a medicament for use in combination with a modulator of an immune checkpoint molecule to treat an individual suffering from a resistant cancer, especially a cancer that is resistant to a cancer therapy comprising the modulator of an immune checkpoint molecule.

In certain embodiments, the present disclosure provides use of an IAP inhibitor in the manufacture of a medicament for use in combination with a modulator of an immune checkpoint molecule and tubulin inhibitor to treat an individual suffering from a resistant cancer, especially a cancer that is resistant to a cancer therapy comprising the modulator of an immune checkpoint molecule and/or tubulin inhibitor.

In certain embodiments, the present disclosure provides use of a modulator of an immune checkpoint molecule in the preparation of a medicament for use in combination with an IAP inhibitor to treat an individual suffering from a resistant cancer, especially a cancer that is resistant to a cancer therapy comprising the IAP inhibitor.

In certain embodiments, the present disclosure provides use of a modulator of an immune checkpoint molecule in the preparation of a medicament for use in combination with an IAP inhibitor and tubulin inhibitor to treat an individual suffering from a resistant cancer, especially a cancer that is resistant to a cancer therapy comprising the IAP inhibitor and/or tubulin inhibitor.

In certain embodiments, the present disclosure provides use of a tubulin inhibitor in the preparation of a medicament for use in combination with an IAP inhibitor and modulator of an immune checkpoint molecule to treat an individual suffering from a resistant cancer, especially a cancer that is resistant to a cancer therapy comprising the IAP inhibitor and/or modulator of an immune checkpoint molecule.

Pharmaceutical Composition and Kit

In another embodiment, the present disclosure provides a pharmaceutical composition comprising an IAP inhibitor, a modulator of an immune checkpoint molecule, and a pharmaceutically acceptable carrier.

In certain embodiments, the IAP inhibitor and the modulator of an immune checkpoint molecule are as defined above, respectively.

In another embodiment, the present disclosure provides a kit comprising:
 (a) a first component in a first container, the first component comprising an IAP inhibitor (preferably as defined above) and optionally a pharmaceutically acceptable carrier;

(b) a second component in a second container, the second component comprising a modulator of an immune checkpoint molecule (preferably as defined above) and optionally a pharmaceutically acceptable carrier; and (c) optionally an instruction.

In another embodiment, the present disclosure provides a pharmaceutical composition comprising an IAP inhibitor, a modulator of an immune checkpoint molecule, a tubulin inhibitor and a pharmaceutically acceptable carrier.

In certain embodiments, the IAP inhibitor, the modulator of an immune checkpoint molecule, and the tubulin inhibitor are as defined above, respectively.

In another embodiment, the present disclosure provides a kit comprising:

(a) a first component in a first container, the first component comprising an IAP inhibitor (preferably as defined above) and optionally a pharmaceutically acceptable carrier;

(b) a second component in a second container, the second component comprising a modulator of an immune checkpoint molecule (preferably as defined above) and optionally a pharmaceutically acceptable carrier;

(c) a second component in a third container, the third component comprising a tubulin inhibitor (preferably as defined above) and optionally a pharmaceutically acceptable carrier; and (d) optionally an instruction.

Treatment Methods: Single Agent or Combination Treatment

The present disclosure further provides methods of treating cancer in a patient in need thereof by administering to the patient an effective amount of IAP inhibitors (e.g., APG-115), either as a single agent or as a co-administered agent in a combination therapy with other therapeutic agents. In another embodiment, the present disclosure provides pharmaceutical compositions comprising a therapeutically effective amount of an IAP inhibitor disclosed herein, e.g., APG-1387 or a pharmaceutically acceptable salt thereof and a pharmaceutically acceptable carrier or diluent for the treatment of cancer.

In certain embodiments, the IAP inhibitor is an IAP inhibitor as described in WO2014/031487 which is incorporated herein by reference, and can be prepared by the method described therein.

In some embodiments, the IAP inhibitor is a compound of formula (I) or a pharmaceutically acceptable salt thereof. In some embodiments, the IAP inhibitor is APG-1387.

In one embodiment, the present disclosure provides a method for treating, suppressing, reducing the severity of, lowering the risk of, or inhibiting the metastasis of cancer in an individual, the method comprising administering to the individual a therapeutically effective amount of an IAP inhibitor as a single agent, or in combination with a therapeutically effective amount of a modulator of an immune checkpoint molecule.

In some certain embodiments, the IAP inhibitor (such as APG-1387) is administered in an amount of about 0.005 mg/day to about 5000 mg/day, such as about 0.005, 0.05, 0.5, 5, 10, 20, 30, 40, 50, 100, 150, 200, 250, 300, 350, 400, 450, 500, 550, 600, 650, 700, 750, 800, 850, 900, 950, 1000, 1500, 2000, 2500, 3000, 3500, 4000, 4500 or 5000 mg/day. In some embodiments, the IAP inhibitor is administrated in an amount of about 10 mg/week to about 200 mg/week, or about 20 mg/week to about 100 mg/week, or about 20 mg/week to about 80 mg/week, such as 10, 15, 20, 25, 30, 35, 40, 50, 55, 60, 65, 70, 75, 80, 85, 90, 95, 100, 110, 120, 130, 140, 150, 160, 170, 180, 190, or 200 mg/week.

In certain embodiments, the IAP inhibitor (such as APG-1387) is administered in an amount of about 1 ng/kg to about 200 mg/kg, about 1 µg/kg to about 100 mg/kg, or about 1 mg/kg to about 50 mg/kg per unit dose, such as administered in an amount of about 1 µg/kg, about 10 µg/kg, about 25 µg/kg, about 50 µg/kg, about 75 µg/kg, about 100 µg/kg, about 125 µg/kg, about 150 µg/kg, about 175 µg/kg, about 200 µg kg, about 225 µg/kg, about 250 µg kg, about 275 µg kg, about 300 µg/kg, about 325 µg kg, about 350 µg/kg, about 375 µg/kg, about 400 µg/kg, about 425 µg/kg, about 450 µg/kg, about 475 µg/kg, about 500 µg/kg, about 525 µg kg, about 550 µg/kg, about 575 µg kg, about 600 µg/kg, about 625 µg/kg, about 650 µg/kg, about 675 µg/kg, about 700 µg/kg, about 725 µg/kg, about 750 µg/kg, about 775 µg/kg, about 800 µg/kg, about 825 µg/kg, about 850 µg/kg, about 875 µg/kg, about 900 µg/kg, about 925 µg/kg, about 950 µg/kg, about 975 µg/kg, about 1 mg/kg, about 1.5 mg/kg, about 2.5 mg/kg, about 3 mg/kg, about 3.5 mg/kg, about 4 mg/kg, about 4.5 mg/kg, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 60 mg/kg, about 70 mg/kg, about 80 mg/kg, about 90 mg/kg, about 100 mg/kg, about 125 mg/kg, about 150 mg/kg, about 175 mg/kg, and about 200 mg/kg per unit dose, and one or more (e.g., 1, 2, 3, 4, 5, 6, 7, 8, 9 or 10) unit doses are administered daily or weekly.

In certain embodiments, the method for treating cancer comprising administering to a patient in need thereof a therapeutically effective amount of an IAP inhibitor, such as APG-1387, wherein the method comprises at least one 21-day treatment cycle, wherein an IAP inhibitor is administrated via an intravenous infusion on days 1, 8 and 15 day for the consecutive 3-weeks of the treatment cycle. This schedule is two weeks on and 1 week off for a cycle of 21 days (three weeks). The treatment cycles may be repeated as many times as needed. The therapeutically effective amount is from about 15 mg to about 100 mg of IAP inhibitor.

In certain embodiments, the cancer is advanced solid tumors or hematologic malignancies. In certain embodiments, the subject has advanced or metastatic solid tumor refractory to an existing therapy. In certain embodiments, the cancer is metastatic pancreatic cancer, colorectal cancer, ovarian cancer, lymphoma, or liver cancer (such as hepatocellular carcinoma).

In certain embodiments, therapeutically effective amount of IAP inhibitor is about 20 mg.

In certain embodiments, therapeutically effective amount of IAP inhibitor is about 30 mg.

In certain embodiments, therapeutically effective amount of IAP inhibitor is about 45 mg.

In certain embodiments, therapeutically effective amount of IAP inhibitor is about 60 mg.

In certain embodiments, therapeutically effective amount of IAP inhibitor is about 80 mg.

In certain embodiments, therapeutically effective amount of IAP inhibitor is from about 20 mg to 45 mg, from about 20 mg to 60 mg, or from about 20 mg to 80 mg.

Treatment: Advanced Solid Tumors or Hematologic Malignancies

In certain embodiments, an IAP inhibitor, such as APG-1387, is administered with one or more systemic anti-cancer agents in patients who are suffering from the advanced solid tumors or hematologic malignancies as a combination therapy.

In certain embodiments, the systemic anti-cancer agents are modulator of an immune checkpoint molecule or tubulin inhibitor.

In certain embodiments, the systemic anti-cancer agents are selected from pembrolizumab, paclitaxel, or carboplatin.

In certain embodiments, an IAP inhibitor may be combined with pembrolizumab, or paclitaxel and carboplatin for treating cancer in a patient in need thereof.

In certain embodiments, an IAP inhibitor may be combined with pembrolizumab for treating a patient in advanced solid tumors.

In certain embodiments, an IAP inhibitor may be combined with paclitaxel and carboplatin for treating a patient in advanced solid tumors.

In certain embodiments, an IAP inhibitor may be combined with paclitaxel and carboplatin for treating a patient in advanced ovarian carcinoma, pancreatic cancer, or colon cancer.

In the above embodiments, the IAP inhibitor is an IAP inhibitor as described in WO2014/031487 which is incorporated herein by reference, and can be prepared by the method described therein. In some embodiments, the IAP inhibitor is a compound of formula (I) or a pharmaceutically acceptable salt thereof. In the above embodiments, the IAP inhibitor is APG-1387.

In certain embodiments, commercially marketed formulations and the standard of care of pembrolizumab are adopted in the combination therapy.

In certain embodiments, pembrolizumab is administered as an intravenous infusion over 30 minutes every 3 weeks. In certain embodiments, pembrolizumab is administered at 200 mg to an adult patient, or weight based 2 mg/kg up to a maximum of 200 mg.

In certain embodiments, commercially marketed formulations and the standard of care of paclitaxel are adopted in the combination therapy. In certain embodiments, paclitaxel is administered intravenously over 3 hours every 3 weeks at a dose of 135 mg/m$^2$ or 175 mg/m$^2$. In another embodiment, patients will receive paclitaxel intravenously (IV) on day 1 of each 21-day treatment cycle after pre-medication to prevent severe hypersensitivity reactions.

Such premedication may comprise of dexamethasone 20 mg orally approximately 12 and 6 hours prior to paclitaxel being administered, diphenhydramine (or its equivalent) 50 mg IV 30 to 60 minutes prior to paclitaxel, and cimetidine (300 mg) or ranitidine (50 mg) IV 30-60 minutes prior to paclitaxel.

In certain embodiments, commercially marketed formulations and the standard of care of carboplatin are adopted in the combination therapy. In certain embodiments, carboplatin is administered intravenously by an infusion lasting 15 minutes or longer. In certain embodiments, patients will receive carboplatin 30 mg/m$^2$ on day 1 of each cycle. The dose may be adjusted or modified.

Method for Activating or Improving Antigen-Specific Immune Response

The present disclosure further provides a method for activating or improving antigen-specific immune response in individuals, the method comprising administering to the individual a therapeutically effective amount of an IAP inhibitor to activate or improve the individual's antigen-specific immune response.

In certain embodiments, the IAP inhibitor is an IAP inhibitor as described in WO2014/031487 which is incorporated herein by reference, and can be prepared by the method described therein. In certain embodiments, the IAP inhibitor is a compound of formula (I) or a pharmaceutically acceptable salt thereof. In some embodiments, the IAP inhibitor is APG-1387.

In certain embodiments, the antigen is disease antigen such as tumor antigen.

In certain embodiments, the antigen-specific immune response includes increasing the proportion of effector memory cells. In certain embodiments, the effector memory cells are effector memory T cells. In certain embodiments, the effector memory T cells express CD44 and CD3, but not CD62L (i.e. CD44$^+$CD62L$^-$CD3$^+$).

In certain embodiments, the effector memory cells comprise effector memory CD4$^+$ T cells, and/or effector memory CD8$^+$ T cells.

In certain embodiments, the antigen-specific immune response includes increasing the proportion of NK cells stimulated by antigen. In certain embodiments, the NK cells stimulated by antigen comprise NK cells in tumor tissue or infiltrated by tumor.

In certain embodiments, the antigen-specific immune response comprises increasing expression of a major histocompatibility complex (MEW) class II molecule (MHC-II) in an antigen presenting cell. Examples of antigen presenting cells include, but are not limited to, macrophages, B cells, dendritic cells, etc.

In certain embodiments, the activation or increase in the antigen-specific immune response is dependent upon IL-12. IL-12 is a cytokine derived from antigen-presenting cells, and can stimulate T cells and NK cells to secrete IFN-γ and enhance the proliferation and cytolytic activity of these cells (Gately et al, Annu Rev Immunol, 1998, Vol. 16, 495-521).

EXAMPLES

In order to make the objects and technical solutions of the present disclosure clearer, the present disclosure will be further illustrated below in conjunction with specific examples. It should be understood that these examples are used only for illustrating the present disclosure and are not for limiting its scope. Furthermore, specific experimental methods not mentioned in the following examples were carried out in accordance with conventional experimental methods.

The anti-PD-1 antibody used in the following examples was purchased from BioXcell, Item number BE0146, clone number: RMP1-14.

Example 1 Evaluation Method of In Vivo Pharmacodynamic Experiment

Cell inoculation method was used to establish a human tumor-immunized normal mouse subcutaneous homograft tumor model: tumor cells in logarithmic growth phase were collected, counted, and then resuspended in 1×PBS. The concentration of the cell suspension was adjusted to 2.5-5×10$^7$/mL. Tumor cells, 5-10×10$^6$/0.2 mL/mouse, were inoculated subcutaneously in the right back of the immunized normal mouse with a 1 mL syringe (4 gauge needle). All animal experimental operations were strictly in accordance with standards for use and management of laboratory animals by Gima Gene Co., Ltd and Suzhou Yasheng Pharmaceutical Co., Ltd. Relevant parameters were calculated with reference to China's NMPA "Guidelines for Non-clinical Research Techniques of Cytotoxic Antitumor Drugs".

Animal weight and tumor size were measured twice a week during the experiment. Animals were observed daily for status and the occurrence of death. Routine monitoring included the effects of tumor growth and treatment on the normal behaviors of animals, specifically including the activity, feeding and drinking, weight gain or loss, eyes, clothing hair, as well as other abnormalities of the laboratory animals. The deaths and clinical symptoms observed during the experiment were recorded in the original data. The whole process of administration, measurement of mouse weight and tumor volume was carried out in an ultra-clean bench. According to requirements of the experimental program, plasma and tumor tissue were collected, weighed and photographed for record after the end of last administration. Plasma and tumor samples were frozen at −80° C. for later use.

Tumor volume (TV) was calculated as TV=a×b²/2, wherein a and b represented the length and width of tumor measurement, respectively.

Relative tumor volume (RTV) was calculated as RTV=$V_t$/$V_1$, wherein $V_1$ was the tumor volume at the time of grouping administration, and $V_t$ was the tumor volume measured on day t after administration.

The evaluation index of anti-tumor activity was relative tumor proliferation rate T/C (%), and was calculated as: relative tumor proliferation rate T/C (%)=($T_{RTV}$/$C_{RTV}$)×100%, wherein $T_{RTV}$ was RTV in treatment group, and $C_{RTV}$ was RTV in vehicle control group.

Tumor remission rate (%) was the number of SD (stable disease), PR (partial regression) and CR (complete regression) in tumor-bearing mice after treatment divided by the total number of mice in that group×100%. CR refers to the complete regression of the tumor, which means the tumor is inaccessible after treatment. PR refers to the partial regression of the tumor, which means tumor volume becomes smaller than before treatment. SD refers to stable tumor progression, which means tumor volume is the same as before treatment.

Change of body weight (%)=(measurement of body weight−body weight when grouping)/body weight when grouping×100%.

Efficacy evaluation criteria: according to China's NMPA "Guidelines for Non-clinical Research Techniques of Cytotoxic Antitumor Drugs" (November 2006), T/C (%) value 40% and p<0.05 by statistical analysis were considered as efficacious. If the weight loss of mice exceeded 20%, or the drug-related death percentage exceeded 20%, the drug dose was considered to be severely toxic.

According to Clarke R., Issues in experimental design and endpoint analysis in the study of experimental cytotoxic agents in vivo in breast cancer and other models [J]. *Breast Cancer Research & Treatment*, 1997, 46(2-3):255-278, synergy analysis was evaluated by the following formula: synergistic factor=((A/C)×(B/C))/(AB/C); wherein A=RTV value in A drug monotherapy group; B=RTV value in B drug monotherapy group; C=RTV value in vehicle control group, and AB=RTV value in combination therapy group with A and B. Synergistic factor >1 indicated that a synergistic effect was achieved; synergistic factor=1 indicated that an additive effect was achieved; and synergistic factor <1 indicated that an antagonistic effect was achieved.

Synergistic Anti-Tumor Effect of APG-1387 with Anti-PD-1 Antibody (αPD-1) and Docetaxel in Homologous Mouse Tumor Model A tumor model of CT26 colorectal cancer mouse was established, and the combined anti-tumor effect of APG-1387 with anti-PD-1 antibody and docetaxel was evaluated on this model. The administration regimen was as follows:

APG-1387 monotherapy group: 0.2 mg/kg, intravenous injection, once daily for a total of 17 days;

Docetaxel monotherapy group: 8 mg/kg, intraperitoneal injection, once weekly for a total of 17 days;

Anti-PD-1 antibody monotherapy group: 200 μg/mouse, intraperitoneal injection, twice weekly for a total of 2.5 weeks (i.e., 17 days);

APG-1387+docetaxel combination group: (0.2 mg/kg, intravenous injection, once daily for a total of 17 days)+(8 mg/kg, intraperitoneal injection, once weekly for a total of 17 days);

APG-1387+anti-PD-1 antibody combination group: (0.2 mg/kg, intravenous injection, once daily for a total of 2.5 weeks)+(200 μg/mouse, intraperitoneal injection, twice weekly for a total of 2.5 weeks);

APG-1387+anti-PD-1 antibody+docetaxel combination group: (0.2 mg/kg, intravenous injection, once daily for a total of 2.5 weeks)+(200 μg/mouse, intraperitoneal injection, twice weekly for a total of 2.5 weeks)+(8 mg/kg, intraperitoneal injection, once weekly for a total of 2.5 weeks).

As shown in FIG. 1, on day 18 after administration, animals in 4 groups (including vehicle control group, APG-1387 monotherapy group (T/C=105%), docetaxel monotherapy group (T/C=66%), and APG-1387 plus docetaxel combination group (T/C=74%)) were euthanized due to large tumor burden. On day 18 after administration, T/C value in the APG-1387+anti-PD-1 antibody combination therapy group was 35%, and T/C value in the APG-1387+anti-PD-1 antibody+docetaxel combination therapy group was 28%.

Figure 2:
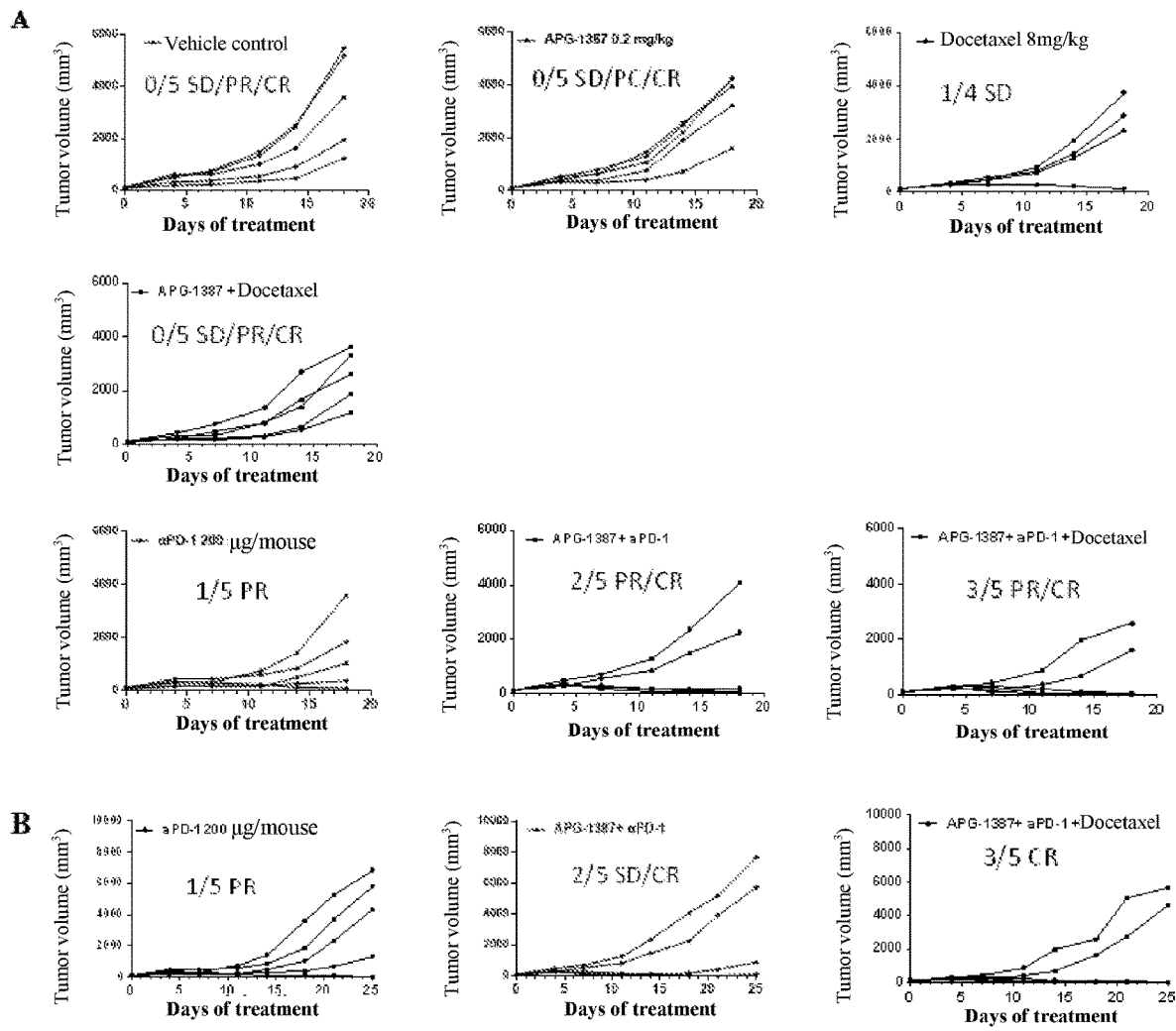
FIG. 2. Tumor growth curves for each mouse in each group and tumor response rates for each group on day 18 after administration (A) and day 25 after administration (B).

The tumor volume of individual animal in each group is as shown in FIG. 2. On day 18 after administration (FIG. 2A), no animals showed stable disease (SD), partial regression (PR) or complete regression (CR) in the vehicle group and APG-1387 monotherapy group. SD was obtained in one-fourth of the animals treated with docetaxel (¼; tumor remission rate was 25%). PR efficacy was obtained in ⅕ of the animals treated with anti-PD-1 antibody (tumor remission rate was 20%). Interestingly, by combination therapy with APG-1387 and anti-PD-1 antibody, ⅖ (tumor remission rate was 40%) of the animals showed PR or CR efficacy. Further, by combination therapy with three medicaments, 1 out of 5 animals could obtain PR efficacy, and 2 animals could obtain CR efficacy (tumor remission rate was 60%). On day 25 after administration (FIG. 2B), one of five animals in the anti-PD-1 treatment group maintained PR (20%) after an extended observation period without treatment. Two animals in the combination therapy group with APG-1387 and anti-PD-1 maintained SD or CR. However, three animals in the combination therapy group with three medicaments gradually obtained CR efficacy (tumor remission rate was 60%). The experimental data clearly showed that the combination of APG-1387 with anti-PD-1 antibody and docetaxel can effectively inhibit tumor with a higher remission rate, and obtain a more effective and lasting anti-tumor response compared with monotherapy with APG-1387 or anti-PD-1 antibody. These results showed that the combination of APG-1387 with anti-PD-1 antibody and docetaxel achieved a synergistic effect.

TABLE 1

Synergistic anti-tumor effect of combination therapy by APG-1387 with anti-PD-1 antibody and docetaxel in CT26 mouse colorectal cancer model

| | Treatment | T/C (%) value on day 18 after administration | Tumor remission rate on day 18 after administration (%) | Tumor remission rate on day 25 after administration (%) |
|---|---|---|---|---|
| 1 | Vehicle control group | — | 0/5 SD/PR/CR | / |
| 2 | APG-1387 | 105% | 0/5 SD/PR/CR | / |
| 3 | Docetaxel | 66% | 1/4 SD | / |
| 4 | APG-1387 + docetaxel | 74% | 0/5 SD/PR/CR | / |
| 5 | αPD-1 | 42% | 1/5 PR (20%) | 1/5 PR (20%) |
| 6 | APG-1387 + αPD-1 | 35% | 2/5 PR/CR (40%) | 2/5 SD/CR (40%) |
| 7 | APG-1387 + αPD-1 + docetaxel | 28% | 3/5 PR/CR (60%) | 3/5 CR (60%) |

Figure 3:
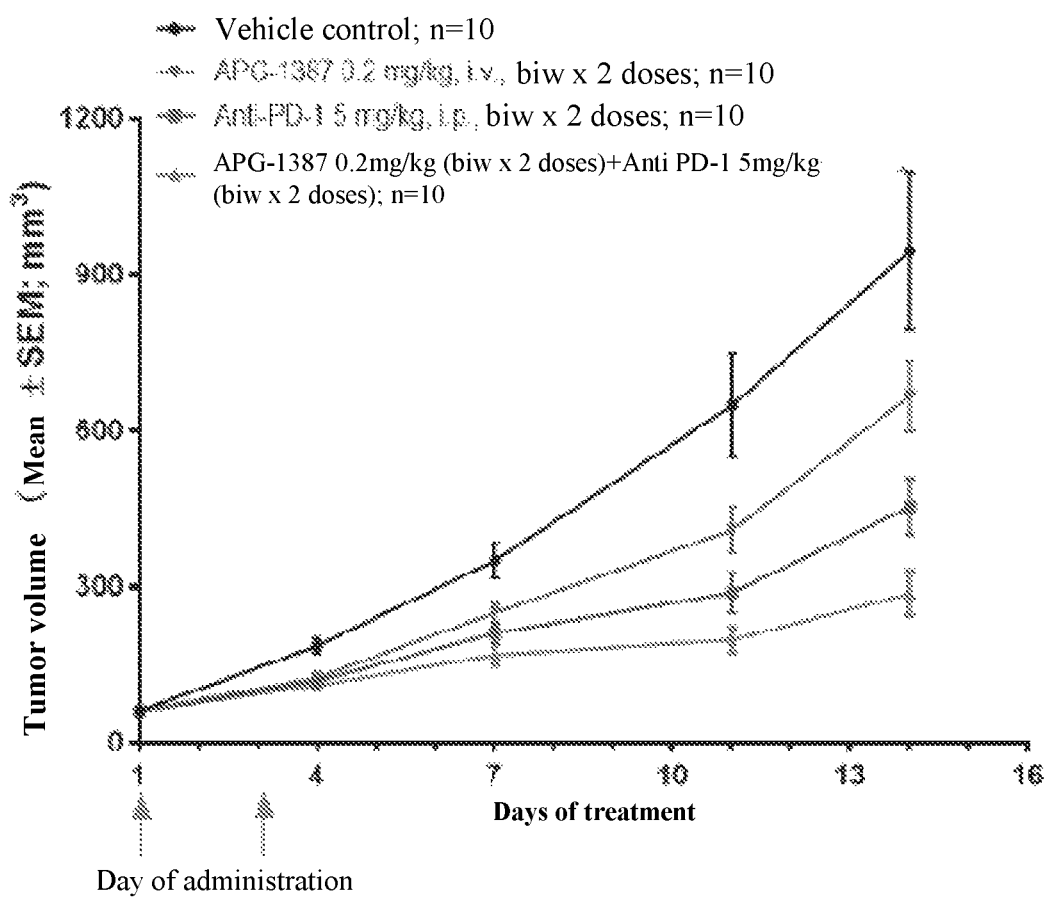
FIG. 3. Synergistic anti-tumor effect of combination therapy by APG-1387 with anti-PD-1 antibody in MC38 homologous mouse colon cancer model.

In accordance with operations similar to that described in example 1, a MC38 homologous mouse colon cancer model was established, and the effect of the combination of APG-1387 and anti-PD-1 antibody was tested according to the following administration regimen, with the results shown in FIG. 3.

Vehicle control group: vehicles for APG-1387 and anti-PD-1 antibody were administered for a total of 2 times;

APG-1387 monotherapy group: 0.2 mg/kg, intravenous injection, twice weekly for a total of 2 times;

Anti-PD-1 antibody monotherapy group: 5 mg/kg, intraperitoneal injection, twice weekly for a total of 2 times;

APG-1387+anti-PD-1 antibody combination group: (0.2 mg/kg, intravenous injection, twice weekly for a total of 2 times)+(5 mg/kg, intraperitoneal injection, twice weekly for a total of 2 times).

TABLE 2

Synergistic anti-tumor effect of combination therapy by APG-1387 with anti-PD-1 antibody in MC38 homologous mouse colon cancer model

| Treatment | RTV on day 14 after administration | T/C (%) value on day 14 after administration | Synergistic factor on day 14 after administration |
|---|---|---|---|
| Vehicle control | 15.6 ± 2.8 | — | — |
| APG-1387 | 11.0 ± 1.2 | 70 | — |
| αPD-1 | 7.4 ± 0.9 | 47 | — |
| APG-1387 + αPD-1 | 4.8 ± 0.8* | 31 | 1.09 |

Figure 4:
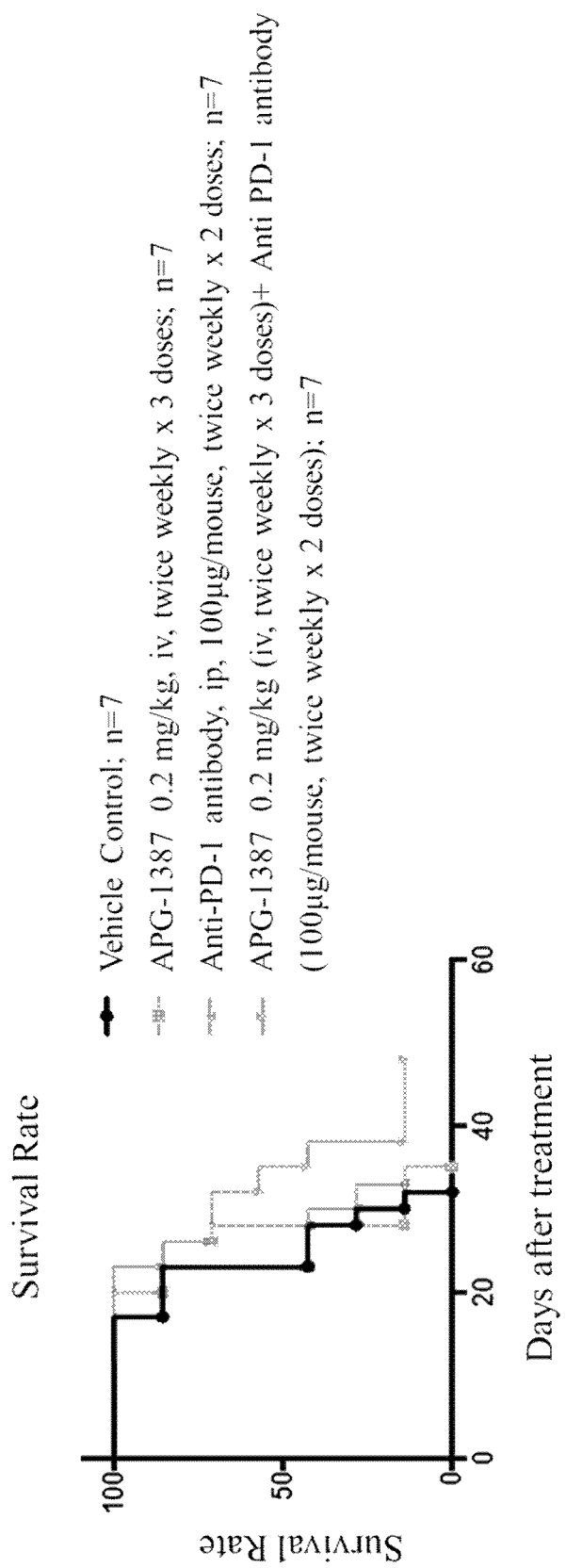
FIG. 4. Mouse survival rate-improving effect of combination therapy by APG-1387 with anti-PD-1 antibody in MC38 homologous mouse colon cancer model.

In accordance with operations similar to that described in example 1, a MC38 homologous mouse colon cancer model was established, and the mouse survival rate-improving effect of the combination of APG-1387 and anti-PD-1 antibody was tested according to the following administration regimen, with the results shown in FIG. 4.

Vehicle control group: vehicles for APG-1387 and anti-PD-1 antibody were administered for a total of 2 times;

APG-1387 monotherapy group: 0.2 mg/kg, intravenous injection, twice weekly for a total of 3 times;

Anti-PD-1 antibody monotherapy group: 100 μg/mouse, intraperitoneal injection, twice weekly for a total of 2 times;

APG-1387+anti-PD-1 antibody combination group: (0.2 mg/kg, intravenous injection, twice weekly, for a total of 3 times)+(100 μg/mouse, intraperitoneal injection, twice weekly, for a total of 2 times).

Example 2 APG-1387 Promoted the Proliferation of $CD4^+$T and $CD8^+$T Cells in In-Vitro Cell Tests (A) $CD4^+$ T cells or (B) $CD8^+$ T cells were positively sorted from mouse spleen using magnetic beads, and culture plates were coated with anti-CD3 antibodies of different concentrations (0.1, 1, 5, and 10 μg/ml). An additional 2 μg/ml of anti-CD28 was added for co-stimulation. After cells were treated with APG-1387 250 nM or DMSO for 72 hours, CellTiter-Glo Luminescent Cell Viability Assay (Promega) was used to determine the relative cell number, and it was normalized with DMSO-treated unstimulated cultures. Specifically, the 96-well plate and the CellTiter-Glo reagent were equilibrated at room temperature for 30 minutes, and 100 μL of CellTiter-Glo reagent was added to each well. After blending on a shaker for 2 minutes and leaving at room temperature for 10 minutes, the fluorescence values were read by Biotek synergy HIMF microplate reader. The average fluorescence value was calculated using 3 replicate wells, and the percentage of cell proliferation rate was calculated by the following formula: cell proliferation rate (%)=(fluorescence value of test well−negative control well)/(fluorescence value of solvent control group−negative control group)×100%. The results represented at least two independent tests.

Figure 5:
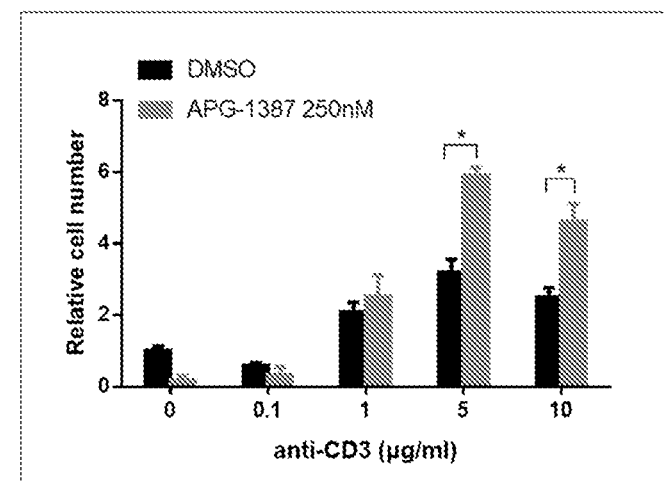
FIG. 5. APG-1387 promotes proliferation of CD4+ and CD8+ T cells
Figure 5:
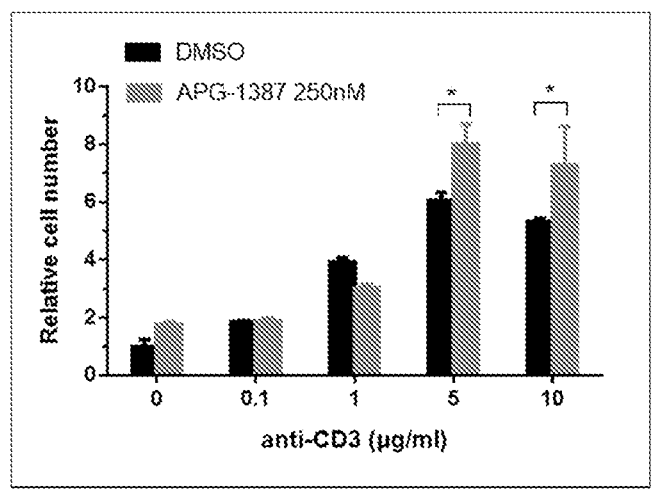

The results were as shown in FIG. 5. The in-vitro test results showed that APG-1387 could promote the proliferation of $CD4^+$ T and $CD8^+$ T cells stimulated by anti-CD3 and anti-CD28.

Example 3 Treating Patients with Advanced Solid Tumors or Hematologic Malignancies by Using APG-1387

Patients is treated over a 21-day treatment cycle. In the first treatment cycle, 20 mg of APG-1387 is administered via intravenous infusion on Days 1, 8 and 15. A standard "3+3" dose escalation is conducted to determine the MTD of APG-1387 by assessing the DLT of APG-1387 as a single agent. In Part 1, patients is treated over a 21-day cycle, wherein the treatment begins at 20 mg of APG-1387 and administered on Days, 1, 8, and 15. If no Dose Limiting Toxicity (DLT) is observed by the end of cycle 1 in the first 3 patients, the dose of APG-1387 will increase in subsequent cohorts to 30, 45, 60, and 80 mg accordingly. If ≥⅔ patients develop DLT at any dose level, dose escalation will cease and the next lower dose level will immediately be expanded to 6 patients. If ≤⅙ patients develop a DLT at the highest dose reached, this will be declared the Maximum Tolerated Dose (MTD). If no DLT has been reported, 80 mg of APG-1387 will be confirmed as MTD. Once MTD of the single agent is confirmed, the treatment will move to Part 2 as follows:

1. APG-1387 in combination with pembrolizumab in advanced solid tumors.
2. APG-1387 in combination with paclitaxel and carboplatin in advanced ovarian carcinoma.
3. APG-1387 in combination with paclitaxel and carboplatin in advanced solid tumors except ovarian carcinoma After the MTD/RP2D of APG-1387 in combination with pembrolizumab, or paclitaxel and carboplatin is determined, a maximum of 20 patients will be treated with the combination at that dose level until disease progression, unacceptable toxicity, or another discontinuation criterion is met. Stable or responding patients who experience DLTs may continue therapy once DLTs have resolved to <Grade 1 base on the discussion between the investigator and the sponsor. Intra-patient dose escalation will be allowed.

In a single agent treatment method, APG-1387 for injection will be supplied as a sterile lyophilized power, 10 mg per vial. APG-1387 will be administered via intravenous infusion after reconstitution as follows: 2 mL of Water for Injection should be introduced into the vial to dissolve the powder, then further diluted with 5% glucose solution for injection.

In combination treatment methods, commercially marked formulations are used. Patients will receive pembrolizumab 200 mg intravenous over 30 minutes every three week. Patients will receive intravenous paclitaxel standard of care intravenous (IV), once on day 1 of each 21-day treatment cycle, after pre-medication to prevent severe hypersensitivity reactions.

Patient will receive carboplatin standard of care, intravenous (IV), once on day 1 of each 21-day treatment cycle.

Example 4 Safety and Tolerability of APG-1387 as a Single Agent or in Combination with Pembrolizumab APG-1387 is a novel, bivalent small molecule IAP (inhibitor of apoptosis proteins) inhibitor. APG-1387 is a SMAC mimetic which can antagonize the function of cIAP1/2 or XIAP, which triggers caspase activation and leads to apoptosis. APG-1387 has shown strong antitumor activities in multiple human xenograft cancer models. APG-1387 also acts as host immune modulator, supporting the notion that APG-1387 in combination with anti-PD1 antibody for cancer therapy.

A Phase I study ((NCT03386526) was conducted to assess the safety and tolerability of APG-1387 as a single agent (Part 1) or in combination with pembrolizumab (Part 2).

The primary objective of the study was to assess the safety and tolerability of APG-1387 as a single agent or in combination with pembrolizumab. The second objective was to determine the pharmacokinetics (PK), pharmacodynamics (PD), anti-tumor effects of APG-1387 as a single agent or in combination with pembrolizumab.

The Phase I dose escalation study included two parts. Part 1 is a "3+3" dose escalation of APG-1387, including a mPC (metastatic pancreatic cancer) cohort expansion. Part 2 is a "3+3" dose escalation and cohort expansion of APG-1387 in combination with pembrolizumab.

APG-1387 was IV administered for 30 minutes once weekly in a 21-day-cycle. Pembrolizumab was administered 200 mg IV on day 1 of a 21-day-cycle, until disease progression or untolerated toxicity. APG-1387 in $K_2EDTA$ human plasma was determined using an LC-MS/MS method using APG-1387-d10 as the internal standard (IS). APG-1387 and the IS were extracted by protein precipitation from human plasma using methanol. Reversed-phase HPLC separation was achieved with an Agilent Polaris 5, C18-A, column (50×2.0 mm, 5 micron). MS/MS detection was set at mass transitions of m/z 579.4→167.2 for APG-1387 and m/z 584.4→172.1 for APG-1387-d10 (IS) in TIS positive mode.

The inclusion criteria for the Phase I study are: Age≥18 years; ECOG PS: 0-1;

Adequate hematologic, renal and liver functions; Advanced or metastatic solid tumor patients must be refractory to or intolerant of existing therapy(ies) known to provide clinical benefit for their condition.

The exclusion criteria are: received chemotherapy, hormonal and biologic (<2 half-lives), small molecule targeted therapies or other anti-cancer therapy within 21 days prior to entering the study; neurologic instability per clinical evaluation due to tumor involvement of the central nervous system (CNS); or uncontrolled concurrent illness.

The patients enrolled showed the baseline characteristics as shown in Tables 3(a) and 3(b).

Table 3. Patient Demographics and Characteristics at Baseline

TABLE 3 (a)

| Characteristic, n(%) | APG-1387 Mono (N = 24) | APG-1387 + Pembrolizumab (N = 5) |
|---|---|---|
| Age, median (range) | 66.5 | 61.0 |
|  | (48; 88) | (35; 78) |
| Male sex | 11 | 2 |
|  | (45.8%) | (40.0%) |
| ECOG PS |  |  |
| 0 | 10 | 1 |
| 1 | 14 | 4 |
| Prior systemic cancer therapies(1-11) |  |  |
| 1 | 1 | 0 |
| 2-5 | 20 | 4 |
| ≥6 | 3 | 1 |

TABLE 3 (b)

| Primary Cancer, n(%) | APG-1387 Mono (N = 24) | APG-1387 + Pembrolizumab (N = 5) |
|---|---|---|
| Breast Cancer | 1 (4.2%) | 1 (20.0%) |
| Cholangiocarciboma | 0 | 1 (20.0%) |
| ColonCancer | 5 (20.9%) | 0 |
| Leiomysarcoma | 1 (4.2%) | 0 |
| Lung Cancer | 2 (8.3%) | 0 |
| Lung, Squamous Cell Cancer | 1 (4.2%) | 0 |
| Non Small Cell Lung Carcinoma | 1 (4.2%) | 0 |
| Melanoma | 2 (8.3%) | 1 (20.0%) |
| Pancreatic Cancer | 10 (41.6%) | 1 (20.0%) |
| Prostate Cancer | 1 (4.2%) | 1 (20.0%) |

The tolerability results of the patients after drug administration is shown in Table 3(c) and 3(d).

TABLE 3 (c)

| Patient disposition (by dose level) | APG-1387 Monotherapy | | | | | APG-1387 + Pembrolizumab | | |
|---|---|---|---|---|---|---|---|---|
| | 20 mg (n = 3) | 30 mg (n = 3) | 45 mg (n = 13) | 60 mg (n = 5) | Overall (n = 24) | 20 mg (n = 4) | 30 mg (n = 1) | Overall (n = 5) |
| # of pts completed the 1# cycle treatment | 3 | 3 | 12 | 4 | 22 | 4 | 1 | 5 |
| # of pts discontinued treatment | 3 | 3 | 11 | 5 | 22 | 3 | — | 3 |
| Adverse Event | 0 | 0 | 1 | 2 | 3 | 0 | — | 0 |
| Disease progression | 2 | 3 | 8 | 1 | 14 | 2 | — | 2 |
| Clinical progression | 0 | 0 | 1 | 1 | 2 | 0 | — | 0 |
| Lack of efficacy | 1 | 0 | 1 | 0 | 2 | 0 | — | 0 |
| Subject withdrawal | 0 | 0 | 0 | 1 | 1 | 1 | — | 1 |

Treatment Related Adverse Events (all Grades)

TABLE 3 (d)

| | APG-1387 Monotherapy | | | | | APG-1387 + Pembrolizumab | | |
|---|---|---|---|---|---|---|---|---|
| | 20 mg (n = 3) | 30 mg (n = 3) | 45 mg (n = 13) | 60 mg (n = 5) | Overall (n = 24) | 20 mg (n = 4) | 30 mg (n = 1) | Overall (n =5 ) |
| Fatigue | 0 | 0 | 3 (23.1%) | 0 | 3 (12.5%) | 2 (50.0%) | 0 | 2 (40.0%) |
| Headache | 0 | 1 (33.3%) | 0 | 1 (20.0%) | 2 (8.3%) | 1 (25.0%) | 1 (100.0%) | 2 (40.0%) |
| Decreased appetite | 0 | 0 | 2 (15.4%) | 0 | 2 (8.3%) | 1 (25.0%) | 0 | 1 (20.0%) |
| Myalgia | 0 | 0 | 1 (7.7%) | 0 | 1 (4.2%) | 1 (25.0%) | 0 | 1 (20.0%) |
| Nausea | 0 | 1 (33.3%) | 1 (7.7%) | 0 | 2 (8.3%) | 0 | 0 | 0 |
| Pruritus | 1 (33.3%) | 0 | 0 | 1 (20.0%) | 2 (8.3%) | 0 | 0 | 0 |
| Rash maculo-papular | 1 (33.3%) | 0 | 0 | 1 (20.0%) | 2 (8.3%) | 0 | 0 | 0 |
| Aspartate aminotransferase increased | 0 | 0 | 1 (7.7%) | 0 | 1 (4.2%) | 0 | 0 | 0 |
| Blood bilirubin increased | 0 | 0 | 0 | 1 (20.0%) | 1 (4.2%) | 0 | 0 | 0 |
| Dehydration | 0 | 0 | 1 (7.7%) | 0 | 1 (4.2%) | 0 | 0 | 0 |
| Diarrhoea | 0 | 1 (33.3%) | 0 | 0 | 1 (4.2%) | 0 | 0 | 0 |
| Dyspepsia | 0 | 0 | 1 (7.7%) | 0 | 1 (4.2%) | 0 | 0 | 0 |
| Eructation | 0 | 0 | 0 | 0 | 0 | 1 (25.0%) | 0 | 1 (20.0%) |
| Bell's palsy | 0 | 0 | 1 (7.7%) | 1 (20.0%) | 2 (8.4%) | 0 | 0 | 0 |
| Lipase increased | 0 | 0 | 0 | 1 (20.0%) | 1 (4.2%) | 0 | 0 | 0 |
| Peripheral sensory neuropathy | 0 | 0 | 1 (7.7%) | 0 | 1 (4.2%) | 0 | 0 | 0 |
| Phlebitis | 1 (33.3%) | 0 | 0 | 0 | 1 (4.2%) | 0 | 0 | 0 |

TABLE 3 (d)-continued

|  | APG-1387 Monotherapy | | | | | APG-1387 + Pembrolizumab | | |
| --- | --- | --- | --- | --- | --- | --- | --- | --- |
|  | 20 mg (n = 3) | 30 mg (n = 3) | 45 mg (n = 13) | 60 mg (n = 5) | Overall (n = 24) | 20 mg (n = 4) | 30 mg (n = 1) | Overall (n =5) |
| Pneumonitis | 0 | 0 | 0 | 1 (20.0%) | 1 (4.2%) | 0 | 0 | 0 |
| Tumor pain | 0 | 0 | 0 | 0 | 0 | 1 (25.0%) | 0 | 1 (20.0%) |

G3 above TRAEs: one G3 blood bilirubin increased; one lipase increased, both in 60 mg monotherapy.

Till Apr. 19, 2019, 24 patients had been treated with APG-1387 and 5 patients had been treated with APG-1387 plus pembrolizumab. APG-1387 was well tolerated and had manageable adverse events. Most common treatment-related adverse events (TRAEs) (>10%) are fatigue. Two Dose Limiting Toxicity (DLTs) were observed at 60 mg including lipase increase and facial nerve disorder, MTD of APG-1387 monotherapy was determined as 45 mg.

The preliminary anti-tumor activity observed during the study was characterized in Table 4 and Table 5.

TABLE 4

Anti-tumor activity in all tumor types

| Response | APG-1387 (N = 24) | APG-1387 + Pembrolizumab (N = 5) |
| --- | --- | --- |
| ORR (objective response rate, CR + PR) | 0 | 0 |
| DCR (disease control rate, SD above) | 6/24 | 0 |
| Best response | | |
| CR | 0 | 0 |
| PR | 0 | 0 |
| SD | 6 | 0 |
| PD | 15 | 2 |
| Not assessed | 3 | 2 |

TABLE 5

Anti-tumor activity in pancreatic cancer

| Response | APG-1387 (N = 10) | APG-1387 + Pembrolizumab (N = 1) |
| --- | --- | --- |
| ORR (objective response rate, CR + PR) | 0 | 0 |
| DCR (disease control rate, SD above) | 4/10 | 0 |
| Best response | | |
| CR | 0 | 0 |
| PR | 0 | 0 |
| SD | 4 | 0 |
| PD | 4 | 0 |
| Not assessed | 2 | 1 |

Figure 6:
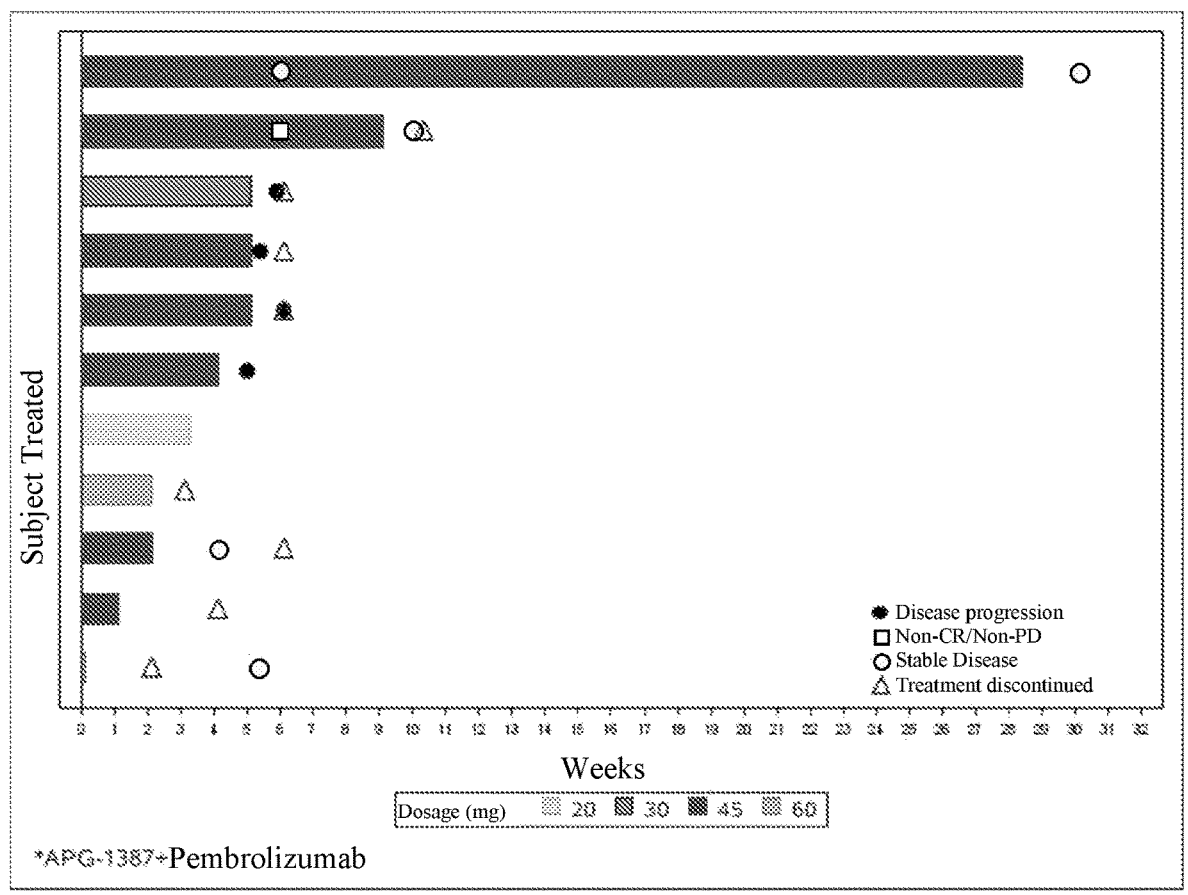
FIG. 6. Treatment duration and response in pancreatic cancer.
Figure 7:
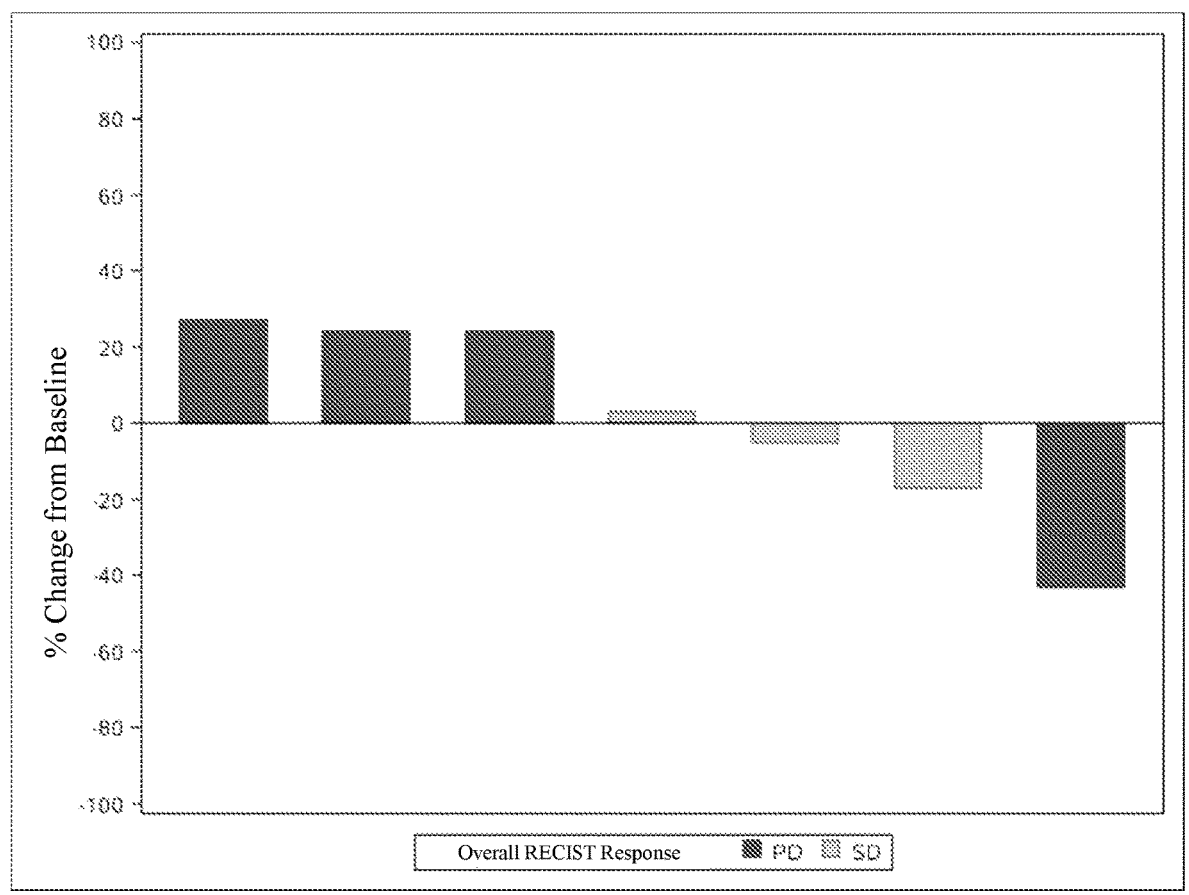
FIG. 7. Best percentage change from baseline in target lesion of pancreatic cancer.

Four out of 10 mPC (metastatic pancreatic cancer) patients in APG-1387 monotherapy (one at 60 mg, three at 45 mg) achieved stable disease (SD), one of them at 45 mg has been treated >9 cycles (more than 6 months) with confirmed SD (+6%). See FIG. 6. See also FIG. 7, which shows the best percent change from baseline in target lesions of pancreatic cancer.

Figure 8:
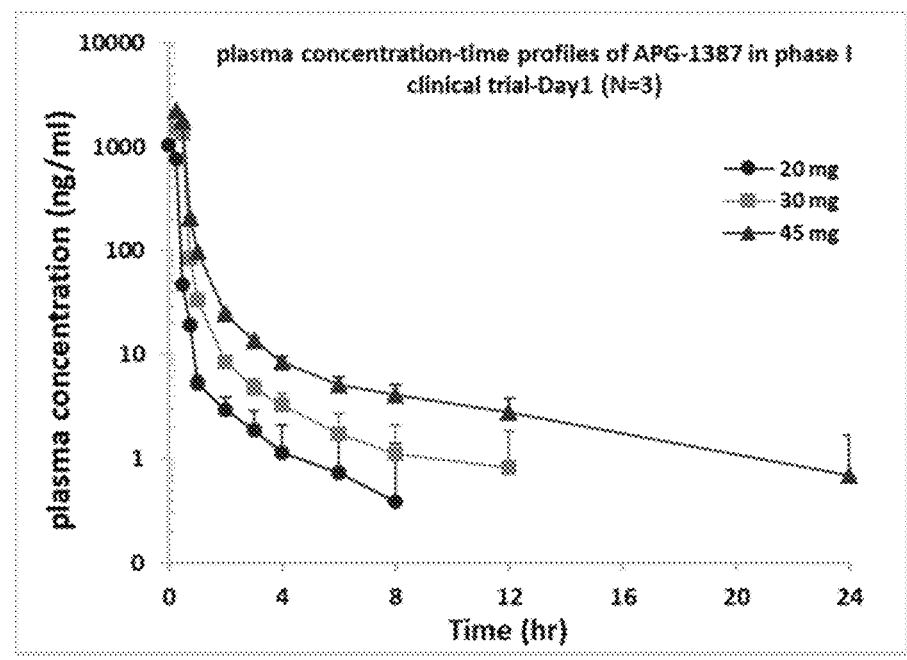
FIG. 8. APG-1387 pharmacokinetics in plasma.
Figure 8:
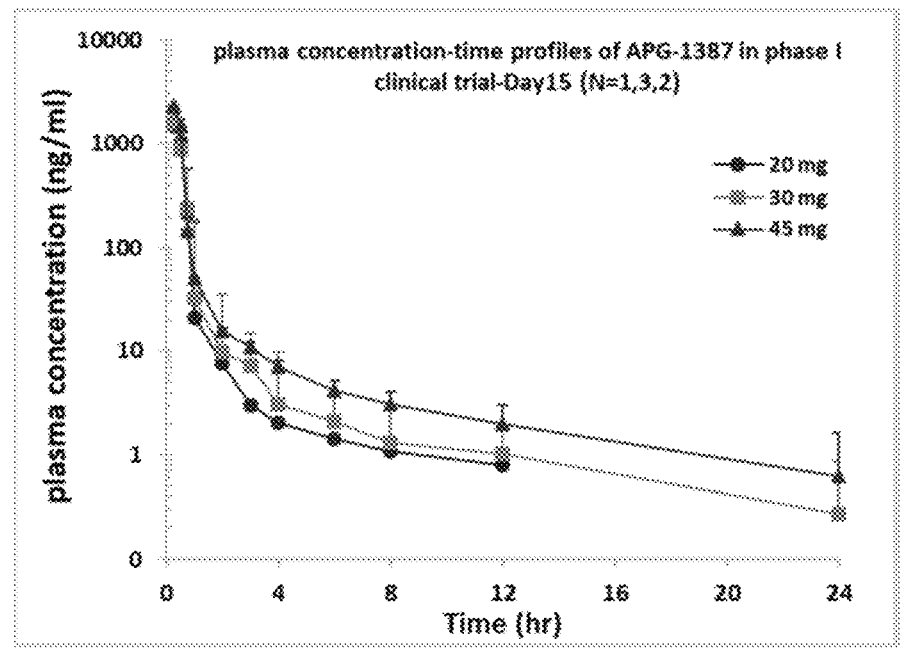

Preliminary PK data of APG-1387 (see FIGS. 8(A) and 8(B)) showed increase in AUC and Cmax was approximately dose proportional over the range of 20 to 45 mg, and there are no significant accumulation was observed with weekly dosing regimen.

Figure 9:
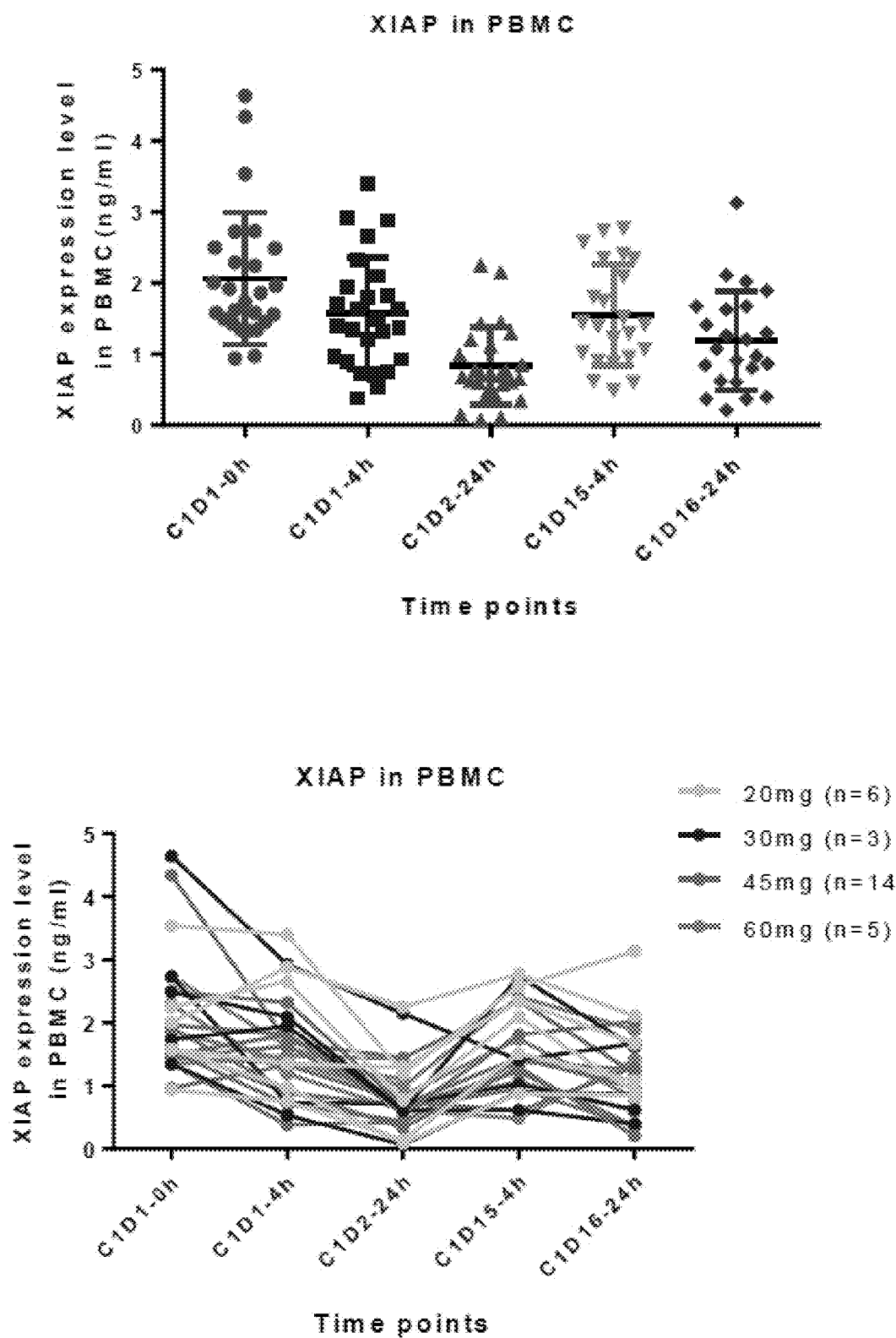
FIG. 9. XIAP suppression after APG-1387 treatment.
Figure 10:
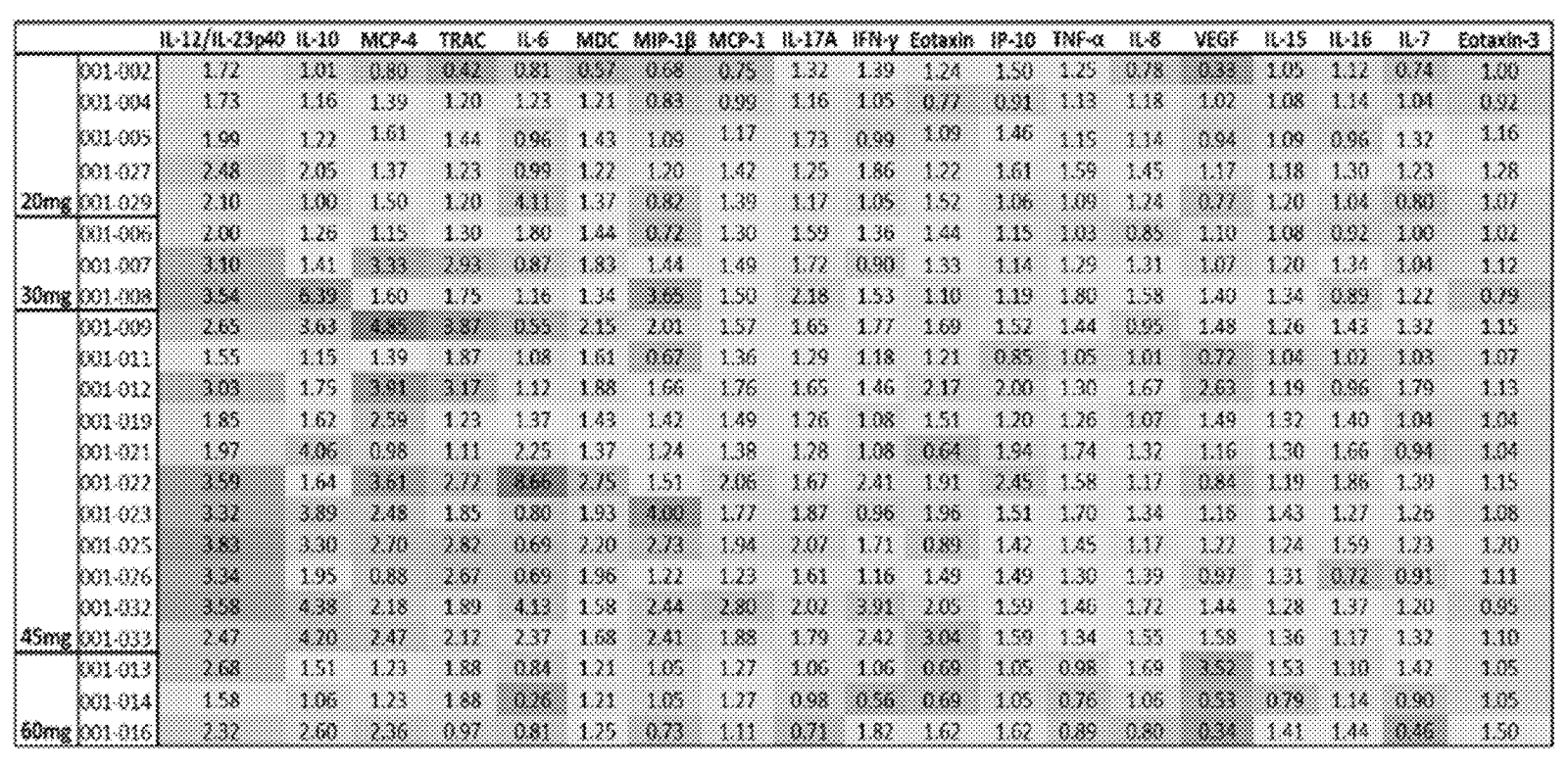

APG-1387 treatment induced significantly XIAP suppression in PBMCs (see FIGS. 9 (a) and 9(b)) and cytokine releasing in serum (see FIG. 10), suggesting a potential mechanistic PD relationship and immunomodulation.

Example 5 Antitumor Effect of APG-1387 in Combination with Anti-PD-1 Antibody in in Vivo Experiments Test Articles (1) APG-1387: provided by Jiangsu Ascentage Pharmaceutical Development Co., Ltd. The batch number is R12JA076140-A2 and PAPG-1387-DP-201305A. Preserved at 4° C., away from the light and sealed. APG-1387 was administered intravenously (i.v.) or intraperitoneally (i.p.) or at a dosage of 10 mL/kg. APG-1387 was dissolved in 5% castor oil/10% PEG400/85% normal saline.

(2) Anti-PD-1 antibody: purchased from BioXcell. The article number is BE0146 and BE0273. Preserved at 4° C. and sealed. The anti-PD-1 antibody was administered intraperitoneally at a concentration of 100 μg per mice or 200 μg per mice.

(3) Isotype control (anti-IgG): purchased from BioXcell, the product number is BE0089. Preserved at 4° C. and sealed. The isotype control was administered intraperitoneally at a concentration of 100 μg per mice or 200 μg per mice.

(4) Docetaxel: purchased from Nanjing Aikang Chemical Co., Ltd. The batch number is 20141024. Preserved at 4° C. and sealed. Docetaxel was administered intravenously at a volume of 10 mL/kg.

(5) Anti-IL-12 antibody: purchased from BioXcell. The article number is BE0051. Preserved at 4° C. and sealed. The anti-IL-12 antibody was administered intraperitoneally at a concentration of 500 μg per mice.

Cell Line

Murine MC38 colon cancer cells, murine A20 lymphoma cells, and human PLC/PRF/5 liver cancer cells were purchased from American Type Culture Collection (ATCC). Murine ID8-Luc ovarian cancer cells were kindly gifted by Professor Xie Dan's laboratory from Sun Yat-Sen University.

Experiment Design

The mice were injected subcutaneously with 0.5-10×10⁶ cells or in the ovary with 6×10⁶ cells in situ to build the tumor xenograft model. Tumor-bearing mice were randomly assigned into different drug administering groups. Under sterile conditions, the tumor xenograft model was built by injecting tumor cells into the right back hypodermis or into the orthotopic ovary (ID8-Luc) of mice with normal immune systems. For the orthotopic model, tumor growth was measured by examining in vivo fluorescence images 10 days after inoculation. Mice were randomized into different groups and treatment begun. For the subcutaneous tumor xenograft model, when the tumors reach the appropriate size (50-150 mm$^3$), animals are randomly assigned groups based on tumor size. The difference in volume between each group should be less than 10% of the mean. There are 5 to 10 animals per group. Drug administration starts on the day when groups were assigned (i.e. D1). For the A20 in subcutaneous model, mice were grouped based on body weight and drug administration began on the same day (i.e. D1). Body weight and tumor size were measured twice per week during the experiment. Daily observations were made to record clinical symptoms.

The calculation of tumor related parameters is the same as set forth in Example 1. Using the fluorescence imaging technique, the strength of the fluorescent signal can represent the growth and metastasis of tumors in vivo. For observations of survival rates, when the tumor volume of the tumor-bearing animal is ≥2,000 mm$^3$, the animal should be euthanized and is considered to have had a tumor-caused natural death.

In the experiment of tumor-infiltrated lymphocyte analysis, tissue samples such as spleen, draining lymph node, ascites, tumor or other tissues were collected 24 hours after the last drug administration. A single cell suspension of the spleen and draining lymph nodes was obtained, and the red blood cells were lysed after centrifugation, and the cells were filtered, followed by flow cytometric staining and flow cytometry. The tumor tissue was cut and centrifuged, and the tissue was digested, the cells were filtered. Ficoll was used to separate individual nuclei. Individual nuclei were collected for corresponding antibody flow staining and flow cytometry Ascites samples were collected and centrifuged, and the cells were filtered and subjected to flow cytometry staining and flow cytometry.

Statistical Analysis

The tumor growth curve and the animal body weight curve were plotted, with time on the X-axis and tumor volume and animal body weight on the Y-axis. Experimental data is expressed as mean±standard error of mean (SEM), where SEM=standard deviation/square root of (n) and n=number of animals in the experimental group. The difference between two groups were analyzed using the Mann-Whitney U statistical method. Differences between means of multiple groups were analyzed by using one-way analysis of variance and statistically compared using the Games-Howell method. Survival curves were compared using the log-rank statistical method and multiple tests were being performed. All data were analyzed using SPSS 18.0 (*P<0.05, P<0.01, *P<0.001, ****P<0.0001).

Antitumor Effect of APG-1387 Combined with Anti-PD-1 Antibody in the Subcutaneous Xenograft Model of Mice with Murine MC38 Colon Cancer In cell experiments, treatment with APG-1387 in vitro can stimulate M38 cells to secret IFN-γ, IL-5, IL-12p70, etc., that increases the proliferation of T cell and other inflammatory cytokines. In this study, MC38 cells were selected and subcutaneously inoculated into the right back of female C57BL/6 mice with 0.5-10×10$^6$ cells/mouse to establish a subcutaneous xenograft model of mice with normal immune system to evaluate the anti-tumor effect of APG-1387 in combination with anti-PD-1 antibody. See Table 6 for the specific dosing regimen.

TABLE 6

Study design

| Group | Animal Number | Treatment | Dose | Route of Administration | Dosing Regimen |
|---|---|---|---|---|---|
| 1 | 9 | APG-1387 vehicle | — | i.v. | q3d × 2 doses |
|   |   | isotype control | 100 μg/mouse | i.p. | q3d × 2 doses |
| 2 | 7 | APG-1387 | 0.2 mg/kg | i.v. | q3d × 2 doses |
| 3 | 8 | Anti-PD-1-antibody | 100 μg/mouse | i.p. | q3d × 2 doses |
| 4 | 8 | APG-1387 | 0.2 mg/kg | i.v. | q3d × 2 doses |
|   |   | Anti-PD-1-antibody | 100 μg/mouse | i.p. | q3d × 2 doses |

Figure 11:
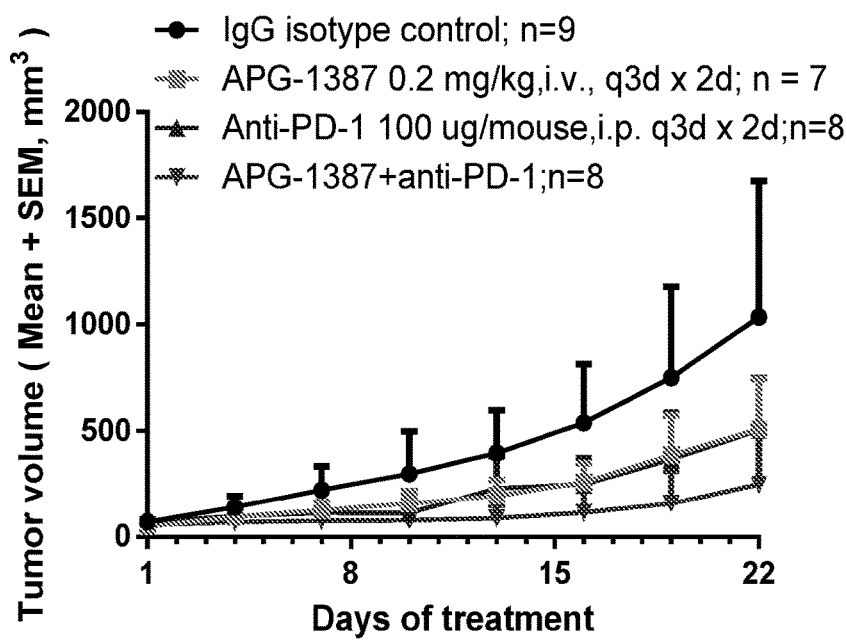
FIG. 11. The combination of APG-1387 and anti-PD-1 antibody significantly inhibited tumor growth in the mice bearing murine MC38 subcutaneous tumor xenograft (FIG. 11A, 11B) and significantly prolonged the survival of mice (FIG. 11C, 11D).
Figure 11:
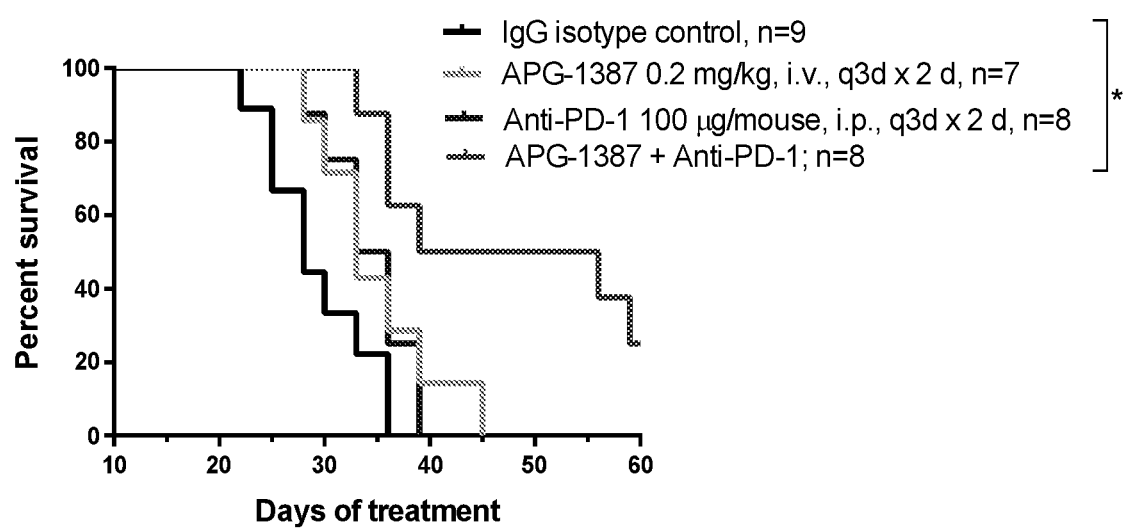

The results are shown in FIGS. 11A and 11B. On the 22nd day after administration, the APG-1387 alone or combined with anti-PD-1 antibody both have certain anti-tumor effects. The T/C values were 69.6% and 48.6%, respectively, and the values are statistically significant compared to the isotype control group (P<0.05). Anti-tumor effect was significantly enhanced through the combination of APG-1387 and anti-PD-1 antibody. The T/C value reached 30.6%, which is proven to be statistically significant compared to the isotype control group (P<0.0001). The combination treatment between APG-1387 and anti-PD-1 antibody also showed a statistically significant difference compared to the control group (P<0.05) and the results of the synergy analysis showed that the combination of the two drugs had a synergistic anti-tumor effect with a synergy score of 1.10. As shown in FIGS. 11C, 11D, the median survival time of the animals in treatment group was 28.0 days. The APG-1387 single-agent group and the anti-PD-1 antibody single-agent group can prolong the median survival time of the animals to a certain extent. The median survival times were 33.0 days and 34.5 days, respectively. The combination of APG-1387 and anti-PD-1 antibody further prolonged the survival time of mice, with a median survival of 47.5 days (P<0.05, compared to the control group). Animals in each treatment group showed no significant weight loss.

The above results indicate that the combination of APG-1387 and anti-PD-1 antibody had a significant anti-tumor effect that was superior to single-agent treatments.

Antitumor Effect of APG-1387 Combined with Anti-PD-1 Antibody in the Orthotropic Ovarian Xenograft Model of Mice with Murine ID8-Luc Ovarian Cancer Ovarian cancer is the world's deadliest gynecological malignancy and the second most common gynecological cancer. Current chemotherapeutic drugs are only transiently effective. The rate of metastasis and recurrence remains high. Although the most promising immunotherapy currently has great clinical success in various tumor treatments, the implementation of immunotherapy in ovarian cancer remains a major challenge. Previous studies in this field has found that APG-1387 can increase apoptosis and autophagy in ovarian cancer cells (Li et al., J Exp Clin Cancer Res 37, 53.). Therefore, ID8-Luc cells were selected in this study, and 6×10⁶ cells/mouse were inoculated into the ovary of female C57BL/6 mice to establish a mouse orthotopic transplantation tumor model to evaluate the anti-tumor effect of APG-1387 combined with anti-PD-1 antibody. The specific dosing regimen is shown in Table 7.

Figure 12:
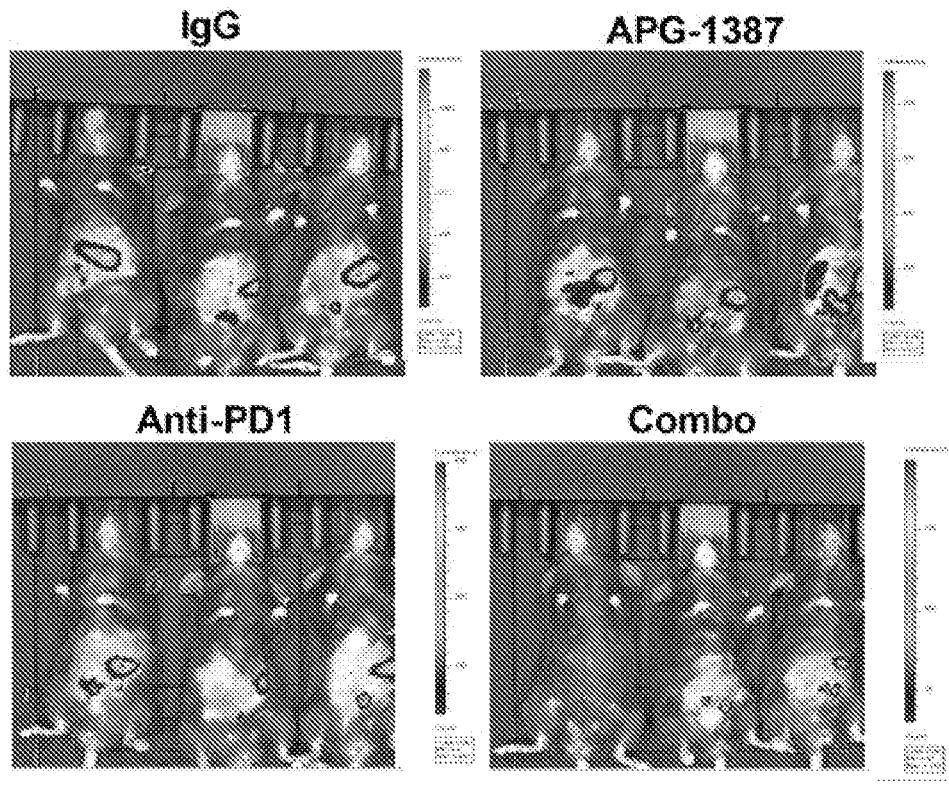
FIG. 12. APG-1387 in combination with anti-PD-1 antibody significantly inhibited tumor growth in mice bearing murine ID8-Luc orthotropic tumor xenograft (FIG. 12A, 12B) and significantly prolonged the survival of mice ((FIG. 12C, 12D).
Figure 12:
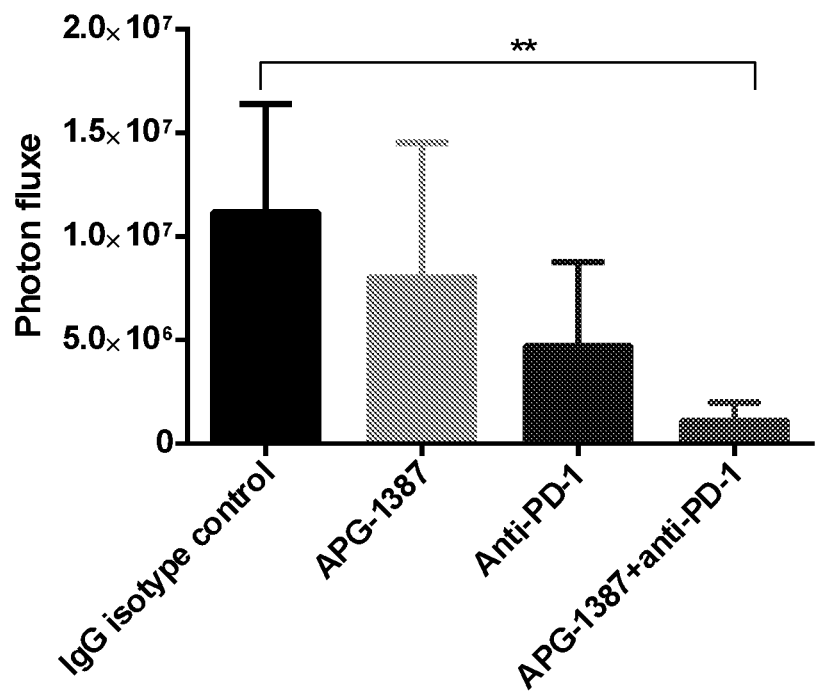
Figure 12:
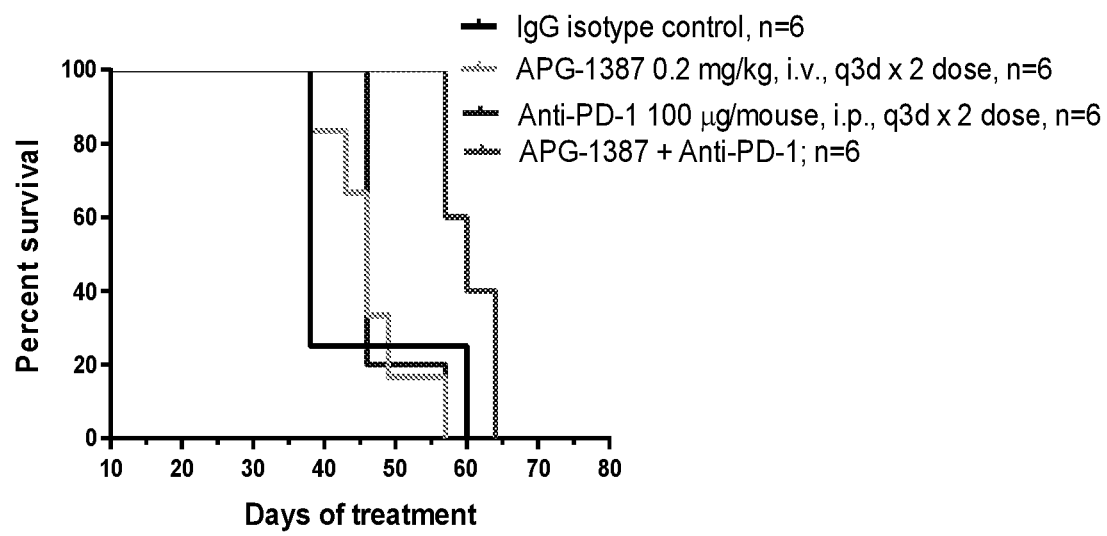

As shown in FIGS. 12A and 12B, on day 7 after administration, the fluorescence intensity of the animals in the APG-1387 and anti-PD-1 antibody combination group was significantly weaker than that of the control group and the two single-agent groups, indicating that the combination has a synergistic anti-tumor effect. As shown in FIGS. 12C and 12D, APG-1387 in combination with anti-PD-1 antibody significantly prolonged the survival time of mice. There was no significant weight loss in any treatment group.

In summary, the combination of APG-1387 and anti-PD-1 antibody showed a significant synergistic anti-tumor effect and achieved the effect of prolonging the survival of mice.

TABLE 7

Study design

| Group | Animal Number | Treatment | Dose | Route of Administration | Dosing Regimen |
|---|---|---|---|---|---|
| 1 | 6 | APG-1387 vehicle | — | i.v. | q3d × 2 doses |
|   |   | isotype control | 100 μg/mouse | i.p. | q3d × 2 doses |
| 2 | 6 | APG-1387 | 0.2 mg/kg | i.v. | q3d × 2 doses |
| 3 | 6 | Anti-PD-1-antibody | 100 μg/mouse | i.p. | q3d × 2 doses |
| 4 | 6 | APG-1387 | 0.2 mg/kg | i.v. | q3d × 2 doses |
|   |   | Anti-PD-1-antibody | 100 μg/mouse | i.p. | q3d × 2 doses |

Antitumor Effect of APG-1387 Combined with Anti-PD-1 Antibody in the Subcutaneous Xenograft Model of Mice with Murine A20 Lymphoma In order to further verify the effect of APG-1387 combined with anti-PD-1 antibody. In this study, A20 cells were selected and subcutaneously inoculated into the right back of female BALB/c mice at 5×10⁶ cells/mouse. The subcutaneous xenograft model of mice was established to further evaluate the advantages of the combination of the two drugs. In this model, the anti-tumor effect of APG-1387 in combination with anti-PD-1 antibody and docetaxel was also evaluated. See Table 8 for the specific dosing regimen.

Figure 13:
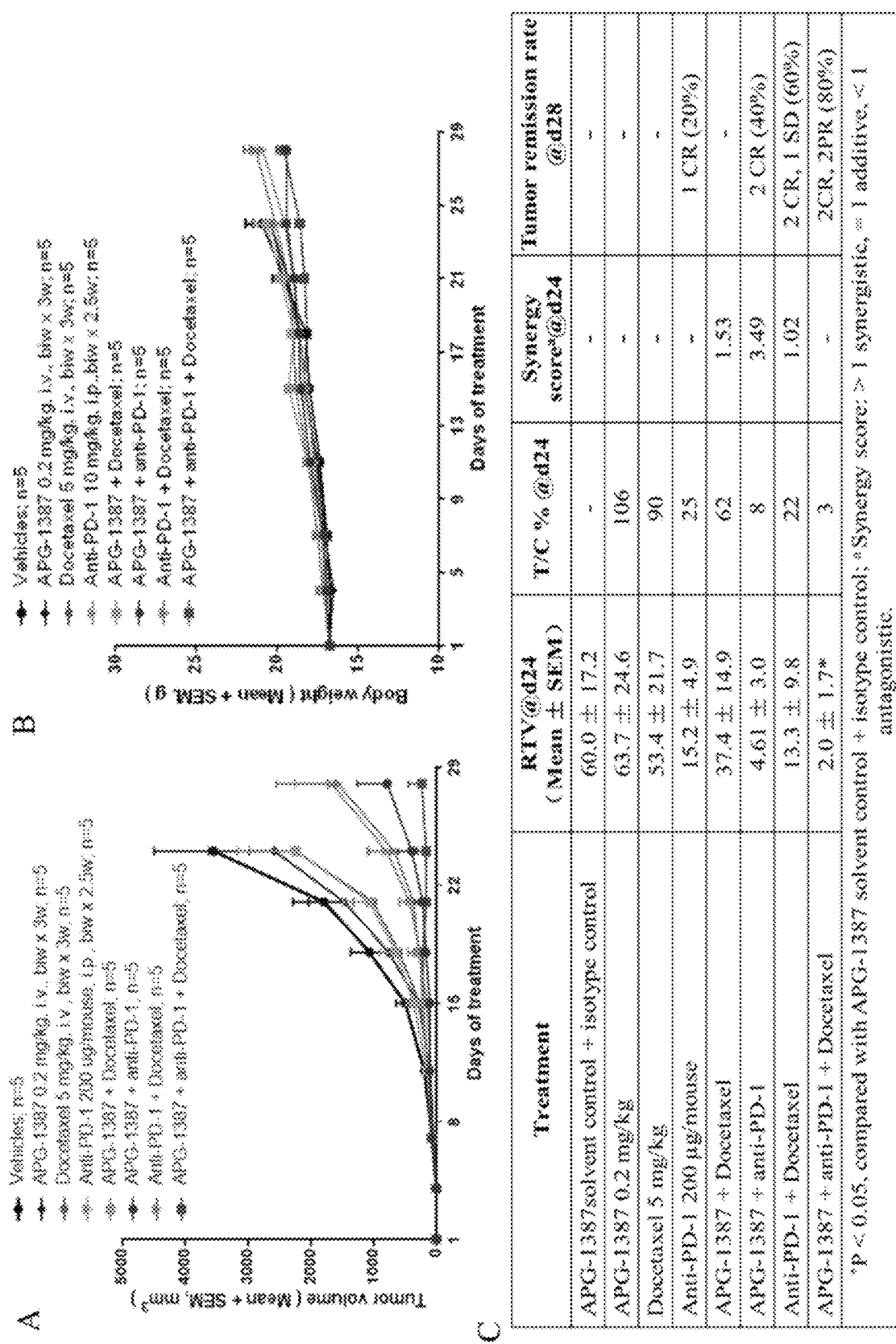
FIG. 13. APG-1387 combined with anti-PD-1 antibody and docetaxel significantly inhibited tumor growth in mice bearing murine A20 the subcutaneous tumor xenograft ((FIG. 13A, 13B) and was well tolerated (FIG. 13C).

As shown in FIGS. 13A and 13B, on the 24th day after administration, the anti-tumor effect of APG-1387 and docetaxel alone or in combination was not significant in the model. The anti-PD-1 antibody alone showed some anti-tumor effect. The T/C value was 25% on the 24th day after administration. One animal showed complete regression on the 28th day after administration, and the tumor remission rate was 20%. After combining APG-1387 with anti-PD-1 antibody, the anti-tumor effect was significantly enhanced. The T/C value was 8%, and the two drugs had a synergistic relationship. The synergy coefficient was 3.49, and two animals reached complete regression on the 28th day after administration and the tumor remission rate was 40%, further demonstrating the advantages of this drug combination. The anti-tumor effect was further enhanced when APG-1387 was combined with anti-PD-1 antibody and docetaxel. The T/C value of the three-drug combination was 3%. Two animals reached complete regression on the 28th day after administration, two animals reached partial regression, and the tumor remission rate was 80%. As shown in FIG. 13C, treatment was well tolerated by the animals in each group, and no significant decrease in body weight occurred.

The above results indicate that APG-1387 enhances the anti-tumor activity of anti-PD-1 antibodies in this model. APG-1387 has superior anti-tumor effect in combination with anti-PD-1 antibody and docetaxel.

TABLE 8

Study design

| Group | Animal Number | Treatment | Dose | Route of Administration | Dosing Regimen |
|---|---|---|---|---|---|
| 1 | 5 | APG-1387 vehicle | — | i.v. | biw × 3w |
|   |   | isotype control | 200 μg/mouse | i.p. | biw × 3w |
| 2 | 5 | APG-1387 | 0.2 mg/kg | i.v. | biw × 3w |
| 3 | 5 | docetaxel | 5 mg/kg | i.v. | biw × 3w |
| 4 | 5 | Anti-PD-1-antibody | 200 μg/mouse | i.p. | biw × 2.5w |
| 5 | 5 | APG-1387 | 0.2 mg/kg | i.v. | biw × 3w |
|   |   | docetaxel | 5 mg/kg | i.v. | biw × 3w |
| 6 | 5 | APG-1387 | 0.2 mg/kg | i.v. | biw × 3w |
|   |   | Anti-PD-1-antibody | 200 μg/mouse | i.p. | biw × 2.5w |
| 7 | 5 | Anti-PD-1-antibody | 200 μg/mouse | i.p. | biw × 2.5w |
|   |   | docetaxel | 5 mg/kg | i.v. | biw × 3w |
| 8 | 5 | APG-1387 | 0.2 mg/kg | i.v. | biw × 3w |
|   |   | Anti-PD-1-antibody | 200 μg/mouse | i.p. | biw × 2.5w |
|   |   | docetaxel | 5 mg/kg | i.v. | biw × 3w |

Analysis of the Effect of APG-1387 as a Single-Agent or in Combination with Anti-PD-1 Antibody on the Activation of Tumor Infiltrating Lymphocytes and Spleen Cells in Healthy Mice As mentioned above, APG-1387 in combination with anti-PD-1 antibody has a significant inhibitory effect on tumor growth in models such as mouse MC38 colon cancer model and ID8-Luc ovarian cancer model. However, for in vitro experiments, APG-1387 had no significant growth inhibitory effect on several mouse tumor cell lines such as MC38 cells and ID8-Luc cells (results not shown). Therefore, we speculated that APG-1387 may exert anti-tumor effects in vivo by acting on other cells, such as immune cells. To validate this hypothesis, we used MC38, ID8-Luc cells and PLC/PRF/5 cell lines to build a mouse xenograft model. The spleen, draining lymph nodes and tumor tissues of MC38 tumor-bearing mice were collected 24 hours after the last administration. Ascites of ID8-Luc tumor mice, tumor tissues of PLC/PRF/5 tumor mice were subjected to tumor infiltrating lymphocyte analysis. The proportion of lymphocytes in the APG-1387 treatment group and control group was analyzed to explore the potential mechanism of anti-tumor effect of APG-1387 combined with anti-PD-1 antibody. The specific dosing regimen is shown in Table 9-Table 11.

TABLE 9

Study design: MC38 mouse xenograft model

| Treatment | Animal Number | Drug | Dose | Route of Administration | Dosing Regimen |
|---|---|---|---|---|---|
| 1 | 5 | APG-1387 vehicle | — | i.v. | q3d × 2 doses |
| 2 | 5 | APG-1387 | 0.2 mg/kg | i.v. | q3d × 2 doses |

TABLE 10

Study design: ID8-Luc mouse xenograft model

| Treatment | Animal Number | Drug | Dose | Route of Administration | Dosing Regimen |
|---|---|---|---|---|---|
| 1 | 5 | APG-1387 vehicle | — | i.v. | q3d × 2 doses |
|  |  | isotype control | 100 μg/mouse | i.p. | q3d × 2 doses |
| 2 | 5 | APG-1387 | 0.2 mg/kg | i.v. | q3d × 2 doses |
| 3 | 5 | Anti-PD-1-antibody | 100 μg/mouse | i.p. | q3d × 2 doses |
| 4 | 5 | APG-1387 | 0.2 mg/kg | i.v. | q3d × 2 doses |
|  |  | Anti-PD-1-antibody | 100 μg/mouse | i.p. | q3d × 2 doses |

TABLE 11

Study design: PLC/PRF/5 mouse xenograft model

| Treatment | Animal Number | Drug | Dose | Route of Administration | Dosing Regimen |
|---|---|---|---|---|---|
| 1 | 7 | APG-1387 vehicle | — | i.v. | qd × 5 doses |
| 2 | 7 | APG-1387 | 5 mg/kg | i.v. | qd × 5 doses |

Figure 14:
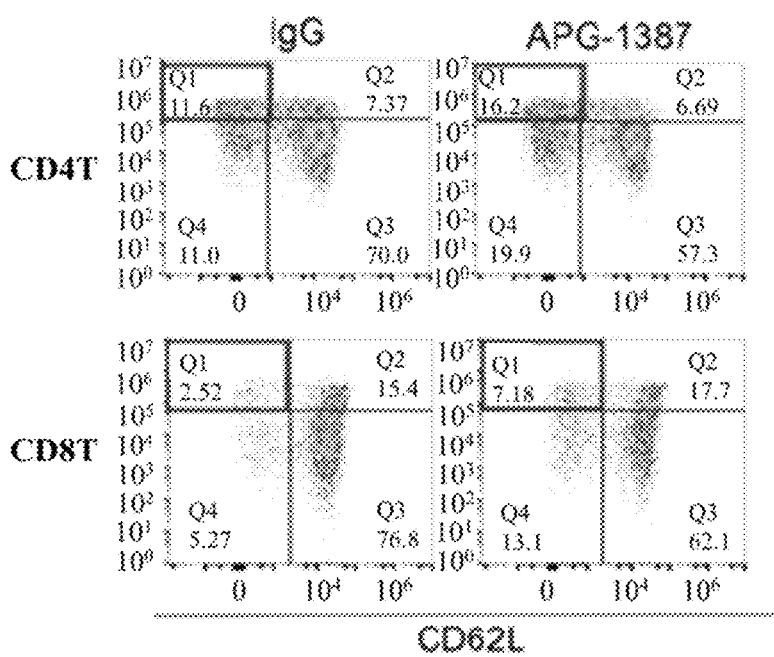
FIG. 14. APG-1387 as a single agent significantly up-regulated the ratio of effector memory CD4+ T and CD8+ T cells in the spleen (FIG. 14A), and significantly up-regulated the proportion of NK cells in the tumor tissue in the MC38 model (FIG. 14B).
Figure 14:
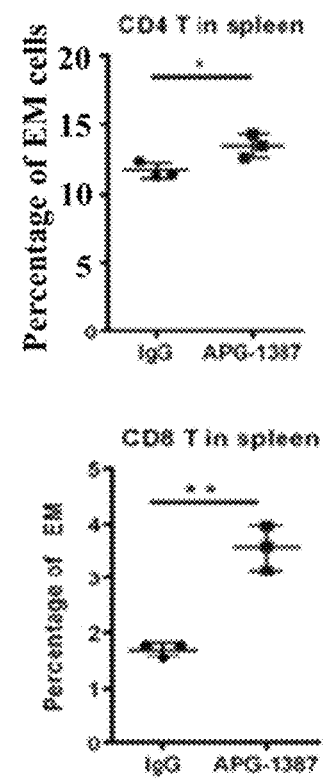
Figure 14:
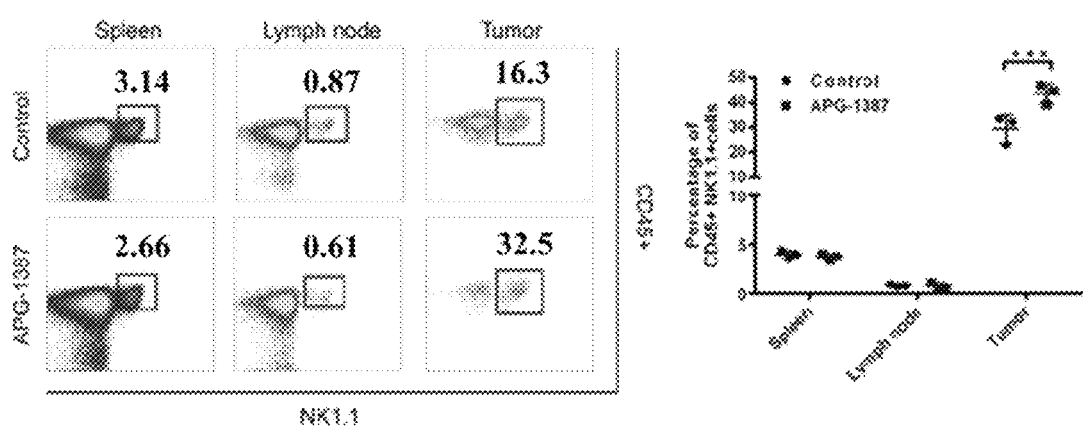

The effects of APG-1387 as a single-agent on mouse spleen, draining lymph nodes, and tumor infiltrating lymphocytes were analyzed in the MC38 model. As shown in FIG. 14A, APG-1387 significantly up-regulated the ratio of effector memory CD8+ T cells (CD44+CD62L-CD3+CD8+ T) and CD4+ T cells (CD44+CD62L-CD3+CD4+T) in spleen tissues.

Analysis of the proportion of NK cells found that APG-1387 as a single agent had no significant effect on the proportion of NK cells in the spleen and lymph nodes, but APG-1387 significantly up-regulated the proportion of NK cells in tumor tissues. The difference, compared to the control group, is statistically significant (FIG. 14B).

Effector memory T cells have memory-specific antigens and the effect of releasing lymphokines. If the same antigen re-invades, the effector memory T cells can rapidly proliferate, destroy the antigen, and enhance the body's immunity to the antigens. APG-1387 increases the proportion of effector T cells (CD8+ and CD4+ T cells) in the spleen, which means it also enhances the body's adaptive immune system function. NK cells are vital cytotoxic lymphocytes in the innate and adaptive immune systems. They have the ability to directly kill malignant target cells and interact with antigen presenting cells and T cells (Vivier et al., Science 331, 44-49.). APG-1387 up-regulates the proportion of NK cells in tumor tissues, demonstrating its role in activating the innate and adaptive immune system.

Figure 15:
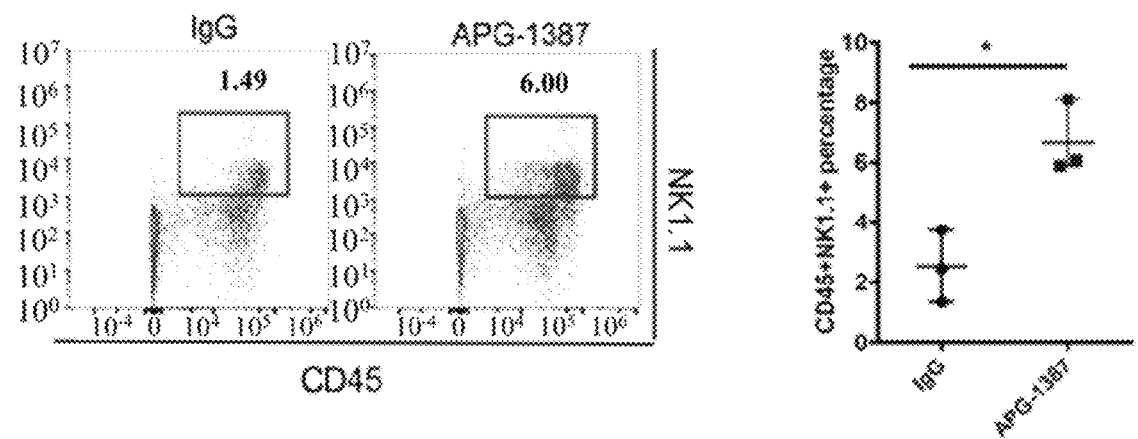
FIG. 15. APG-1387 significantly up-regulated the proportion of NK cells (FIG. 15A), and its combination with anti-PD-1 antibody significantly up-regulated the proportion of effector memory CD8+ T cells in ascites samples (FIG. 15B).
Figure 15:
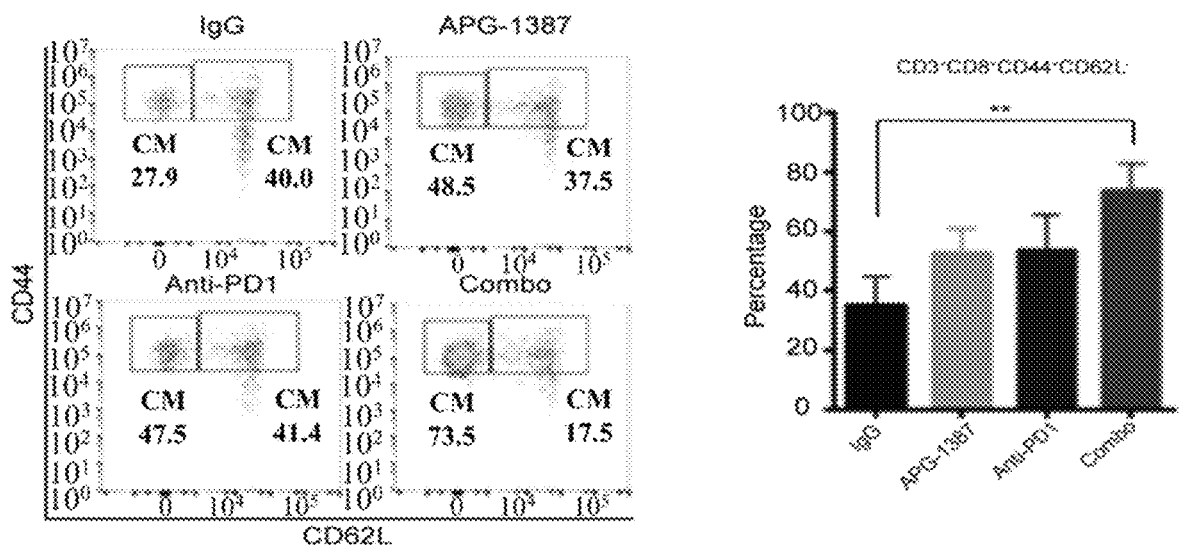

In the ID8-Luc mouse ovarian cancer model, the effects of APG-1387 and anti-PD-1 antibody as single agents and APG-1387 and anti-PD-1 antibody as a combination on ID8-Luc tumor mouse ascites lymphocytes were examined. The result, as shown in FIG. 15, indicates that APG-1387 alone up-regulated the proportion of NK cells in ascites in this model (FIG. 15A). In another independent experiment, it was found that the separate administration of APG-1387 and anti-PD-1 antibodies increased the proportion of effector memory CD8+ T cells to a certain extent, but the combination of APG-1387 and anti-PD-1 increased the it significantly. The difference between the proportion of effector memory CD8+ T cells in the APG-1397 and anti-PD-1 combination group and the control group was statistically significant ($P<0.01$, FIG. 15B).

The above results indicate that APG-1387 has the function of enhancing innate immune systems, and its combination with anti-PD-1 antibody can further enhance the function of the adaptive immune system.

Figure 16:
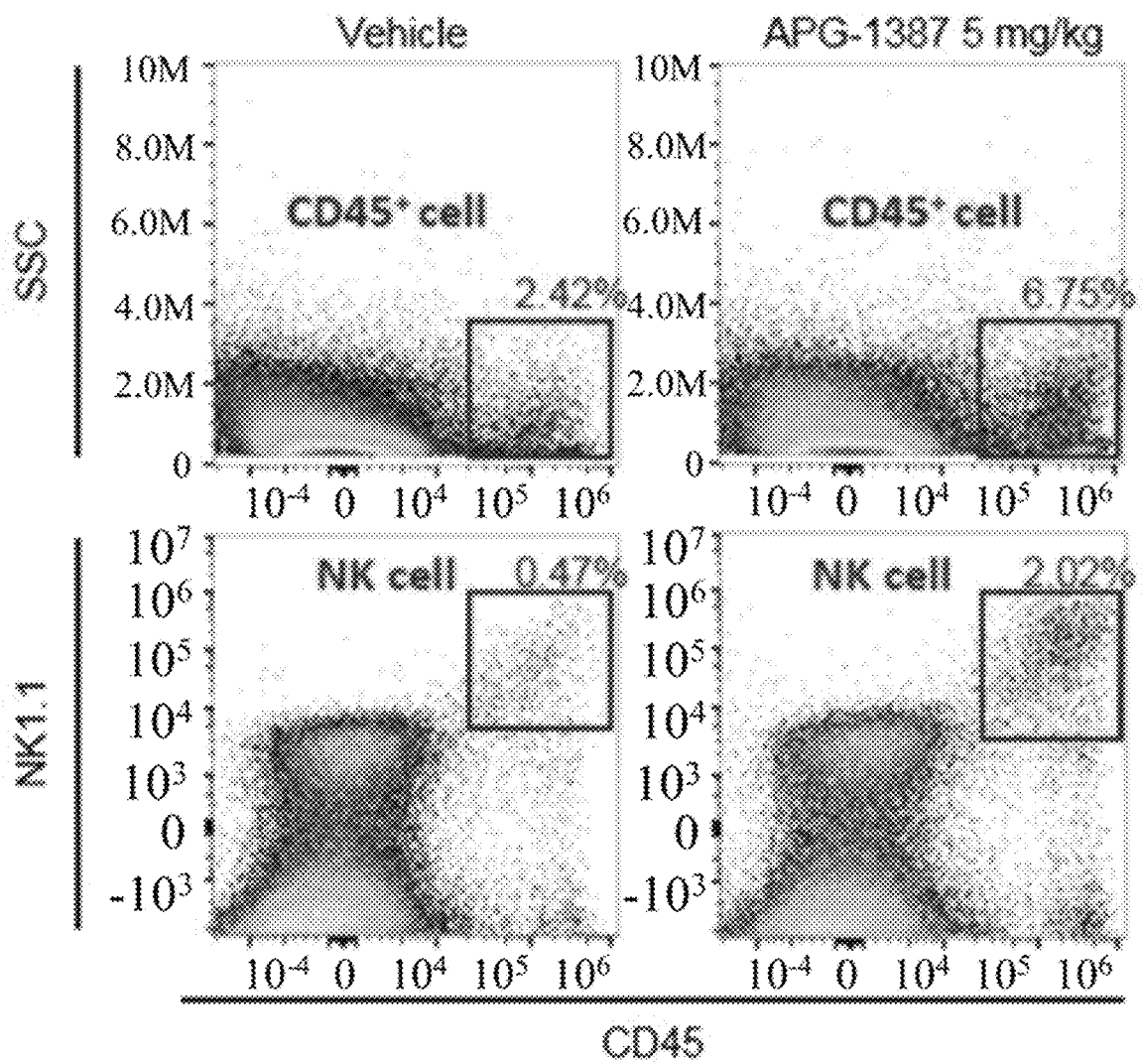
FIG. 16. APG-1387 significantly increased the ratio of tumor infiltrating CD45+ and NK cells in the PLC/PRF/5 mouse model.
Figure 16:
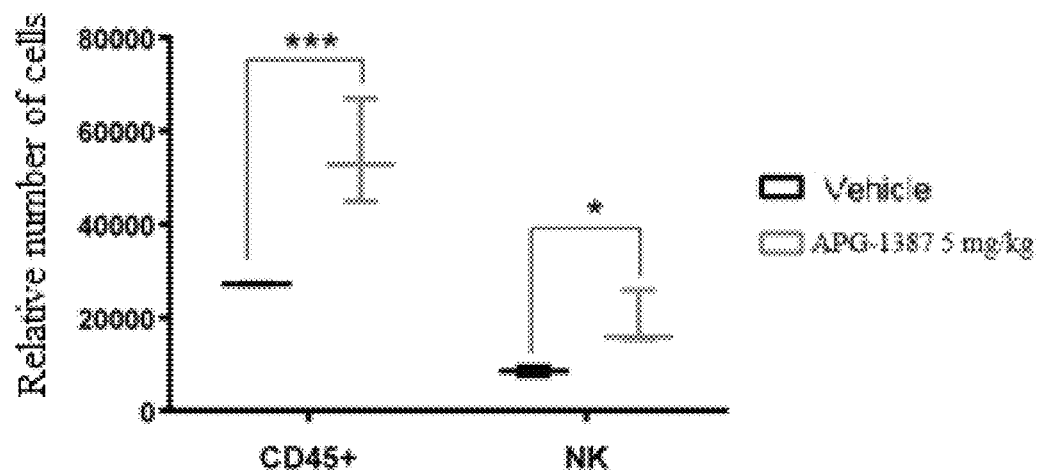

In the infiltrating lymphocyte analysis of PLC/PRF/5 mouse liver cancer tissue, APG-1387 (5 mg/kg) administration significantly increased the ratio of tumor-infiltrating CD45+ T cells and NK cells (FIG. 16). This result reaffirmed that APG-1387 can increase the number of tumor infiltrating NK cells and enhance the innate anti-tumor immune function of the body.

The Effect of APG-1387 as a Single Agent on the Activation of Spleen Cells of C57BL/6 Mice In Vivo Next, we intraperitoneally administered different dosages of APG-1387 to healthy C57BL/6 mice every day. Each group has 3 mice. After 7 days of continuous administration, the spleen was taken to obtain a single cell suspension. NK, macrophage, dendritic cells and T cells were analyzed by flow cytometry to obtain the proportion of these subsets, thus evaluate the effect of APG-1387 on each immune cell subpopulation.

TABLE 12

Study design

| Treatment | Animal Number | Drug | Dose | Route of Administration | Dosing Regimen |
|---|---|---|---|---|---|
| 1 | 3 | APG-1387 vehicle | — | i.p. | qd × 7 doses |
| 2 | 3 | APG-1387 | 0.05 mg/kg | i.p. | qd × 7 doses |
| 3 | 3 | APG-1387 | 0.2 mg/kg | i.p. | qd × 7 doses |
| 4 | 3 | APG-1387 | 0.8 mg/kg | i.p. | qd × 7 doses |

Figure 17:
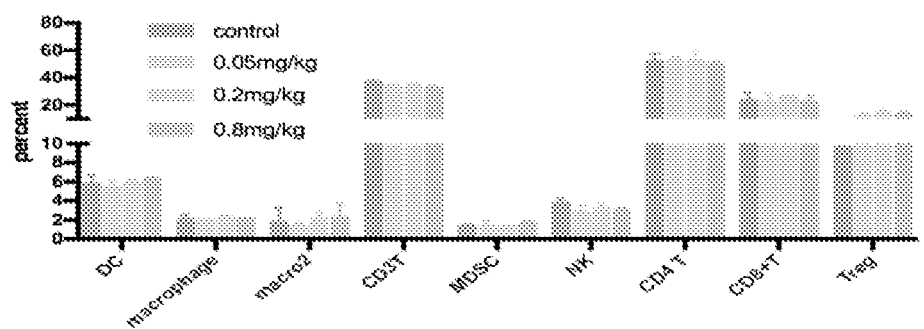
FIG. 17. APG-1387 had no effect on the proportion of the immune cells in the spleen (FIG. 17A), and significantly increased MHC-II expression in spleen cells of C57 mice in vivo (FIG. 17B).
Figure 17:
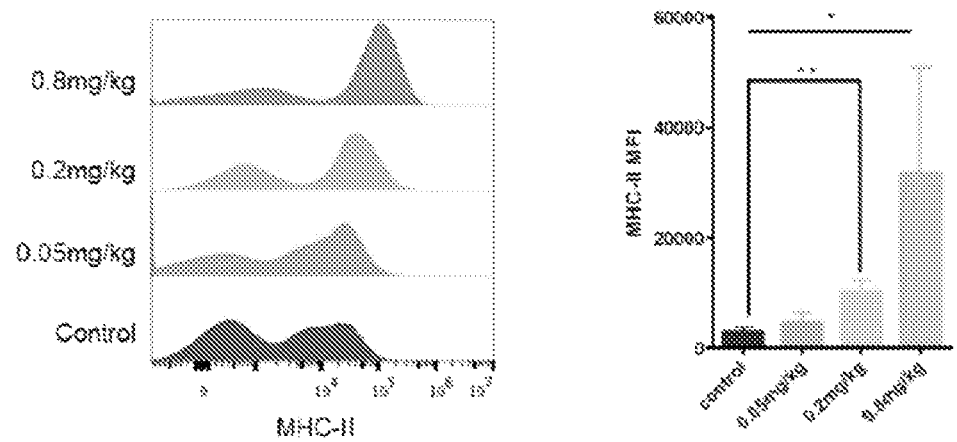

The results are shown in FIG. 17. The three dosage groups of APG-1387 (0.05 mg/kg, 0.2 mg/kg, and 0.8 mg/kg) had no effect on the proportion of these 9 types of immune cells in the spleen (FIG. 17A). However, as the dosage of APG- 1387 increased, the average fluorescence intensity of spleen cells MHC-II also gradually increased. APG-1387 significantly increased MHC-II expression levels at dosages of 0.2 and 0.8 mg/kg (FIG. 17B).

In spleen cells, MHC-II-expressing cells mainly include antigen-presenting cells such as macrophages, B cells, and dendritic cells. The primary function of major histocompatibility complex (MHC) II molecules is to present processed antigens (primarily exogenous antigens) to CD4+ T lymphocytes. Therefore, MHC II molecules are critical for initiating antigen-specific immune responses. APG-1387 can increase the expression of MHC-II molecules in spleen cells, suggesting that APG-1387 has the effect of activating an antigen-specific immune response.

Anti-Tumor Effect of APG-1387 Combined with Anti-PD-1 Antibody and Anti-IL-12 Antibody in Mouse Subcutaneous Xenograft Model of Murine MC38 Colon Cancer As mentioned above, the combination of APG-1387 and anti-PD-1 antibody has a significant synergistic anti-tumor effect in mouse subcutaneous xenograft models such as MC38 and ID8-Luc. Analyses of mouse spleen, lymph nodes, and tumor (ascites) infiltrating lymphocytes found that APG-1387 alone increased the number of NK cells in tumor tissue and ascites. In in vitro cell experiments, APG-1387 stimulated tumor cells to secrete IL-12 (APG-1387-PH-01). IL-12 is an antigen-presenting cell-derived (APC-derived) cytokine that stimulates T and NK cells to secrete IFN-γ and enhances the proliferation and cytolytic activity of these cells (Gately et al., Annu Rev Immunol 16, 495-521). To further determine whether the synergistic anti-tumor effect of APG-1387 and anti-PD-1 antibodies is dependent on IL-12, we administered anti-IL-12 antibodies in the MC38 model to perform IL-12 blocking experiments. See Table 13 for specific dosing regiments.

TABLE 13

Study design: MC38 mouse xenograft model

| Treatment | Animal Number | Drug | Dose | Route of Administration | Dosing Regimen |
|---|---|---|---|---|---|
| 1 | 4 | APG-1387 vehicle | — | i.v. | q3d × 2 doses |
|   |   | isotype control | 100 µg/mouse | i.p. | q3d × 2 doses |
| 2 | 4 | APG-1387 | 0.2 mg/kg | i.v. | q3d × 2 doses |
|   |   | Anti-PD-1-antibody | 100 µg/mouse | i.p. | q3d × 2 doses |
| 3 | 4 | APG-1387 | 0.2 mg/kg | i.v. | q3d × 2 doses |
|   |   | Anti-PD-1-antibody | 100 µg/mouse | i.p. | q3d × 2 doses |
|   |   | Anti-IL-12-antibody | 500 µg/mouse | i.p. | q3d × 2 doses |

Figure 18:
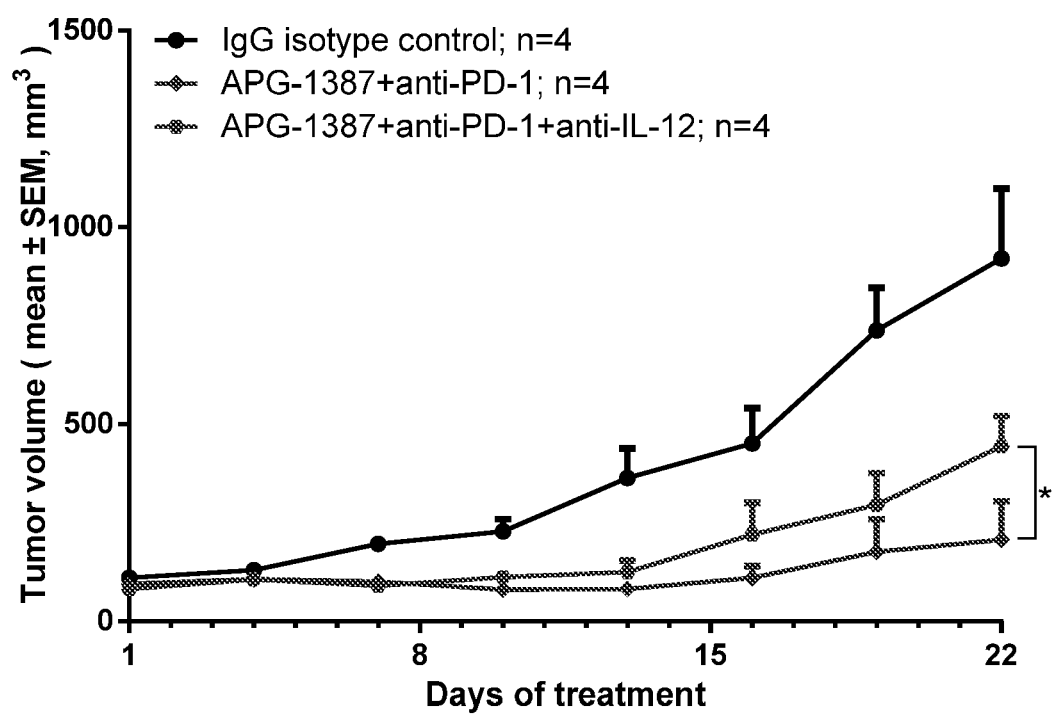
FIG. 18. The anti-tumor effect of APG-1387 in combination with anti-PD-1 antibody in mice bearing murine MC38 subcutaneous tumor xenograft is dependent on IL-12.

As shown in FIG. 18, APG-1387 combined with anti-PD-1 antibody had a significant anti-tumor effect on the 22nd day after administration, but after combing with anti-IL-12 antibody and blocked IL-12 function, the antitumor effect of the drug combination was significantly attenuated ($P<0.05$).

The above results indicate that the combined anti-tumor effect of APG-1387 with an anti-PD-1 antibody is dependent on the function of IL-12. The results of this experiment also validated the synergistic anti-tumor effect of APG-1387 in combination with anti-PD-1 antibody in the MC38 model.

CONCLUSION

This study evaluated the antitumor effect of the combination of APG-1387 and anti-PD-1 antibody in three mouse xenograft models: of MC38 colon cancer subcutaneous xenograft, ID8-Luc orthotopic ovarian xenograft and A20 lymphoma subcutaneous xenograft. The experimental results of the three xenograft models confirmed that APG-1387 combined with immunological checkpoint inhibitor anti-PD-1 antibody has a synergistic anti-tumor effect and can translate to better survival benefits. In the A20 model, the tumor remission rate of anti-PD-1 antibody alone was 20% (one animal tumor reached complete regression, i.e., CR efficacy); APG-1387 combined with anti-PD-1 antibody achieved 40% tumors remission rate (2 animals reached CR), which further demonstrated the advantages of the combination; APG-1387 combined with anti-PD-1 antibody and docetaxel further increased the tumor remission rate to 80% (2 animals reached CR, 2 animals reached partial regression, i.e. PR efficacy), suggesting that the combination of these three drugs has great potential.

To explore the synergistic anti-tumor mechanism of APG-1387 and anti-PD-1 antibodies, we performed a series of tumor infiltrating lymphocyte assays in the MC38, ID8-Luc, and PLC/PRF/5 models. It was found that APG-1387 alone increased the number of effector memory T cells in spleen tissues in the MC38 model. In the ID8-Luc model, APG-1387 combined with anti-PD-1 antibodies significantly increased the number of effector memory T cells in ascites samples. Most importantly, APG-1387 alone increased the proportion of infiltrating NK cells in the tumor tissues in the above three models. These results suggest that APG-1387 may have a synergistic anti-tumor effect with anti-PD-1 antibodies by increasing the proportion of NK cells that are infiltrating tumor tissues. IL-12 is an important cytokine required for NK cell activation and killing. The anti-tumor effect of APG-1387 and anti-PD-1 antibody was significantly attenuated after anti-IL-12 antibody blocked IL-12 function, indicating that the anti-tumor effect of combing APG-1387 and anti-PD-1 antibody is dependent on the functions of IL-12. In addition, the administration of APG-1387 was also found to increase the expression of MHC-II in spleen cells of healthy mice during spleen analysis. These results indicate that APG-1387 can synergize with anti-PD-1 antibodies by participating in multiple aspects of anti-tumor immunity, including increasing the number of effector memory T cells, NK cell ratio, and increasing the expression of MHC-II molecules in immune cells.

Currently, APG-1387 is undergoing a phase 1/2 clinical trial in patients with advanced solid tumors and hematologic malignancies (NCT03386526). The above experimental results indicate APG-1387 as a single drug was well tolerated b under the dosing and administration regimen used in this study. When combined with anti-PD-1 antibodies, no significant weight loss was observed in the experimental animals, and no other significant drug-related toxicity was observed.

APG-1387 can be combined with immunological checkpoints inhibitor anti-PD-1 antibodies for the clinical trial development of different tumors.

Various modifications of the invention in addition to those described herein will be apparent to those skilled in the art. Such modifications are also intended to fall within the scope of the appended claims. Each of the references (including all

The invention claimed is:

1. A method for treating cancer, suppressing_cancer, reducing the severity of cancer, lowering the risk of cancer, or inhibiting the metastasis of cancer in an individual, the method comprising administering to the individual a therapeutically effective amount of an IAP inhibitor, a therapeutically effective amount of a modulator of an immune checkpoint molecule, and a therapeutically effective amount of a tubulin inhibitor;
wherein the IAP inhibitor is APG-1387, the modulator of an immune checkpoint molecule is anti-PD-1 antibody, and the tubulin inhibitor is docetaxel or paclitaxel.

2. The method of claim 1, wherein the modulator of an immune checkpoint molecule is selected from the group consisting of pembrolizumab, ipilimumab, nivolumab, atezolizumab, avelumab, durvalumab, AGEN-1884, BMS-986016, CS1001, CS-1002, LAG525, MBG453, MEDI-570, OREG-103/BY40, lirilumab, tremelimumab, JS001, SHR-1210, BGB-A317, IBI-308, REGN2810, JS003, SHR-1316, KN035 and BMS-936559.

3. The method of claim 1, wherein the cancer is selected from the group consisting of adrenocortical cancer, anal cancer, cholangiocarcinoma, bladder cancer, bone cancer, bone metastasis cancer, adult brain/central nervous system tumor, childhood brain/central nervous system tumor, breast cancer, male breast cancer, childhood cancer, Castleman disease, Merkel cell carcinoma, cervical cancer, colon cancer, colorectal cancer, endometrial cancer, esophageal cancer, Ewing's sarcoma family tumor, eye cancer, gallbladder cancer, digestive tract cancer, gastrointestinal stromal tumor (GIST), trophoblastic cancer, head and neck cancer, Kaposi's sarcoma, renal cancer, renal cell cancer, laryngeal and hypopharyngeal cancer, leukemia, liver cancer, lung cancer, lymphoma, cutaneous lymphoma, malignant mesothelioma, multiple myeloma, myelodysplastic syndrome, nasal and nasalsinus cancer, nasopharyngeal cancer, neuroblastoma, Hodgkin's lymphoma, non-Hodgkin's lymphoma, childhood non-Hodgkin's lymphoma, oral and oropharyngeal cancer, osteosarcoma, ovarian cancer, pancreatic cancer, penile cancer, malignant pituitary tumor, prostate cancer, retinoblastoma, rhabdomyosarcoma, salivary gland cancer, sarcoma, skin cancer, small intestinal cancer, testicular cancer, thymic cancer, thyroid cancer, vaginal cancer, vulvar cancer, Waldenstrom macroglobulinemia, Wilms tumor, urothelial cancer, microsatellite instability solid tumor and choriocarcinoma.

4. The method of claim 1, wherein the IAP inhibitor is administered in an amount of about 0.005 mg/day to about 5000 mg/day.

5. The method of claim 1, wherein the modulator of an immune checkpoint molecule or the tubulin inhibitor is administered in an amount of about 0.005 mg/week to about 5000 mg/week.

6. The method of claim 1, wherein the IAP inhibitor, modulator of an immune checkpoint molecule, and tubulin inhibitor are administered together, concurrently, sequentially or alternately.

7. The method of claim 1, wherein the IAP inhibitor, modulator of an immune checkpoint molecule or tubulin inhibitor is administered for one or more courses of treatment, wherein each course of treatment lasts for at least 3 days; wherein for each course of treatment, administration is performed 1, 2, 3, 4, 5, 6, 7, 8, 9 or 10 times; and the interval between every two courses of treatment is 0, 1, 2, 3, 4, 5, 6, 7, 8, 9, 10 days, two weeks, three weeks, four weeks, one month or two months.

8. The method of claim 1, wherein the individual suffers from a refractory cancer, a recurrent cancer or a resistant cancer that is resistant to a cancer therapy comprising the modulator of an immune checkpoint molecule and/or the tubulin inhibitor.

9. A pharmaceutical composition comprising an IAP inhibitor, a modulator of an immune checkpoint molecule, a tubulin inhibitor, and a pharmaceutically acceptable carrier;
wherein the IAP inhibitor is APG-1387, the modulator of an immune checkpoint molecule is anti-PD-1 antibody, and the tubulin inhibitor is docetaxel or paclitaxel.

10. A kit comprising:
(a) a first component in a first container, the first component comprising an IAP inhibitor;
(b) a second component in a second container, the second component comprising a modulator of an immune checkpoint molecule; and
(c) a third component in a third container, the third component comprising a tubulin inhibitor;
wherein the IAP inhibitor is APG-1387, the modulator of an immune checkpoint molecule is anti-PD-1 antibody, and the tubulin inhibitor is docetaxel or paclitaxel.

11. A method for treating cancer, suppressing cancer, reducing the severity of cancer, lowering the risk of cancer, or inhibiting the metastasis of cancer in an individual, the method comprising administering to the individual a therapeutically effective amount of an IAP inhibitor and a therapeutically effective amount of a modulator of an immune checkpoint molecule;
wherein the IAP inhibitor is APG-1387 and the modulator of an immune checkpoint molecule is anti-PD-1 antibody; and
wherein the cancer is selected from the group consisting of colon cancer, colorectal cancer, ovarian cancer, lymphoma, nasopharyngeal cancer and liver cancer.

12. A pharmaceutical composition for use in the treatment of cancer comprising an IAP inhibitor, a modulator of an immune checkpoint molecule, and a pharmaceutically acceptable carrier;
wherein
the IAP inhibitor is APG-1387 and the modulator of an immune checkpoint molecule is anti-PD-1 antibody; the cancer is selected from the group consisting of colon cancer, colorectal cancer, ovarian cancer, lymphoma, nasopharyngeal cancer and liver cancer.

13. The method of claim 1, wherein the method comprises at least one 21-day treatment cycle, wherein the IAP inhibitor is administrated on days 1, 8 and 15 of the consecutive 3-weeks of the treatment cycle.

14. The method of claim 13, wherein APG-1387 is administered via an intravenous infusion.

15. The method of claim 13, wherein the therapeutically effective amount is from about 15 mg to about 100 mg, or is from 20 to 45 mg, or from 20 mg to 60 mg of IAP inhibitor.

16. The method of claim 13, wherein the therapeutically effective amount is 20 mg, 30 mg, 45 mg, 60 mg or 80 mg.

17. The method of claim 13, wherein the cancer is metastatic pancreatic cancer, colorectal cancer, ovarian cancer, lymphoma, or liver cancer.

18. The method of claim 13, wherein the method further comprises administering a therapeutically effective amount of carboplatin.

19. The method of claim 11, wherein and the modulator of an immune checkpoint molecule is pembrolizumab, and wherein APG-1387 is administered with pembrolizumab for treating a patient suffering from advanced solid tumors or hematologic malignancies.

20. The method of claim 13, wherein the IAP inhibitor is APG-1387, the modulator of an immune checkpoint molecule is pembrolizumab, and further comprising administration of docetaxel, and wherein APG-1387 is administered with pembrolizumab and docetaxel for treating a patient suffering from advanced solid tumors or hematologic malignancies.

21. The method of claim 3, wherein the cancer is head and neck cancer, microsatellite instability solid tumor, Hodgkin's lymphoma, non-Hodgkin's lymphoma, non-small cell lung cancer, renal cell cancer, bladder cancer, melanoma, squamous cell carcinoma, Merkel cell tumor, urothelial cancer, nasopharyngeal cancer and colorectal cancer.

22. The method of claim 17, wherein the cancer is hepatocellular carcinoma.

* * * * *